(12) United States Patent
Jaffray et al.

(10) Patent No.: US 8,135,111 B2
(45) Date of Patent: Mar. 13, 2012

(54) CONE BEAM COMPUTED TOMOGRAPHY WITH A FLAT PANEL IMAGER

(75) Inventors: David A. Jaffray, Ontario (CA); John W. Wong, Bloomfield Hills, MI (US); Jeffrey H. Siewerdesen, Ann Arbor, MI (US)

(73) Assignee: William Beaumont Hospital, Royal Oak, MI (US)

( * ) Notice: Subject to any disclaimer, the term of this patent is extended or adjusted under 35 U.S.C. 154(b) by 0 days.

(21) Appl. No.: 12/917,079

(22) Filed: Nov. 1, 2010

(65) Prior Publication Data

US 2011/0228906 A1    Sep. 22, 2011

Related U.S. Application Data

(60) Continuation of application No. 12/313,646, filed on Dec. 21, 2008, now Pat. No. 7,826,592, which is a division of application No. 11/023,037, filed on Dec. 27, 2004, now Pat. No. 7,471,765, which is a continuation of application No. 09/788,335, filed on Feb. 16, 2001, now Pat. No. 6,842,502.

(60) Provisional application No. 60/183,590, filed on Feb. 18, 2000.

(51) Int. Cl.
*A61N 5/10* (2006.01)
*G01D 18/00* (2006.01)

(52) U.S. Cl. .......................... 378/65; 378/207
(58) Field of Classification Search .................. 378/65, 378/207
See application file for complete search history.

(56) References Cited

U.S. PATENT DOCUMENTS

| 4,547,892 A | 10/1985 | Richey et al. |
| 5,039,867 A | 8/1991 | Nishihara et al. |
| 5,157,707 A | 10/1992 | Ohlson |
| 5,394,452 A | 2/1995 | Swerdloff et al. |
| 5,411,026 A | 5/1995 | Carol |
| 5,521,957 A | 5/1996 | Hansen |
| 5,661,773 A | 8/1997 | Swerdloff et al. |

(Continued)

FOREIGN PATENT DOCUMENTS

EP    09 229 43 A2    6/1999

(Continued)

OTHER PUBLICATIONS

Antonuk, LE, et al., "A Real-Time, Flat-Panel, Amorphous Silicon, Digital X-Ray Imager", *Radiographics*, vol. 15, No. 4, Jul. 1995, pp. 993-1000.

(Continued)

*Primary Examiner* — Allen C. Ho
(74) *Attorney, Agent, or Firm* — Brinks Hofer Gilson & Lione

(57) ABSTRACT

A radiation therapy system that includes a radiation source that moves about a path and directs a beam of radiation towards an object and a cone-beam computer tomography system. The cone-beam computer tomography system includes an x-ray source that emits an x-ray beam in a cone-beam form towards an object to be imaged and an amorphous silicon flat-panel imager receiving x-rays after they pass through the object, the imager providing an image of the object. A computer is connected to the radiation source and the cone beam computerized tomography system, wherein the computer receives the image of the object and based on the image sends a signal to the radiation source that controls the path of the radiation source.

11 Claims, 26 Drawing Sheets

U.S. PATENT DOCUMENTS

| | | | |
|---|---|---|---|
| 5,663,995 | A | 9/1997 | Hu |
| 5,675,625 | A | 10/1997 | Rockseisen |
| 5,719,914 | A | 2/1998 | Rand et al. |
| 5,748,700 | A | 5/1998 | Shepherd et al. |
| 5,751,781 | A | 5/1998 | Brown et al. |
| 5,835,558 | A | 11/1998 | Maschke |
| 5,848,126 | A | 12/1998 | Fujita et al. |
| 5,877,501 | A | 3/1999 | Ivan et al. |
| 5,912,943 | A | 6/1999 | Deucher et al. |
| 5,929,449 | A | 7/1999 | Huang |
| 5,949,811 | A | 9/1999 | Baba et al. |
| 5,999,587 | A * | 12/1999 | Ning et al. ............... 378/4 |
| 6,031,888 | A | 2/2000 | Ivan et al. |
| 6,041,097 | A | 3/2000 | Roos et al. |
| 6,113,264 | A | 9/2000 | Watanabe |
| 6,148,058 | A | 11/2000 | Dobbs |
| 6,152,598 | A | 11/2000 | Tomisaki et al. |
| 6,200,024 | B1 | 3/2001 | Negrelli |
| 6,269,143 | B1 | 7/2001 | Tachibana |
| 6,285,739 | B1 | 9/2001 | Rudin et al. |
| 6,307,914 | B1 * | 10/2001 | Kunieda et al. ............ 378/65 |
| 6,318,892 | B1 | 11/2001 | Suzuki et al. |
| 6,325,537 | B1 | 12/2001 | Watanabe |
| 6,345,114 | B1 * | 2/2002 | Mackie et al. ............. 378/65 |
| 6,385,286 | B1 | 5/2002 | Fitchard et al. |
| 6,385,288 | B1 | 5/2002 | Kanematsu |
| 6,435,715 | B1 | 8/2002 | Betz et al. |
| 6,463,122 | B1 * | 10/2002 | Moore ..................... 378/65 |
| 6,546,073 | B1 | 4/2003 | Lee |
| 6,582,121 | B2 | 6/2003 | Crain et al. |
| 6,760,402 | B2 * | 7/2004 | Ghelmansarai ............ 378/65 |
| 6,842,502 | B2 | 1/2005 | Jaffray et al. |
| 6,865,254 | B2 | 3/2005 | Näfstadius |
| 6,888,919 | B2 | 5/2005 | Graf |
| 6,990,175 | B2 | 1/2006 | Nakashima et al. |
| 7,030,386 | B2 | 4/2006 | Pang et al. |
| 7,227,925 | B1 * | 6/2007 | Mansfield et al. .......... 378/65 |
| 7,471,765 | B2 | 12/2008 | Jaffray et al. |
| 7,657,304 | B2 * | 2/2010 | Mansfield et al. .......... 600/427 |
| 7,826,592 | B2 | 11/2010 | Jaffray et al. |
| 7,945,021 | B2 * | 5/2011 | Shapiro et al. ............. 378/65 |
| 2004/0120452 | A1 | 6/2004 | Shapiro et al. |

FOREIGN PATENT DOCUMENTS

| | | |
|---|---|---|
| JP | 58-94835 A | 6/1983 |
| JP | 07-255717 A | 10/1995 |
| JP | 10-113400 A | 5/1998 |
| JP | 10-511595 | 11/1998 |
| JP | 10-328318 A | 12/1998 |
| JP | 11-99148 A | 4/1999 |
| JP | 11-160440 A | 6/1999 |
| WO | WO 97/13552 A1 | 4/1997 |
| WO | WO 98/52635 A1 | 11/1998 |
| WO | WO 99/03397 A1 | 1/1999 |

OTHER PUBLICATIONS

Antonuk, LE, et al., "Initial Performance Evaluation of an Indirect-Detection, Active Matrix Flat-Panel Imager (AMFPI) Prototype for Megavoltage Imaging", *Int. J. Radiat. Oncol. Biol. Phys.*, vol. 42, No. 2, 1998, pp. 437-454.

Antonuk, LE, et al., "Megavoltage Imaging with a Large-Area, Flat-Panel, Amorphous Silicon Imager", *Int. J. Radiat. Oncol. Biol. Phys.*, vol. 36, No. 3, 1996, pp. 661-672.

Antonuk, LE, et al., "Strategies to Improve the Signal and Noise Performance of Active Matrix, Flat-Panel Imagers for Diagnostic X-Ray Applications", *Med. Phys.*, vol. 27, No. 2, Feb. 2000, pp. 289-306.

Basset, P.G., Wong, J.W. and Aspin, N.: "An Interactive Computer System for Studying Human Mucociliary Clearance", *Computer Biol. Med.* 1979, vol. 9, pp. 97-105.

Bissonnette, JP, et al., "Optimal Radiographic Magnification for Portal Imaging.", *Med. Phys.*, vol. 21, No. 9, Sep. 1994, pp. 1435-1445.

Boyer AL, Butler EB, DiPetrillo TA, Engler MJ, Fraass B, Grant III W, Ling CC, Low DA, Mackie TR, Mohan R, Purdy JA, Roach M, Rosenman JG, Verhey LJ, Wong JW (IMRT Collaborative Working Group): "Intensity-modulated radiotherapy: Current status and issues of interest", *Int. J. Radiat. Oncol. Biol. Phys.* 2001, vol. 54, No. 4, pp. 880-914.

Boyer, A.L. Antonuk, L., Fenster, A. Van Herk, M. Meertens, H., Munro, P., Reinstein, L. and Wong. J.: "A Review of Electronic Portal Imaging Devices (EPIDs)", *Medical Physics*, Jan./Feb. 1992, vol. 19, No. 1, pp. 19: 1-16.

Brown, AP, et al., "Three-Dimensional Photon Treatment Planning for Hodgkin's Disease", *Int. J. Radiat. Oncol. Biol. Phys.*, May 15, 1991, vol. 32, No. 1, pp. 205-215.

Cheng, A, et al., "Systematic Verification of a Three-Dimensional Electron Beam Dose Calculation Algorithm", *Med. Phys.*, 1996, vol. 23, No. 5, pp. 685-693.

Drake, DG, et al., "Characterization of Fluoroscopic Imaging System for kV and MV Radiography", *Med. Phys.*, May 2000, vol. 27, No. 5, pp. 898-905.

Du, MN, et al., "A Multileaf Collimator Field Prescription Preparation System for Conventional Radiotherapy", *Int. J. Radiat. Oncol. Biol. Phys.*, 1994, vol. 30, No. 3, pp. 707-714.

Du, MN, et al., "A Multileaf Collimator Field Prescription Preparation System for Conventional Radiotherapy", *Int. J. Radiat. Oncol. Biol. Phys.*, 1995, vol. 32, No. 2, pp. 513-520.

El-Mohri Y, et al., "Relative Dosimetry Using Active Matrix Flat-Panel Imager (AMFPI) Technology", *Med. Phys.*, Aug. 1999, vol. 26, No. 8, pp. 1530-1541.

Ezz, A, et al., "Daily Monitoring and Correction of Radiation Field Placement Using a Video-Based Portal Imaging System: a Pilot Study", *Int. J. Radiat. Oncol. Biol. Phys.*, 1992, vol. 22, No. 1, pp. 159-165.

Frazier, A, et al., "Dosimetric Evaluation of the Conformation of the Multileaf Collimator to Irregularly Shaped Fields", *Int. J. Radiat. Oncol.Biol. Phys.*, 1995, vol. 33, No. 5, pp. 1229-1238.

Frazier, A, et al., "Effects of Treatment Setup Variation on Beam's Eye View Dosimetry for Radiation Therapy Using the Multileaf Collimator vs. The Cerrobend Block", *Int. J Radiat. Oncol. Biol. Phys.*, 1995, Vol. 33, No. 5, pp. 1247-1256.

Graham, ML, et al., "A Method to Analyze 2-Dimensional Daily Radiotherapy Portal Images from an On-Line Fiber-Optic Imaging System.", *Int. J. Radiat. Oncol. Biol. Phys.*, Mar. 1991, vol. 20, No. 3, pp. 613-619.

Halverson, KJ, et al., "Study of Treatment Variation in the Radiotherapy of Head and Neck Tumors Using a Fiber-Optic On-Line Radiotherapy Imaging System", *Int. J. Radiat. Oncol. Biol. Phys.*, Oct. 1991, vol. 21, No. 5, pp. 1327-1336.

Harms, WB Sr., et al., "A Software Tool for the Quantitative Evaluation of 3D Dose Calculation Algorithms", *Med. Phys.*, Oct. 1998, vol. 25, No. 10, pp. 1830-1839.

Herman MG, Balter JM, Jaffray DA, McGee KP, Munro P, Shalev S, Van Herk M, Wong JW: "Clinical use of electronic portal imaging: Report of AAPM Radiation Therapy Committee Task Group 58", *Med. Phys.* May 2001, vol. 28, No. 5, pp. 712-737.

Jaffray, DA, et al., "Managing Geometric Uncertainty in Conformal Intensity-Modulated Radiation Therapy", *Semin. Radiat. Oncol.*, Jan. 1999, vol. 9, No. 1, pp. 4-19.

Jaffray, DA, et al., "A Radiographic and Tomographic Imaging System Integrated into a Medical Linear Accelerator for Localization of Bone and Soft-Tissue Targets", *Int. J. Radiat. Oncol. Biol. Phys.*, 1999, vol. 45, No. 3, pp. 773-789.

Jaffray, DA, et al., "Activity Distribution of a Cobalt-60 Teletherapy Source", *Med. Phys.*, Mar./Apr. 1991, vol. 18, No. 2, pp. 288-291.

Jaffray, DA, et al., "Cone-Beam Computed Tomography with a Flat-Panel Imager: Initial Performance Characterization", *Med. Phys.* Jun. 2000, vol. 27, No. 6, pp. 1311-1323.

Jaffray, DA, et al., "Dual-Beam Imaging for Online Verification of Radiotherapy Field Placement", *Int. J. Radiat. Oncol. Biol. Phys.*, 1995, vol. 33, No. 5, pp. 1273-1280.

Jaffray, DA, et al., "X-Ray Scatter in Megavoltage Transmission Radiography: Physical Characteristics and Influence on Image Quality", *Med. Phys.*, Jan. 1994, vol. 21, No. 1, pp. 45-60.

Jaffray, DA, et al., "X-Ray Sources of Medical Linear Accelerators: Focal and Extra-Focal Radiation", *Med. Phys.* Sep./Oct. 1993, vol. 20, No. 5, pp. 1417-1427.

Kestin, LL, et al., "Intensity Modulation to Improve Dose Uniformity with Tangential Breast Radiotherapy: Initial Clinical Experience" *Int J. Radiat. Oncol. Biol. Phys.*, 2000, vol. 48, No. 5, pp. 1559-1568.

Kini, VR, et al., "Use of Three-Dimensional Radiation Therapy Planning Tools and Intraoperative Ultrasound to Evaluate High Dose Rate Prostate Brachytherapy Implants", *Int. J. Radiat. Oncol. Biol. Phys.*, 1999, vol. 43, No. 3, pp. 571-578.

Kestin, LL, et al., "Improving the Dosimetric Coverage of Interstitial High-Dose-Rate Breast Implants", *Int. J. Radiat. Oncol. Biol. Phys.*, 2000, vol. 46, No. 1, pp. 35-43.

Laughlin, J.S., Goitein, M., Purdy, J.A. and Sontag, M.R. (writing chairs), "Evaluation of High Energy Photon External Beam Treatment Planning: Project Summary", *Int. J. Rad. Oncol. Biol. Physics.* 1991, vol. 21, pp. 3-8.

Lockman, D., Yan, D., and Wong, J.W., "Estimating the dose variation in a volume of interest with explicit consideration of patient geometric variation", *Med. Phys.* Sep. 2000, vol. 27, No. 9, pp. 2100-2108.

Martinez, A., Yan, D. Lockman, D. Brabbins, D, Kota, K. Sharpe, M., Jaffray, D. Vicini, F., and Wong, J.: "Improvement in dose escalation using the process of adaptive radiation therapyb combined with three dimensional conformal or Intensity modulated beams for prostate cancer", *Int. J. Radiat. Oncol. Biol. Phys.* 2001, vol. 50, No. 5, pp. 1226-1234.

Masterson, M.E. Barest, G., Chui, C. Doppke, K.P., Epperson, R.D., Harms, W.B., Krippner, K., Mohan, R., Slessinger, E.D., Sontag, M.R., Urie, M.M., Wallace, R.E. and Wong, J.W., "Inter-Institutional Experience in Verification of External Photon Dose Calculations", *Int. J. Rad. Oncol. Biol. Physics*, 1991, vol. 21, pp. 37-58.

Michalski, J., Wong, J. Bosch, W., Yan, D. Cheng, A., Gerber, R., Graham, M. Halverson, K., Low, D., Valencenti, R. and Piephoff, J., "An Evaluation of Two Methods of Anatomical Alignment of Radiotherapy Portal Images", *Int. J. Radiat. Oncol. Biol. Phys.*, 1993; vol. 27. No. 5, pp. 1199-1206.

Michalski, JM, et al., "The Use of On-Line Image Verification to Estimate the Variation in Radiation Therapy Dose Delivery", *Int. J. Radiat. Oncol. Biol. Phys.*, 1993, vol. 27, No. 3, pp. 707-716.

Michalski, JM, et al., "Prospective Clinical Evaluation of an Electronic Portal Imaging Device", *Int. J. Radiat. Oncol. Biol. Phys.*, 1996, vol. 34, No. 4, pp. 943-951.

Milliken, BD, et al., "Verification of the Omni Wedge Technique", *Med. Phys.* Aug. 1998, vol. 25, No. 8, pp. 1419-1423.

Mohan, R. (writing chair), "Three-Dimensional Dose Calculations for Radiation Treatment Planning", *Int. J. Rad. Oncol. Biol. Physics*, May 15, 1991; vol. 21, No. 1, pp. 25-36.

Oldham, M., Sapareto, S.A., Li, X.A., Allen, J., Sutlief, S. Wong, O.C. and Wong, J.W., "Practical aspects of in situ $^{16}O(\gamma,n)^{15}O$ activation using a conventional medical accelerator for the purpose of perfusion imaging", *Med. Phys.* Aug. 2001; vol. 28, No. 8, pp. 1669-1678.

Perera, H, et al., "Rapid Two-Dimensional Dose measurement in Brachytherapy Using Plastic Scintillator Sheet: Linearity, Signal-to-Noise Ratio, and Energy Response Characteristics.", *Int. J. Radiat. Oncol. Biol. Phys.*, 1992, vol. 23, No. 5, pp. 1059-1069.

Pisani, L, et al., "Setup Error in Radiotherapy: On-line Correction Using Electronic Kilovoltage and Megavoltage Radiographs", *Int. J. Radiat. Oncol. Biol. Phys.*, 2000, vol. 47, No. 3, pp. 825-839.

Purdy, JA, et al., "State of the Art High Energy Photon Treatment Planning", *Front Radiat. Ther. Oncol.*, 1987, vol. 21, pp. 4-24.

Sharpe, MB, et al., "Compensation of X-Ray Beam Penumbra in Conformal Radiotherapy", *Med. Phys.*, Aug. 2000, vol. 27, No. 8, pp. 1739-1745.

Sharpe, MB, et al., "Monitor Unit Settings for Intensity Modulated Beams Delivered Using a Step-and-Shoot Approach", *Med. Phys.*, Dec. 2000, vol. 27, No. 12, pp. 2719-2725.

Shiu, AS, et al., "Verification Data for Electron Beam Dose Algorithms", *Med. Phys.*, May/Jun. 1992, vol. 19, No. 3, pp. 623-636.

Siewerdsen, JH, et al., "A Ghost Story: Spatio-Temporal Response Characteristics of an Indirect-Detection Flat-Panel Imager", *Med. Phys.*, Aug. 1999, vol. 26, No. 8, pp. 1624-1641.

Siewerdsen, JH, et al., "Cone-Beam Computed Tomography with a Flat-Panel Imager: Magnitude and Effects of X-Ray Scatter", *Med. Phys.*, Feb. 2001, vol. 28, No. 2, pp. 220-231.

Siewerdsen, JH, et al., "Cone-Beam Computed Tomography with a Flat-Panel Imager: Effects of Image Lag", *Med. Phys.*, Dec. 1999, vol. 26, No. 12, pp. 2635-2647.

Siewerdsen, JH, et al., "Empirical and Theoretical Investigation of the Noise Performance of Indirect Detection, Active Matrix Flat-Panel Imagers (AMFPIs) for Diagnostic Radiology", *Med. Phys.*, Jan. 1997, vol. 24, No. 1, pp. 71-89.

Siewerdsen, JH, et al., "Optimization of X-Ray Imaging Geometry (with Specific Application to Flat-Panel Cone-Beam Computed Tomography)", *Med. Phys.*, Aug. 2000, vol. 27, No. 8, pp. 1903-1914.

Siewerdsen, JH, et al., "Signal, Noise Power Spectrum, and Detective Quantum Efficiency of Indirect-Detection Flat-Panel Imagers for Diagnostic Radiology", *Med. Phys.*, May 1998, vol. 25, No. 5, pp. 614-628.

Sontag, M.R. And Purdy, J.A. (writing chairs), "State of the Art of External Photon Beam Radiation Treatment Planning", *Int. J. Rad. Oncol. Biol. Physics*. 1991, vol. 21 No. 1, pp. 9-23.

Stromberg, JS, et al., "Active Breathing Control (ABC) for Hodgkin's Disease: Reduction in Normal Tissue Irradiation with Deep Inspiration and Implications for Treatment", *Int. J. Radiat. Oncol. Biol. Phys.* 2000, vol. 48, No. 3, pp. 797-806.

Teicher, BA, et al., "Allosteric Effectors of Hemoglobin as Modulators of Chemotherapy and Radiation Therapy In Vitro and In Vivo", *Cancer Chemother. Pharmacol.*, 1998, vol. 42, pp. 24-30.

Tepper, J.E. and Shank, B. (writing Chairs), "Three-Dimensional Display in Planning Radiation Therapy: A Clinical Perspective", *Int. J. Rad. Oncol. Biol. Physics*. 1991, vol. 21, No. 1, pp. 79-89.

Urie, MM, et al., "The Role of Uncertainty Analysis in Treatment Planning", *Int. J. Radiat. Oncol. Biol. Phys.*, 1991, vol. 21, No. 1, pp. 91-107.

Vicini, FA, et al., "Dose-Volume Analysis for Quality Assurance of Interstitial Brachytherapy for Breast Cancer", *Int. J. Radiat. Oncol. Biol. Phys.*, 1999, vol. 45, No. 3, pp. 803-810.

Vicini, FA, et al., "Implementation of a 3D-Virtual Brachytherapy in the Management of Breast Cancer: a Description of a New Method of Interstitital Brachytherapy", *Int. J. Radiat. Oncol. Biol. Phys.*, 1998, vol. 40, No. 3, pp. 629-635.

Vicini, FA, et al., "Low-Dose-Rate Brachytherapy as the Sole Radiation Modality in the Management of Patients with Early-Stage Breast Cancer Treated with Breast-Concerving Therapy: Preliminary Results of a Pilot Trial", *Int. J. Radiat. Oncol. Biol. Phys.*, 1997, vol. 38, No. 2, pp. 301-310.

Williamson, JF, et al., "One-Dimensional Scatter-Subtraction Method for Brachytherapy Calculation Near Bounded Heterogeneities", *Med. Phys.*, Jan./Feb. 1993, vol. 20, No. 1, pp. 233-244.

Wong, JK, et al., "Conservative Management of Osteoradionecrosis", *Oral Surg. Oral Med. Pahol. Oral Pathol.*, Jul. 1997, vol. 84, No. 1, pp. 16-21.

Wong, JW, et al., "A New Approach to CT Pixel-Based Photon Dose Calculations in Heterogeneous Media", *Med. Phys.*, Mar./Apr. 1983, vol. 10, No. 2, pp. 199-208.

Wong, JW, et al., "Development of a Second-Generation Fiber-Optic On-Line Image Verification System", *Int. J. Radiat. Oncol. Biol. Phys.*, 1993, vol. 26, No. 2, pp. 311-320.

Wong, JW, et al., "Effect of Small Inhomogeneities on Dose in a Cobalt-60 Beam", *Med. Phys.*, Nov./Dec. 1981, vol. 8, No. 6, pp. 783-791.

Wong, JW, et al., "On Methods of Inhomogeneity Corrections for Photon Transport", *Med. Phys.*, Sep./Oct. 1990, vol. 17, No. 5, pp. 807-814.

Wong, JW, et al., "On-Line Image Verification in Radiation Therapy: An Early USA Experience", *Med. Prog. Through Technol.*, 1993, vol. 19, pp. 43-54.

Wong, JW, et al., "On-Line Radiotherapy Imaging with an Array of Fiber-Optic Image Reducers", *Int. J. Radiat. Oncol. Biol. Phys.*, Jun. 1990, vol. 18, No. 6, pp. 1477-1484.

Wong, JW, et al., "Portal Dose Images. I: Quantitative Treatment Plan Verification", *Int. J. Radiat. Oncol.Biol.Phys.*, Jun. 1990, vol. 18, No. 6, pp. 1455-1463.

Wong, JW, et al., "Reconsideration of the Power-Law (Batho) Equation for Inhomogeneity Corrections", *Med. Phys.*, Jul./Aug. 1982, vol. 9, No. 4, pp. 521-530.

Wong, JW, et al., "Second Scatter Contribution to Dose in Cobalt-60 Beam" *Med. Phys.*, Nov./Dec. 1981, vol. 8, No. 6, pp. 775-782.

Wong, JW, et al., "The Cumulative Verification Image Analysis Tool for Offline Evaluation of Portal Images", *Int. J. Radiat. Oncol.Biol. Phys.*, 1995, vol. 33, No. 5, pp. 1301-1310.

Wong, JW, et al., "The Use of Active Breathing Control (ABC) to Reduce Margin for Breathing Motion", *Int. J. Radiat. Oncol. Biol. Phys.*, 1999, vol. 44, No. 4, pp. 911-919.

Wong, JW, et al., "Treatment Verifications and Patient Dose Estimations Using Portal Dose Imaging" *Radiotherapy System Research* (Japan). 1988; vol. 5, No. 3, pp. 213-225.

Wong, JW., (writing chair), "Role of Inhomogeneity Corrections in 3D Photon Treatment Planning", *Int. J. Rad. Oncol. Biol. Physics.* 1991, vol. 21, No. 1, pp. 59-69.

Wu Y, Yan D, Sharpe MB, Miller B, Wong JW: "Implementing multiple static field delivery for intensity modulated beams", *Med. Phys.*, Nov. 2001, vol. 28, No. 11, pp. 2188-2197.

Yan D, Xu B, Lockman D, Kota K, Brabbins DS. Wong J, Martinez AA: "The influence of interpatient and intrapatient rectum variation on external beam treatment of prostate cancer", *Int. J. Radiat. Oncol. Biol. Phys.* 2001, vol. 51, No. 4, pp. 1111-1119.

Yan, D, et al., "A New Model for "Accept or Reject" Strategies in Off-Line and On-Line Megavoltage Treatment Evaluation", *Int. J. Radiat. Oncol. Biol. Phys.*, 1995, vol. 31, No. 4, pp. 943-952.

Yan, D, et al., "A Model to Accumulate Fractionated Dose in a Deforming Organ", *Int. J. Radiat. Oncol.Biol. Phys.*, 1999, vol. 44, No. 3, pp. 665-675.

Yan, D, et al., "Adaptive Radiation Therapy", *Phys. Med. Biol.*, 1997, vol. 42, pp. 123-132.

Yan, D, et al., "The Use of Adaptive Radiation Therapy to Reduce Setup Error: A Prospective Clinical Study", *Int. J. Radiat. Oncol. Biol. Phys.*, 1998, vol. 41, No. 3, pp. 715-720.

Yang, D., et al., "Adaptive Modification of Treatment Planning to Minimize the Deleterious effects of Treatment Setup Errors", *Int. J. Radiat. Oncol. Biol. Phys.*, 1997, vol. 38, No. 1, pp. 197-206.

Ying XG, et al., "Portal Dose Images. II: Patient Dose Estimation", *Int. J. Radiat. Oncol. Biol. Phys.*, Jun. 1990, vol. 18, No. 6, pp. 1465-1475.

Yu, C.X., Mackie, T.R. and Wong, J.W., "Photon Dose Calculation Incorporating Explicit Electron Transport", *Med. Phys.*, Jul. 1995, vol. 22, No. 7, pp. 1157-1165.

Yu, CX, et al., "A Method for Implementing Dynamic Photon Beam Intensity Modulation Using Independent Jaws and a Multileaf Collimator", *Phys. Med. Biol.*, 1995, vol. 40, pp. 769-787.

Yu, CX, et al., "A Multiray Model for Calculating Electron Pencil Beam Distribution", *Med. Phys.*, Sep./Oct. 1988, vol. 15, No. 5, pp. 662-671.

Yu, CX, et al., "Photon Dose Perturbations Due to Small Inhomogeneities", *Med. Phys.*, Jan./Feb. 1987, vol. 14, No. 1, pp. 78-83.

Jaffray et al., "Exploring 'Target of the Day' Strategies for a Medical Linear Accelerator with Conebeam-CT Scanning Capability," XIIth ICCR held in Salt Lake City, Utah, May 27-30, 1997, pp. 172-174.

Jaffray et al., "Conebeam Tomographic Guidance of Radiation Field Placement for Radiotherapy of the Prostate," Manuscript accepted for publication in the International Journal of Radiation Oncology, Biology, date unknown, 32 pages.

Jaffray et al., "Managing Geometric Uncertainty in Conformal Intensity-Modulated Radiation Therapy," Seminars in Radiation Oncology, vol. 9, No. 1, Jan. 1999 pp. 4-19.

Jaffray et al., "Performance of a Volumetric CT Scanner Based Upon a Flat-Panel Imager," SPIE Physics of Medical Imaging, vol. 3659, Feb. 1999, pp. 204-214.

Jaffray et al., "A Ghost Story: Spatio-temporal Response Characteristics of an Indirect-Detection Flat-Panel Imager," Med. Phys., vol. 26, No. 8, Aug. 1999, pp. 1624-1641.

Jaffray et al., "Cone-Beam Computed Tomography with a Flat-Panel Imager: Initial Performance Characterization," Submission to the Medical Physics Journal for publication on Aug. 1999, 36 pages.

Siewerdsen et al., "Cone-Beam Computed Tomography with a Flat-Panel Imager: Effects of Image Lag," Med. Phys., vol. 26, No. 12, Dec. 1999, pp. 2635-2647.

Jaffray et al., Cone-Beam CT: Applications in Image-Guided External Beam Radiotherapy and Brachytherapy, publication source unknown, date unknown, one page.

Siewerdsen et al., "Cone-Beam CT with a Flat-Panel Imager: Noise Consideration for Fully 3-D Computed Tomography," SPIE Physics of Medical Imaging, vol. 3336, Feb. 2000, pp. 546-554.

Jaffray et al., "Cone-Beam Computed Tomography with a Flat-Panel Imager: Initial Performance Characterization," Med. Phys., vol. 27, No. 6, Jun. 2000, pp. 1311-1323.

Siewerdsen et al., "Optimization of X-Ray Imaging Geometry (with Specific Application to Flat-Panel Cone-Beam Computed Tomography)," Non-Final Version of Manuscript to be published in Med. Phys., vol. 27, No. 8, Aug. 2000, pp. 1-12. Dieu et al., "Ion Beam Sputter-Deposited SiN/TiN Attenuating Phase-Shift Photoblanks," publication source and date unknown, 8 pages.

Jaffray et al., "Flat-Panel Cone-Beam CT for Image-Guided External Beam Radiotherapy," publication source unknown, Oct. 1999, 36 pages.

Cullity, B.D., "Elements of X-Ray Diffraction," Second Edition published by Addison-Wesley, Reading, MA, 1978, pp. 6-12.

\* cited by examiner

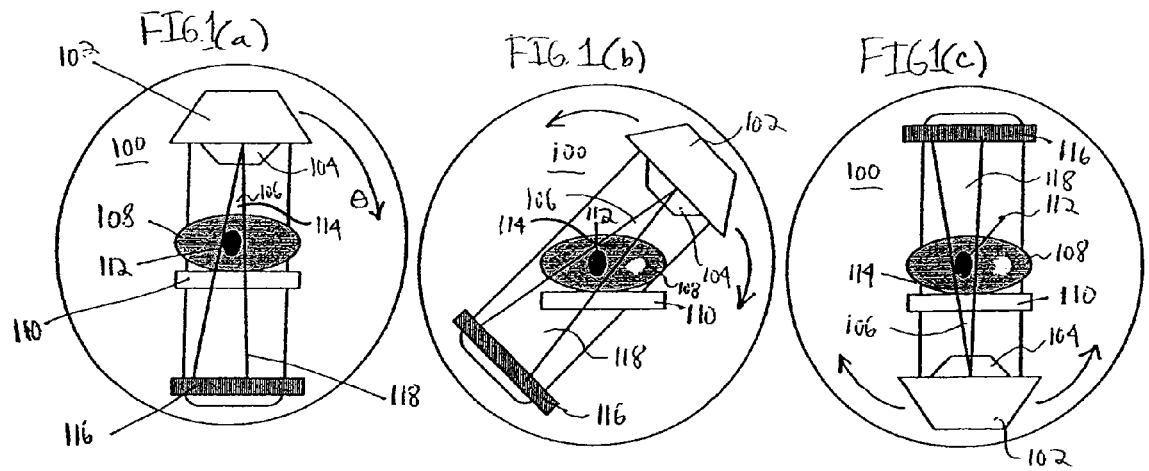
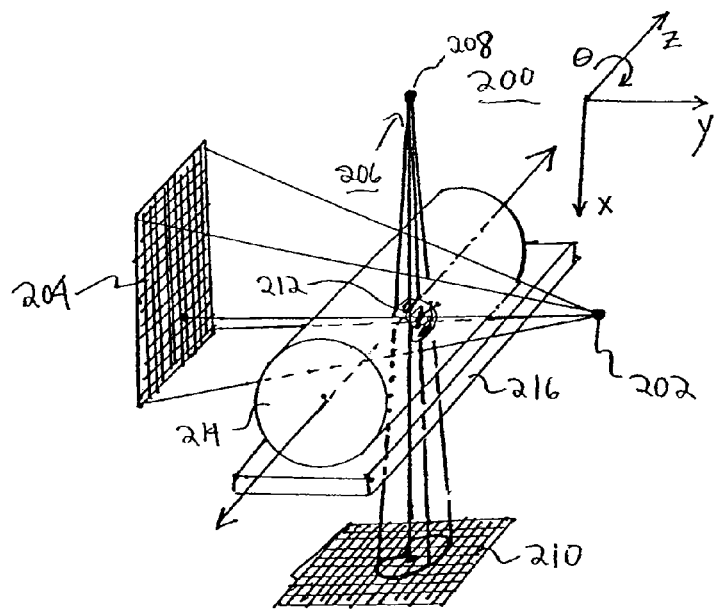
FIG. 2

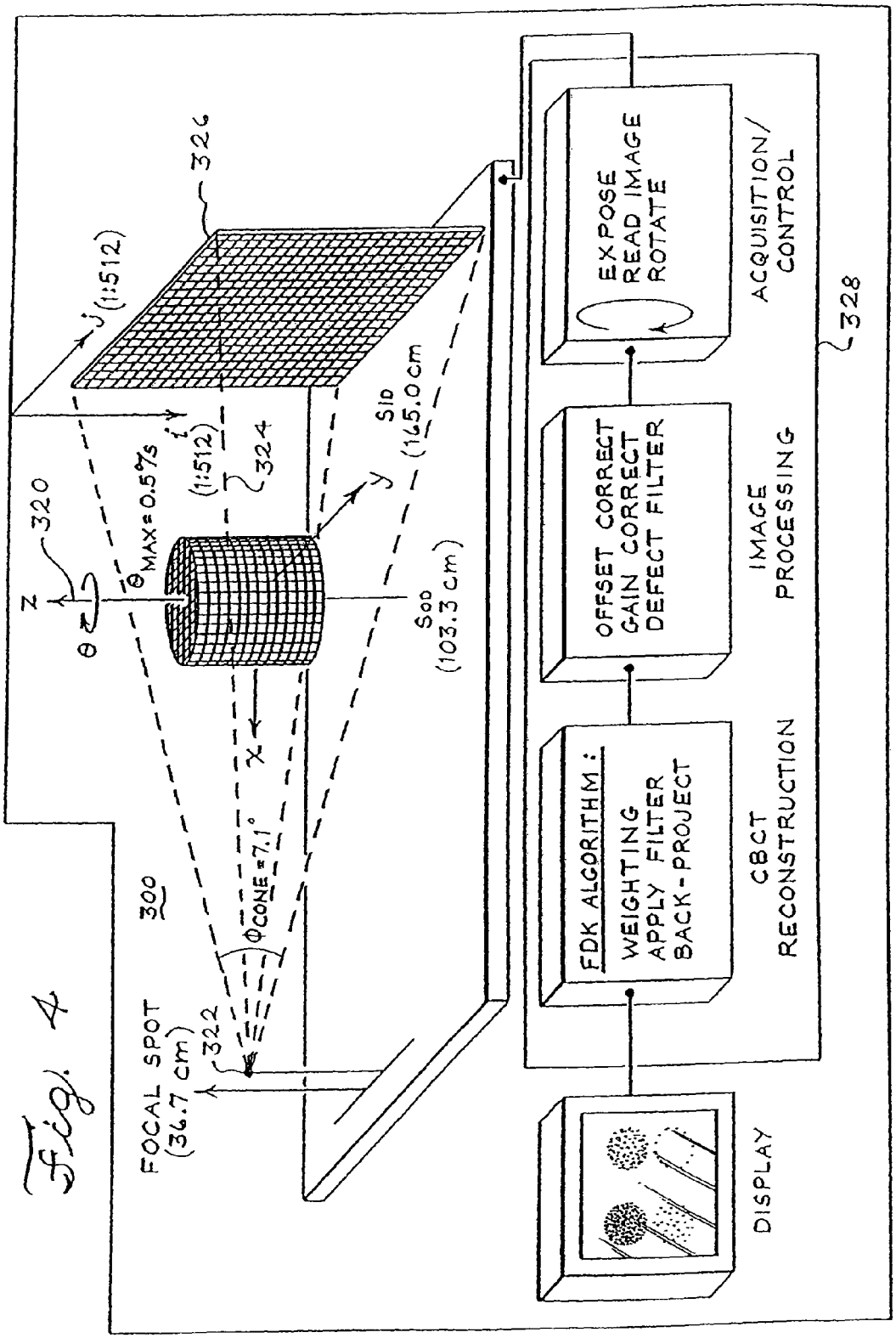

WATER CYLINDER
(UNIFORMITY, NOISE, NPS)

ELECTRON DENSITY PHANTHOM
(CONTRAST, CT LINEARITY)

WIRE PHANTHOM
(SPATIAL RESOLUTION, MTF)

EUTHENIZED WISTAR RAT
(SOFT TISSUE VISIBILITY, BONY DETAIL)

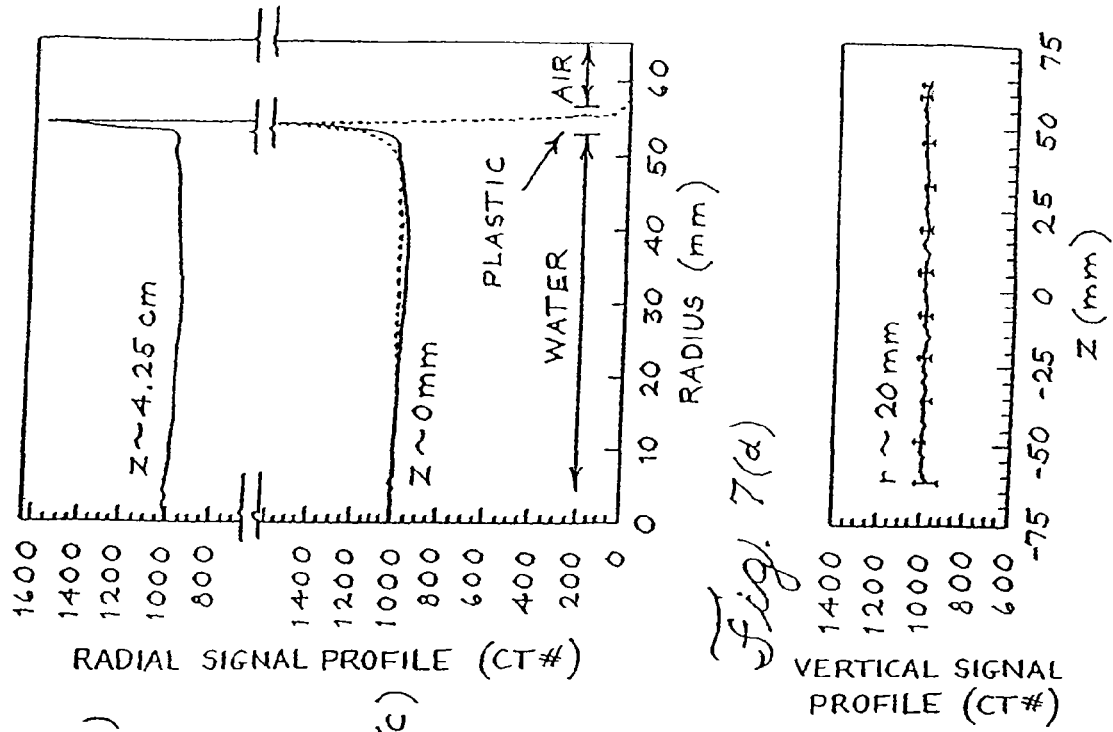
Fig. 7(a)
Fig. 7(c)
Fig. 7(b)
Fig. 7(d)
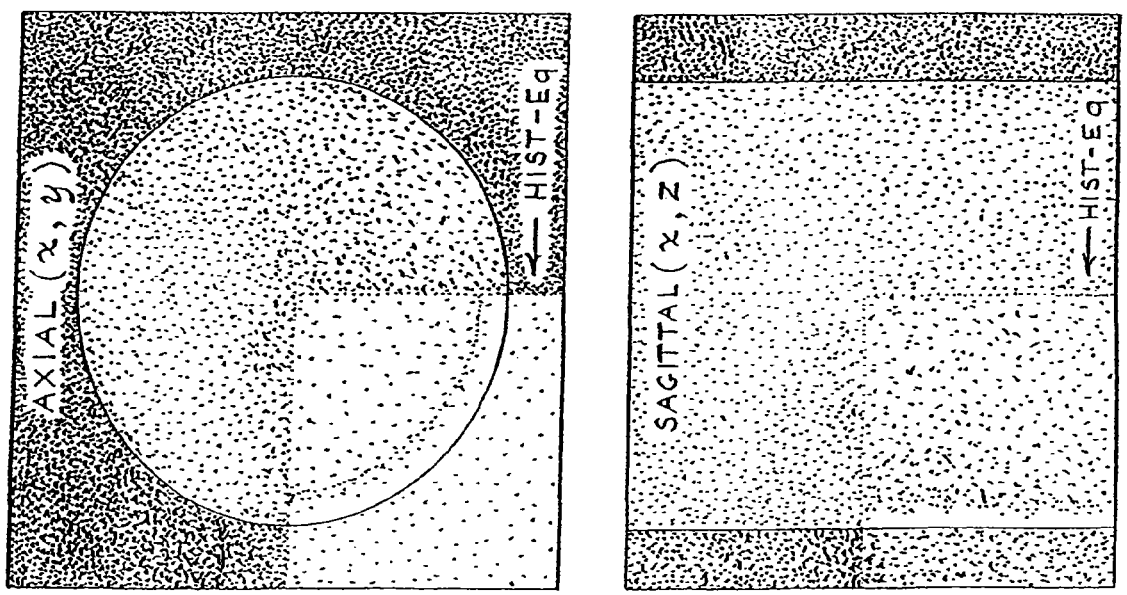

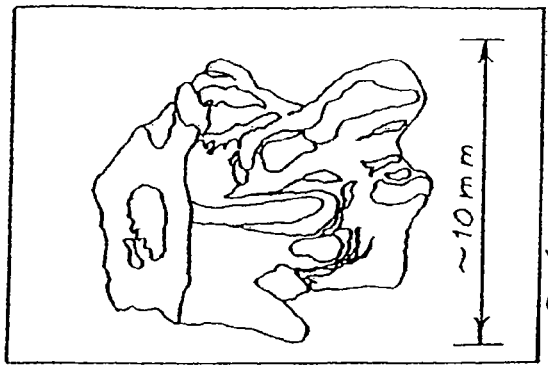
Fig. 14(d)
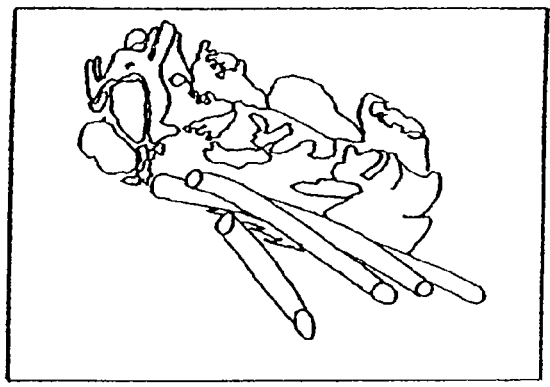
Fig. 14(c)
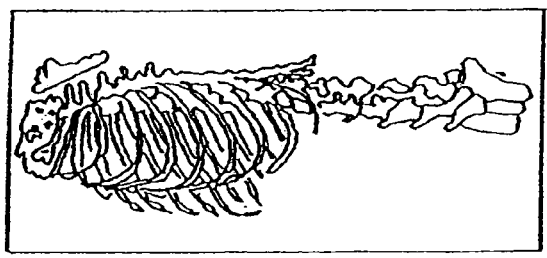
Fig. 14(b)
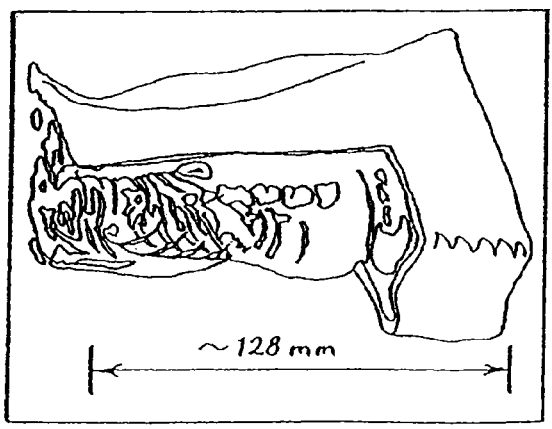
Fig. 14(a)
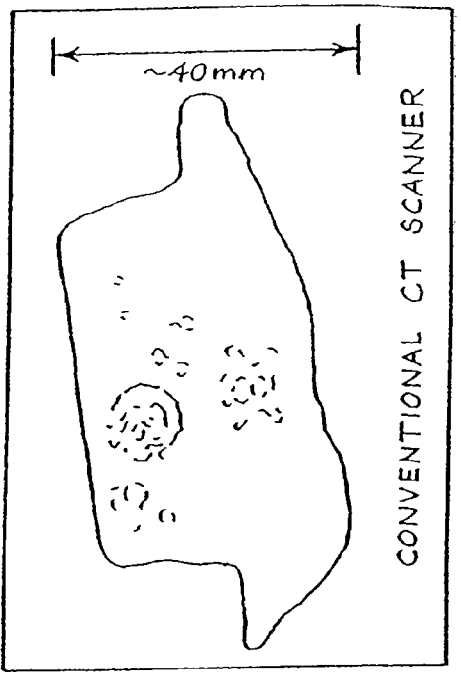
Fig. 15(a) CONVENTIONAL CT SCANNER
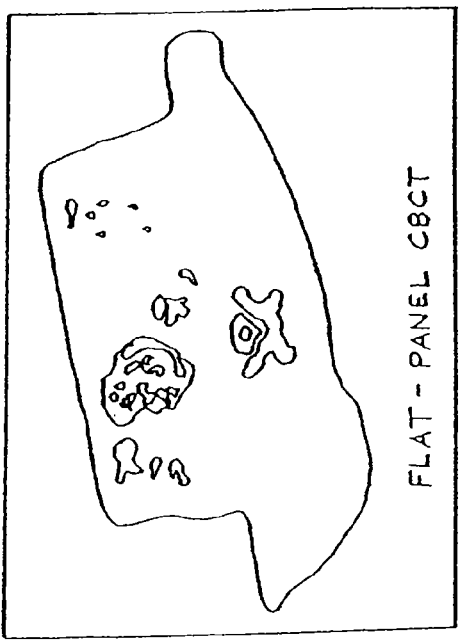
Fig. 15(b) FLAT-PANEL CBCT

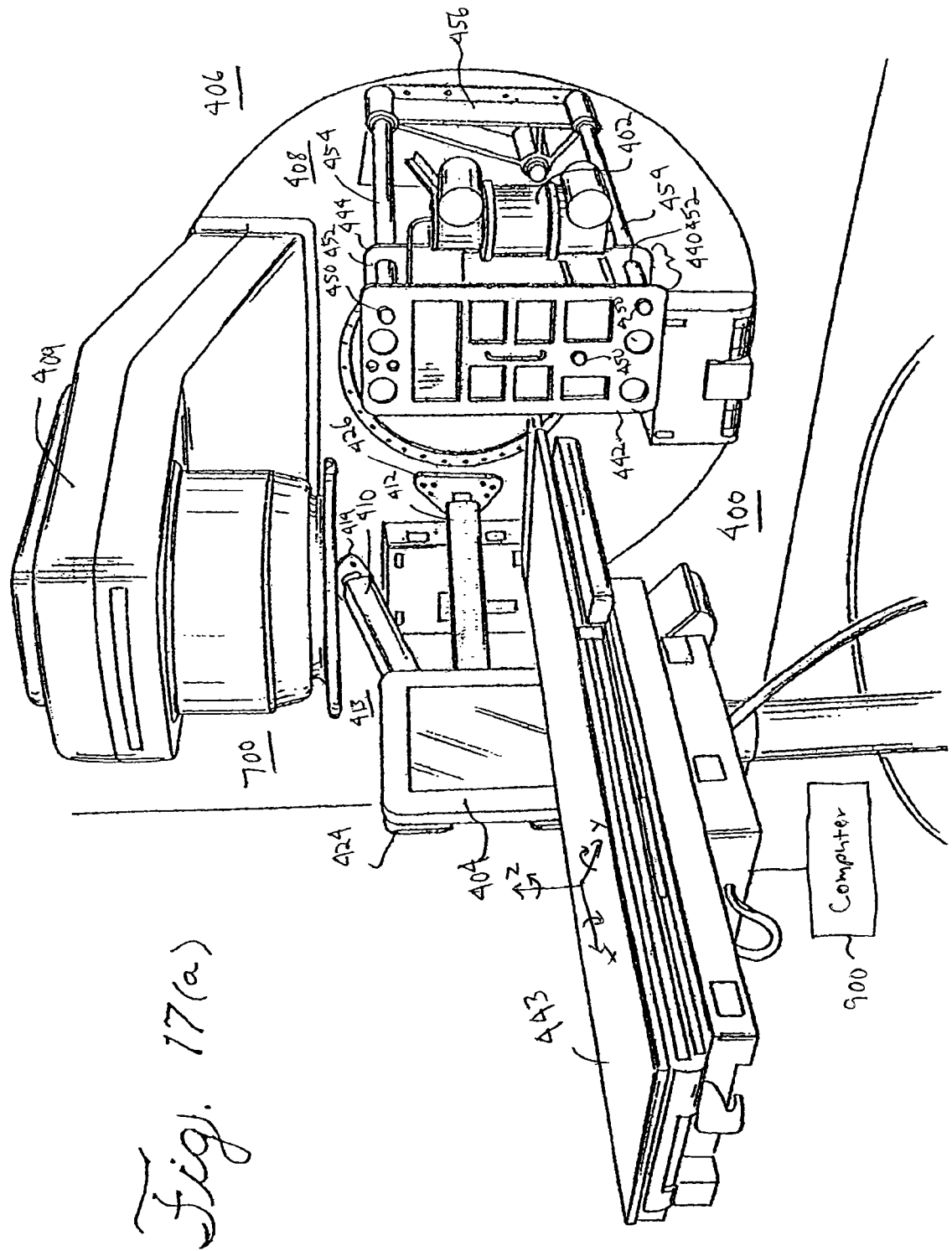

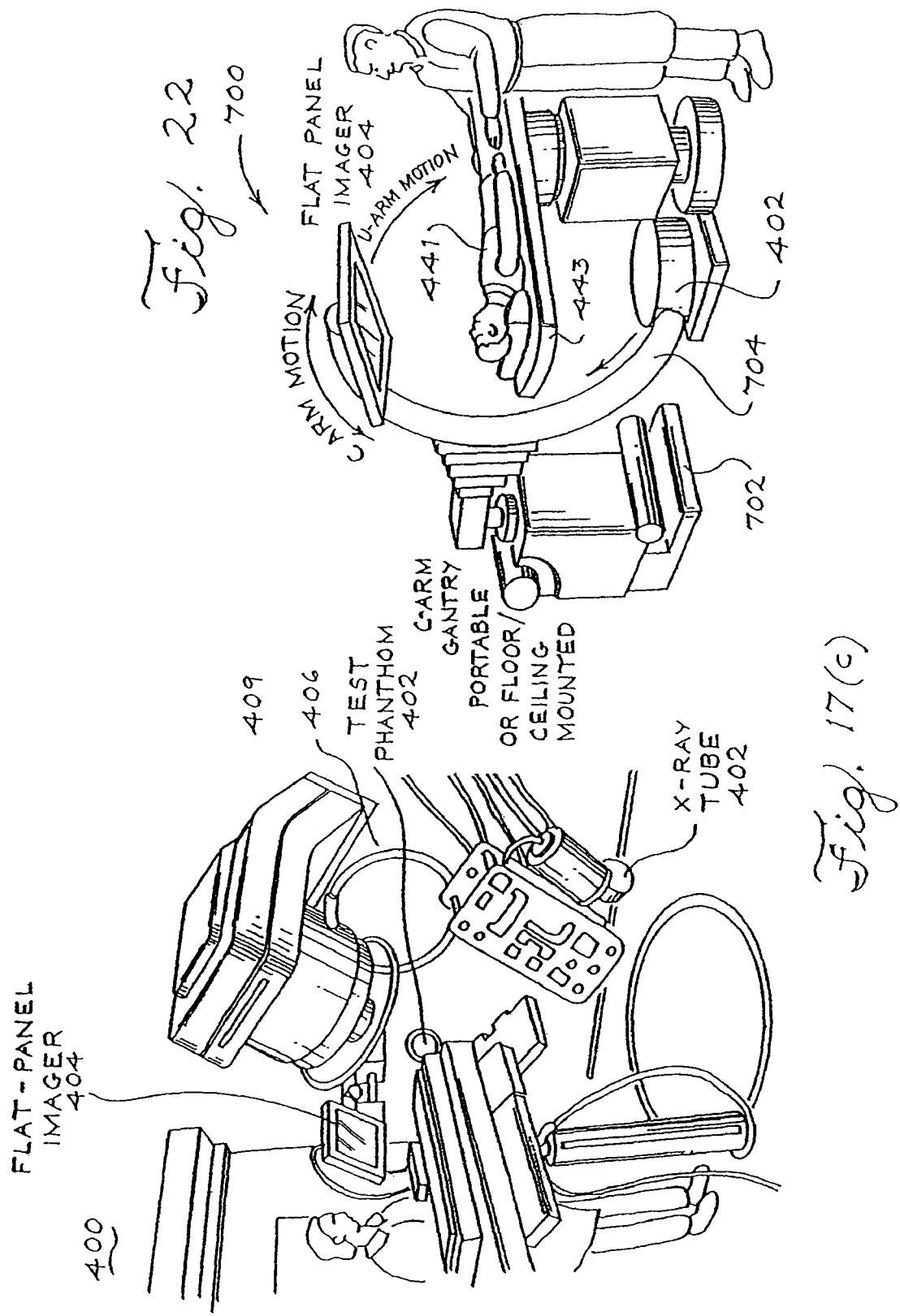

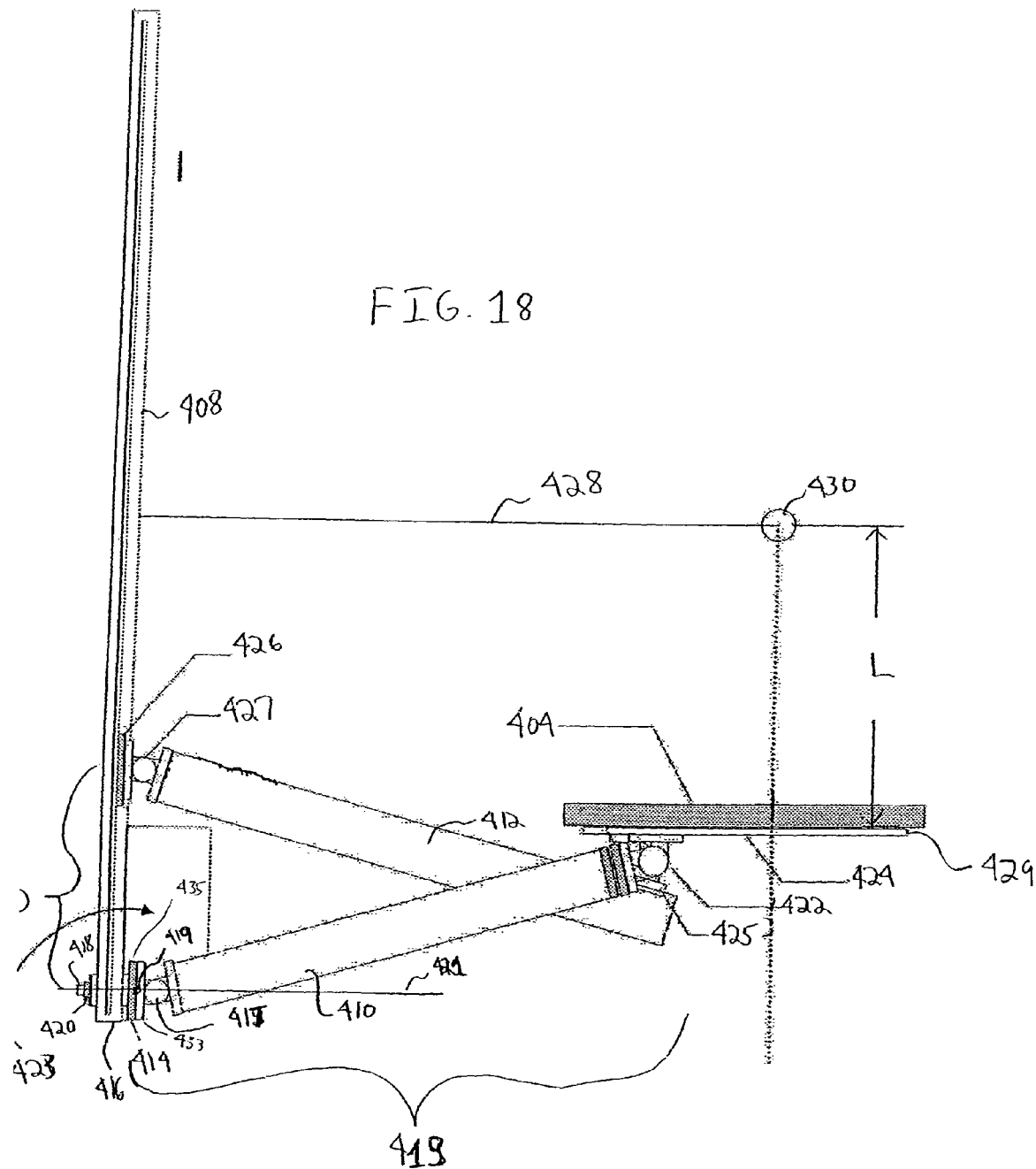

CONE BEAM COMPUTED TOMOGRAPHY WITH A FLAT PANEL IMAGER

This application is a continuation application of U.S. patent application Ser. No. 12/313,646, filed on Nov. 21, 2008 now U.S. Pat. No. 7,826,592, which is a divisional application of U.S. patent application Ser. No. 11/023,037, filed on Dec. 27, 2004, now U.S. Pat. No. 7,471,765, which is continuation application of U.S. patent application Ser. No. 09/788,335, filed on Feb. 16, 2001, now U.S. Pat. No. 6,842,502, the entire contents of each of which are incorporated herein by reference, and Applicants claim, under 35 U.S.C. §119(e), the benefit of priority of the filing date of Feb. 18, 2000, of U.S. Provisional Patent Application Ser. No. 60/183,590, filed on the aforementioned date, the entire contents of which are incorporated herein by reference.

The invention described in one or more claims were made with Government support under Grant No. DAMD17-98-1-8497 awarded by U.S. Army Medical Research Acquisition Activity. The Government has certain rights in the invention of such one or more claims.

BACKGROUND OF THE INVENTION

1. Field of the Invention

The present invention relates generally to a cone-beam computed tomography system and, more particularly, to a cone-beam computed tomography system that employs an amorphous silicon flat-panel imager for use in radiotherapy applications where the images of the patient are acquired with the patient in the treatment position on the treatment table.

2. Discussion of the Related Art

Radiotherapy involves delivering a prescribed tumorcidal radiation dose to a specific geometrically defined target or target volume. Typically, this treatment is delivered to a patient in one or more therapy sessions (termed fractions). It is not uncommon for a treatment schedule to involve twenty to forty fractions, with five fractions delivered per week. While radiotherapy has proven successful in managing various types and stages of cancer, the potential exists for increased tumor control through increased dose. Unfortunately, delivery of increased dose is limited by the presence of adjacent normal structures and the precision of beam delivery. In some sites, the diseased target is directly adjacent to radiosensitive normal structures. For example, in the treatment of prostate cancer, the prostate and rectum are directly adjacent. In this situation, the prostate is the targeted volume and the maximum deliverable dose is limited by the wall of the rectum.

In order to reduce the dosage encountered by radiosensitive normal structures, the location of the target volume relative to the radiation therapy source must be known precisely in each treatment session in order to accurately deliver a tumorcidal dose while minimizing complications in normal tissues. Traditionally, a radiation therapy treatment plan is formed based on the location and orientation of the lesion and surrounding structures in an initial computerized tomography or magnetic resonance image. However, the location and orientation of the lesion may vary during the course of treatment from that used to form the radiation therapy treatment plan. For example, in each treatment session, systematic and/or random variations in patient setup (termed interfraction setup errors) and in the location of the lesion relative to surrounding anatomy (termed interfraction organ motion errors) can each change the location and orientation of the lesion at the time of treatment compared to that assumed in the radiation therapy treatment plan. Furthermore, the location and orientation of the lesion can vary during a single treatment session (resulting in intrafraction errors) due to normal biological processes, such as breathing, peristalsis, etc. In the case of radiation treatment of a patient's prostate, it is necessary to irradiate a volume that is enlarged by a margin to guarantee that the prostate always receives a prescribed dose due to uncertainties in patient positioning and daily movement of the prostate within the patient. Significant dose escalation may be possible if these uncertainties could be reduced from current levels (.about.10 mm) to 2-3 mm.

Applying large margins necessarily increases the volume of normal tissue that is irradiated, thereby limiting the maximum dose that can be delivered to the lesion without resulting in complication in normal structures. There is strong reason to believe that increasing the dose delivered to the lesion can result in more efficacious treatment. However, it is often the case that the maximum dose that can be safely delivered to the target volume is limited by the associated dose to surrounding normal structures incurred through the use of margins. Therefore, if one's knowledge of the location and orientation of the lesion at the time of treatment can be increased, then margins can be reduced, and the dose to the target volume can be increased without increasing the risk of complication in normal tissues.

A number of techniques have been developed to reduce uncertainty associated with systematic and/or random variations in lesion location resulting from interfraction and intrafraction errors. These include patient immobilization techniques (e.g., masks, body casts, bite blocks, etc.), off-line review processes (e.g., weekly port films, population-based or individual-based statistical approaches, repeat computerized tomography scans, etc.), and on-line correction strategies (e.g., pre-ports, MV or kV radiographic or fluoroscopic monitoring, video monitoring, etc.).

It is believed that the optimum methodology for reducing uncertainties associated with systematic and/or random variations in lesion location can only be achieved through using an on-line correction strategy that involves employing both on-line imaging and guidance system capable of detecting the target volume, such as the prostate, and surrounding structures with high spatial accuracy.

An on-line imaging system providing suitable guidance has several requirements if it is to be applied in radiotherapy of this type. These requirements include contrast sensitivity sufficient to discern soft-tissue; high spatial resolution and low geometric distortion for precise localization of soft-tissue boundaries; operation within the environment of a radiation treatment machine; large field-of-view (FOV) capable of imaging patients up to 40 cm in diameter; rapid image acquisition (within a few minutes); negligible harm to the patient from the imaging procedure (e.g., dose much less than the treatment dose); and compatibility with integration into an external beam radiotherapy treatment machine.

Several examples of known on-line imaging systems are described below. For example, strategies employing x-ray projections of the patient (e.g., film, electronic portal imaging devices, kV radiography/fluoroscopy, etc.) typically show only the location of bony anatomy and not soft-tissue structures. Hence, the location of a soft-tissue target volume must be inferred from the location of bony landmarks. This obvious shortcoming can be alleviated by implanting radio-opaque markers on the lesion; however, this technique is invasive and is not applicable to all treatment sites. Tomographic imaging modalities (e.g., computerized tomography, magnetic resonance, and ultrasound), on the other hand, can provide information regarding the location of soft-tissue target volumes. Acquiring computerized tomography images at the time of treatment is possible, for example, by incorporating a computerized tomography scanner into the radiation therapy environment (e.g., with the treatment table translated between the computerized tomography scanner gantry and the radiation therapy gantry along rails) or by modifying the treatment machine to allow computerized tomography scanning. The former approach is a fairly expensive solution, requiring the installation of a dedicated computerized tomography scanner in the treatment room. The latter approach is possible, for example, by modifying a computer tomography scanner gantry to include mechanisms for radiation treatment delivery, as in systems for tomotherapy. Finally, soft-tissue visualization of the target volume can in some instances be accomplished by means of an ultrasound imaging system attached in a well-defined geometry to the radiation therapy machine. Although this approach is not applicable to all treatment sites, it is fairly cost-effective and has been used to illustrate the benefit of on-line therapy guidance.

As illustrated in FIGS. 1(a)-(c), a typical radiation therapy system 100 incorporates a 4-25 MV medical linear accelerator 102, a collimator 104 for collimating and shaping the radiation field 106 that is directed onto a patient 108 who is supported on a treatment table 110 in a given treatment position. Treatment involves irradiation of a lesion 112 located within a target volume with a radiation beam 114 directed at the lesion from one or more angles about the patient 108. An imaging device 116 may be employed to image the radiation field 118 transmitted through the patient 108 during treatment. The imaging device 116 for imaging the radiation field 118 can be used to verify patient setup prior to treatment and/or to record images of the actual radiation fields delivered during treatment. Typically, such images suffer from poor contrast resolution and provide, at most, visualization of bony landmarks relative to the field edges.

Another example of a known on-line imaging system used for reducing uncertainties associated with systematic and/or random variations in lesion location is an X-ray cone-beam computerized tomography system. Mechanical operation of a cone beam computerized tomography system is similar to that of a conventional computerized tomography system, with the exception that an entire volumetric image is acquired through a single rotation of the source and detector. This is made possible by the use of a two-dimensional (2-D) detector, as opposed to the 1-D detectors used in conventional computerized tomography. There are constraints associated with image reconstruction under a cone-beam geometry. However, these constraints can typically be addressed through innovative source and detector trajectories that are well known to one of ordinary skill in the art.

As mentioned above, a cone beam computerized tomography system reconstructs three-dimensional (3-D) images from a plurality of two-dimensional (2-D) projection images acquired at various angles about the subject. The method by which the 3-D image is reconstructed from the 2-D projections is distinct from the method employed in conventional computerized tomography systems. In conventional computerized tomography systems, one or more 2-D slices are reconstructed from one-dimensional (1-D) projections of the patient, and these slices may be "stacked" to form a 3-D image of the patient. In cone beam computerized tomography, a fully 3-D image is reconstructed from a plurality of 2-D projections. Cone beam computerized tomography offers a number of advantageous characteristics, including: formation of a 3-D image of the patient from a single rotation about the patient (whereas conventional computerized tomography typically requires a rotation for each slice); spatial resolution that is largely isotropic (whereas in conventional computerized tomography the spatial resolution in the longitudinal direction is typically limited by slice thickness); and considerable flexibility in the imaging geometry. Such technology has been employed in applications such as micro-computerized tomography, for example, using a kV x-ray tube and an x-ray image intensifier tube to acquire 2-D projections as the object to be imaged is rotated, e.g., through 180.degree. or 360.degree. Furthermore, cone beam computerized tomography has been used successfully in medical applications such as computerized tomography angiography, using a kV x-ray tube and an x-ray image intensifier tube mounted on a rotating C-arm.

The development of a kV cone-beam computerized tomography imaging system for on-line tomographic guidance has been reported. The system consists of a kV x-ray tube and a radiographic detector mounted on the gantry of a medical linear accelerator. The imaging detector is based on a low-noise charge-coupled device (CCD) optically coupled to a phosphor screen. The poor optical coupling efficiency (~10.sup.-4) between the phosphor and the CCD significantly reduces the detective quantum efficiency (DQE) of the system. While this system is capable of producing cone beam computerized tomography images of sufficient quality to visualize soft tissues relevant to radiotherapy of the prostate, the low DQE requires imaging doses that are a factor of 3-4 times larger than would be required for a system with an efficient coupling (e.g. ~50% or better) between the screen and detector.

Another example of a known auxiliary cone beam computerized tomography imaging system is shown in FIG. 2. The auxiliary cone beam computerized tomography imaging system 200 replaces the CCD-based imager of FIGS. 1(a)-(c) with a flat-panel imager. In particular, the imaging system 200 consists of a kilovoltage x-ray tube 202 and a flat panel imager 204 having an array of amorphous silicon detectors that are incorporated into the geometry of a radiation therapy delivery system 206 that includes an MV x-ray source 208. A second flat panel imager 210 may optionally be used in the radiation therapy delivery system 206. Such an imaging system 200 could provide projection radiographs and/or continuous fluoroscopy of the lesion 212 within the target volume as the patient 214 lies on the treatment table 216 in the treatment position. If the geometry of the imaging system 200 relative to the system 206 is known, then the resulting kV projection images could be used to modify patient setup and improve somewhat the precision of radiation treatment. However, such a system 200 still would not likely provide adequate visualization of soft-tissue structures and hence be limited in the degree to which it could reduce errors resulting from organ motion.

Accordingly, it is an object of the present invention to generate KV projection images in a cone beam computerized tomography system that provide adequate visualization of soft-tissue structures so as to reduce errors in radiation treatment resulting from organ motion.

BRIEF SUMMARY OF THE INVENTION

One aspect of the present invention regards a radiation therapy system that includes a radiation source that moves about a path and directs a beam of radiation towards an object and a cone-beam computer tomography system. The cone-beam computer tomography system includes an x-ray source that emits an x-ray beam in a cone-beam form towards an object to be imaged and an amorphous silicon flat-panel imager receiving x-rays after they pass through the object, the imager providing an image of the object. A computer is connected to the radiation source and the cone beam computerized tomography system, wherein the computer receives the image of the object and based on the image sends a signal to the radiation source that controls the path of the radiation source.

A second aspect of the present invention regards a method of treating an object with radiation that includes moving a radiation source about a path, directing a beam of radiation from the radiation source towards an object and emitting an x-ray beam in a cone beam form towards the object. The method further includes detecting x-rays that pass through the object due to the emitting an x-ray beam with an amorphous silicon flat-panel imager, generating an image of the object from the detected x-rays and controlling the path of the radiation source based on the image.

Each aspect of the present invention provides the advantage of generating KV projection images in a cone beam computerized tomography system that provide adequate visualization of soft-tissue structures so as to reduce errors in radiation treatment resulting from organ motion.

Each aspect of the present invention provides an apparatus and method for improving the precision of radiation therapy by incorporating a cone beam computerized tomography imaging system in the treatment room, the 3-D images from which are used to modify current and subsequent treatment plans.

Each aspect of the present invention represents a significant shift in the practice of radiation therapy. Not only does the high-precision, image-guided system for radiation therapy address the immediate need to improve the probability of cure through dose escalation, but it also provides opportunity for broad innovation in clinical practice.

Each aspect of the present invention may permit alternative fractionation schemes, permitting shorter courses of therapy and allowing improved integration in adjuvant therapy models.

Each aspect of the present invention provides valuable imaging information for directing radiation therapy also provides an explicit 3-D record of intervention against which the success or failure of treatment can be evaluated, offering new insight into the means by which disease is managed.

Additional objects, advantages and features of the present invention will become apparent from the following description and the appended claims when taken in conjunction with the accompanying drawings.

BRIEF DESCRIPTION OF THE DRAWINGS

FIGS. 1(a)-(c) schematically show the geometry and operation of a conventional radiation therapy apparatus;

FIG. 2 schematically shows a perspective view of a known radiation therapy apparatus including an auxiliary apparatus for cone beam computerized tomography imaging;

FIG. 4 is a schematic illustration of the geometry and procedures of the cone beam computerized tomography system shown in FIG. 3;

FIGS. 7(a)-7(d) depict uniformity of response of the cone beam computerized tomography system of the present invention, including axial and sagittal slices through volume images of a uniform water bath, radial profiles, and a vertical signal profile, respectively;

FIGS. 14(a)-14(d) show volume renderings of cone beam computerized tomography images of the euthanized rat shown in FIG. 6(d) illustrating the degree of spatial resolution achieved in delineating structures of the vertebra, including volume renderings with axial and sagittal cut planes showing the skeletal anatomy along with soft-tissue structures of the abdomen, volume renderings with axial and sagittal cut planes, window to show skeletal features only, a magnified view of a region of the spine and ribs of the rat, and a magnified view of a part of two vertebra, respectively;

FIGS. 15(a)-15(b) depict the axial images of euthanized rat shown in FIG. 6(d) obtained from the cone beam computerized tomography system of the present invention and a conventional computerized tomography scanner, respectively;

FIGS. 17(a)-(e) are diagrammatic views of several angular orientations of a wall-mounted cone beam computerized tomography system employing a flat-panel imager, according to a second embodiment of the present invention;

FIG. 18 shows a side view of the cone beam computerized tomography system of FIG. 17 when employing a first embodiment of a support for a flat-panel imager according to the present invention;

FIG. 22 is a diagrammatic view of a portable cone beam computerized tomography system employing a flat-panel imager according to fifth embodiment of the present invention;

PREFERRED EMBODIMENTS OF THE INVENTION

Figure 3:
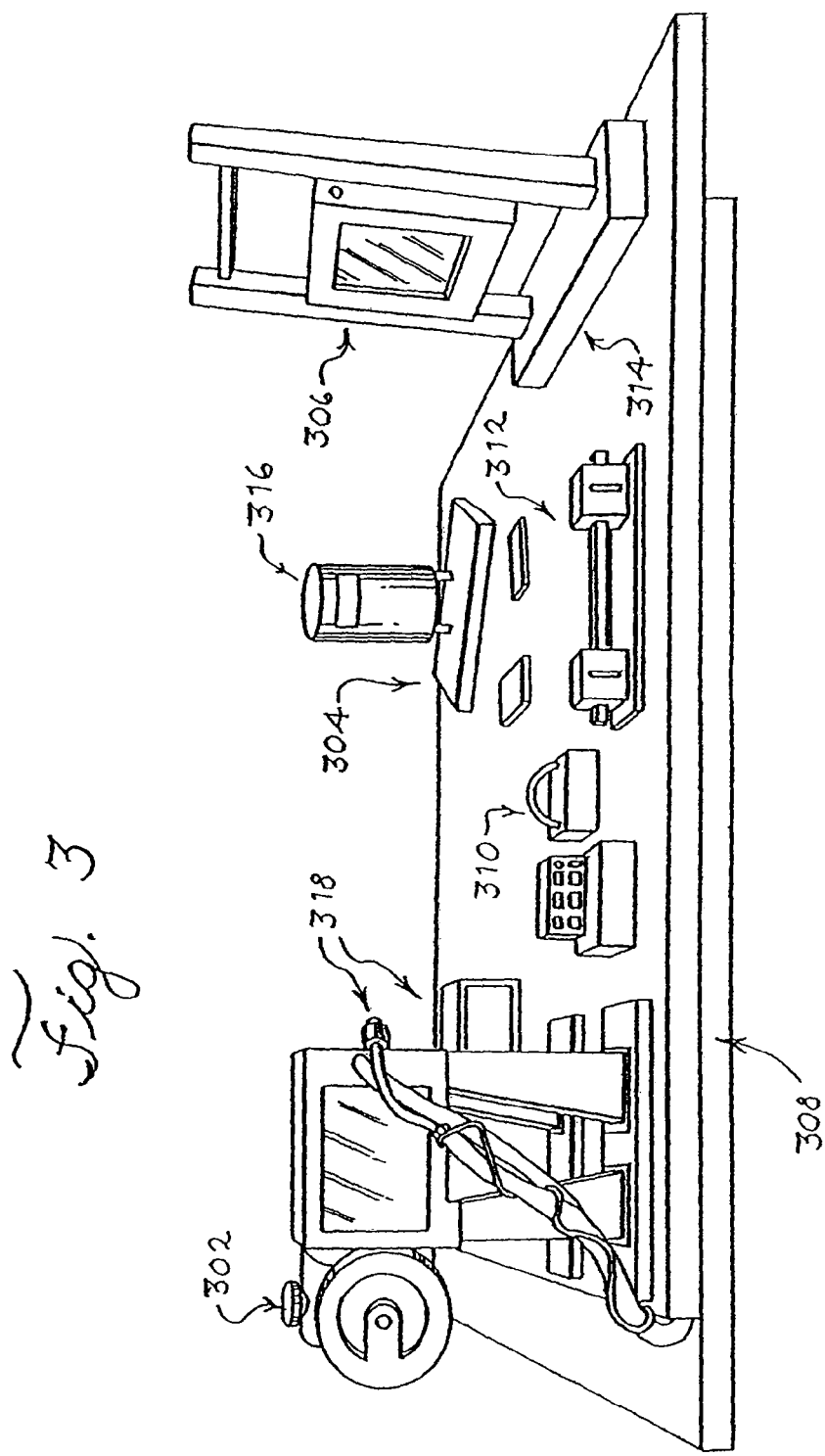
FIG. 3 is a diagrammatic view of a bench-top cone beam computerized tomography system employing a flat-panel imager, according to a first embodiment of the present invention.

A bench-top cone beam computerized tomography (CBCT) system 300 is shown in FIG. 3, according to an embodiment of the present invention. The CBCT system 300 was constructed to mimic the geometry of the CBCT scanner currently installed on a linear accelerator, with a source-to-axis distance of 1000 mm and a source-detector distance of 1600 mm. The primary components of the system 300 include an x-ray tube 302, a rotation stage 304 and flat-panel imager (FPI) 306. These components are rigidly mounted to an optical bench 308. The relative position of these components is controlled by three translation stages, including an object stage 310, a yobject stage 312 and a yimage stage 314, which are used during initial setup to accurately determine and control the imaging geometry. The cone beam computerized tomography system 300 generates images of an object 316, identified throughout as a phantom, mounted on the rotation stage 304. Each stage 310, 312 and 314 contains a home or limit switch, and the imaging geometry is referenced to the location of these switches with a reproducibility of .+-.0.01 mm. The specific geometries used in the discussion herein are shown in FIG. 4, and are set to simulate the imaging geometry that would be implemented for a cone beam computerized tomography system incorporated on a radiotherapy treatment machine. Table 1 below shows the parameters of the system 300.

A set of alignment lasers 318 allow visualization of the axis of rotation 320 and the source plane perpendicular to the axis of rotation 320 and intersects focal spot 322 of the x-ray source or tube 302. The axis of rotation 320 is positioned such that it intersects the central ray 324 between the focal spot 322 and the detector plane 326 (+0.01 mm). The flat plane imager 326 is positioned such that the piercing point (i.e., the intersection of the central ray and the image plane) is centered on the imaging array (i.e., between columns #256 and #257, .+-.0.01 mm), with a quarter-pixel offset applied to give improved view sampling for cone beam computerized tomography acquisitions in which the object 316 is rotated through 360.degree. The stage 310 is controlled manually by means of a positioning micrometer. The source-to-object (SOD) and source-to-image (SID) distances were measured to within .+-.0.5 mm and give an objection magnification of 1.60, equal to that of the imaging system on the linear accelerator. The cone angle for this geometry is –7.1.

Radiographic exposures used in the acquisition procedure are produced under computer control with a 300 kHU x-ray tube 302, such as General Electric Maxi-ray 75 and a 100 kW generator, such as the General Electric MSI-800. The tube 302 has a total minimum filtration of 2.5 mm A1, with an additional filtration of 0.127 mm Cu to further harden the beam, and a nominal focal spot size of 0.6 mm. The 100 kV beam is characterized by first and second HVLs of 5.9 and 13.4 mm A1, respectively. The accelerating potential of the generator was monitored over a one-week period and was found to be stable to within .+-.1%. All exposures were measured using an x-ray multimeter, such as the RTI Electronics, Model PMX-III with silicon diode detector.

The exposures for the cone beam computerized tomography acquisitions are reported in terms of exposure to air at the axis of rotation 320 in the absence of the object 316. The same method of reporting exposure can be used for the images acquired on the conventional scanner. For the conventional scanner, the exposure per unit charge is measured with the gantry rotation disabled and the collimators set for a 10 mm slice thickness, thereby guaranteeing complete coverage of the silicon diode. The exposure per unit charge at 100 kVp was 9.9 mR/mAs and 14.9 mR/mAs for the bench-top and conventional scanners, respectively.

The flat panel imager 306 can be the EG&G Heimann Optoelectronics (RID 512-400 AO) that incorporates a 512.times.512 array of a-Si:H photodiodes and thin-film transistors. The electromechanical characteristics of the imager are shown in Table 1. The flat plane imager 306 is read-out at one of eight present frame rates (up to 5 frames per second) and operates asynchronously of the host computer 328 schematically shown in FIG. 4. The analog signal from each pixel is integrated by ASIC amplifiers featuring correlated double-sampling noise reduction circuitry. Digitization is performed at 16 bit resolution. The values are transferred via an RS-422 bus to a hardware buffer in the host computer 328. The processor in the host computer 328 is interrupted when a complete frame is ready for transfer to host memory.

TABLE 1

| CBCT Characteristic | Value |
|---|---|
| Acquisition Geometry | |
| Source-axis-distance ($S_{AD}$) | 103.3 cm |
| Source-imager-distance ($S_{ID}$) | 165.0 cm |
| Cone angle | 7.1° |
| Maximum angular rotation rate | 0.5°/sec |
| Field of view (FOV) | 12.8 cm |
| X-ray Beam/Exposure Characteristics | |
| Beam energy | 100 kVp |
| Added filtration | 1.5 mm A1 + 0.129 mm Cu |
| Beam quality | $HVL_1$ = 5.9 MM A1 |
| | $HVL_2$ = 13.4 MM A1 |

TABLE 1-continued

| CBCT Characteristic | Value |
|---|---|
| Scatter-to-primary ratio | 0.18, 1:5 (11 cm object) |
| Frame time | 6.4 sec |
| Tube output at (SAD) | 9.34 mR/mAs |
| Exposure rate (at SID) | 3.65 mR/mAs |
| Flat-Panel Imager | |
| Designation | RID 512-400 AO |
| Array format | 512 × 512 pixels |
| Pixel pitch | 400 μm |
| Area | ~20.5 20.5 cm² |
| Pixel fill factor | 0.80 |
| Photodiode charge capacity | ~62 Pc |
| ASIC amplifier charge capacity | ~23 pC |
| ASIC amplifier noise | ~12,700 e |
| ADC bit-depth | 16 bit |
| TFT thermal noise (on) | ~1800 e |
| Photodiode Shot Noise (1 fps) | ~1200 e |
| Digitazation noise | ~630 e |
| Nominal frame rate | 0.16 fps |
| Maximum frame rate | 5 fps |
| X-ray converter | 133 mg/cm₂Gd₂O₂S:Tb |
| Acquisition Procedure | |
| Number of projections | 300 |
| Angular increment | 1.2° |
| Total rotation angle | 360° |
| Maximum angular rotation rate | $05^D$/s |
| Reconstruction Parameters | |
| Reconstruction matrix | 561 × 561 × (1-512), 281 × 281 × (1-500) |
| Voxel size | 0.25 × 0.25 × 0.25 mm2, 0.5 × 0.5 × 0.25 |
| W. parameter | 1.60 |
| γ, cutoff frequency modification | 1.0 |
| α, modified Hamming filter parameter | 0.50 |
| Range of convolution | ±25 mm |

The cone-beam scanning procedure includes a repeated sequence of radiographic exposure, array readout, and object rotation. The timing of this procedure is driven by the asynchronous frame clock of the flat plane imager readout electronics. A conservative frame time of 6.4 s was used. Between the periodic frame transfers from the flat plane imager 306, the host computer advances the motorized rotation stage 304 and triggers the x-ray generator or tube 302. The rotor of the x-ray tube 302 remains spinning throughout the scanning procedure. The control software allows the operator to specify the number of frames between exposures. This was designed as a mechanism to investigate methods of reducing the amount of lag in sequential projections. The detector signal from a group of nine pixels in the bare-beam region of the flat plane imager 306 is monitored to measure and verify the stability of each radiographic exposure. Exposures outside tolerance are trapped and repeated at the same projection angle. Each projection image is written to hard disk between frame transfer and motor rotation. After the projections are acquired, a set of flood and dark field images (20 each) are collected to construct gain and offset images for flat-field processing of the projection images.

In addition to gain and offset corrections, median filtration (3.times.3) is performed using a pre-constructed map of unstable pixels. Finally, the signal in each projection is normalized to account for small variations in x-ray exposure, this is performed using a cluster of nine pixels in the periphery of the detector well outside the objects shadow.

A volumetric computerized tomography data set is reconstructed from the projections using a filtered back-projection technique. The filter used in the reconstruction is constructed using Webb's three-parameter formula. The parameters and their corresponding values are shown in Table 1. In the current configuration, the reconstruction field of vision is limited to a 12.4 cm diameter cylinder, approximately 12.1 cm in length; the lateral extent of objects to be reconstructed must lie well-within this cylinder. The voxel values in the resulting volumetric data sets are scaled linearly to produce a mean CT number of zero in air and 1000 in water. The time required to filter (100 element kernel) and back-project a single projection (512.times.512) on to a 281.times.281.times.500 voxel data set was 1 minute and 21 seconds.

Figure 5A:
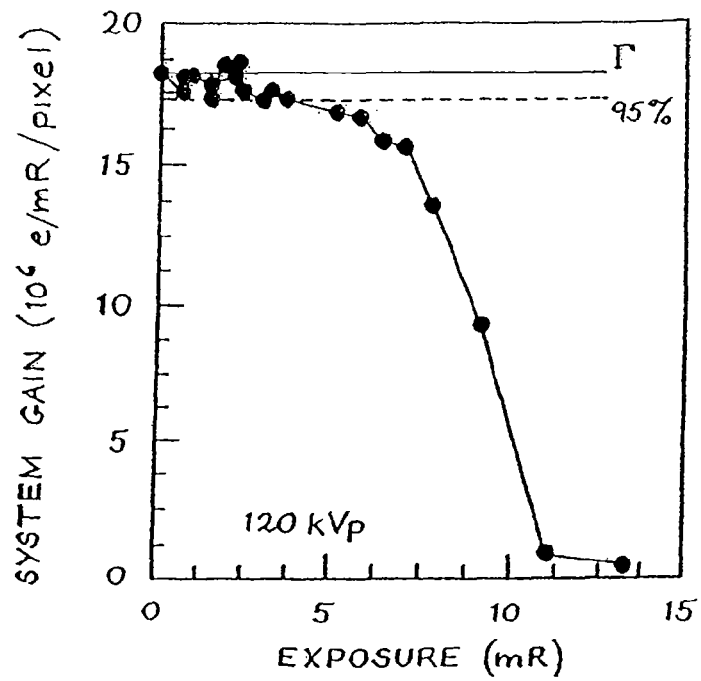
FIGS. 5(a)-5(d) are graphs depicting the fundamental performance characteristics of the flat-panel imager used in the cone beam computerized tomography system of FIG. 3.

The basic signal and noise characteristics of the flat plane imager 306 were measured. The detector gain and linearity are presented in FIG. 5(a). For an x-ray beam energy of 120 kVp, the detector gain was measured to be 18.2.times.10.sup.5 e/mR/pixel (17.8.times.10.sup.6 e/mR at 100 kVp). The detector exhibits excellent linearity with exposure up to 50% of its sensitive range (5 mR). The various additive electronic noise sources and their magnitudes are listed in Table 1. The total additive electronic noise is found to depend upon frame time, ranging from 13,300 e at a frame time of 200 ms to 22,500 e at a frame time of 25.6 s. The amplifier noise (12,700 e) is the dominant component at high frame rates. The significance of amplifier noise on the zero-frequency detective quantum efficiency (DQE) was studied using a cascaded system model that analyzes signal and noise propagation in the FPI 306.

Figure 5B:
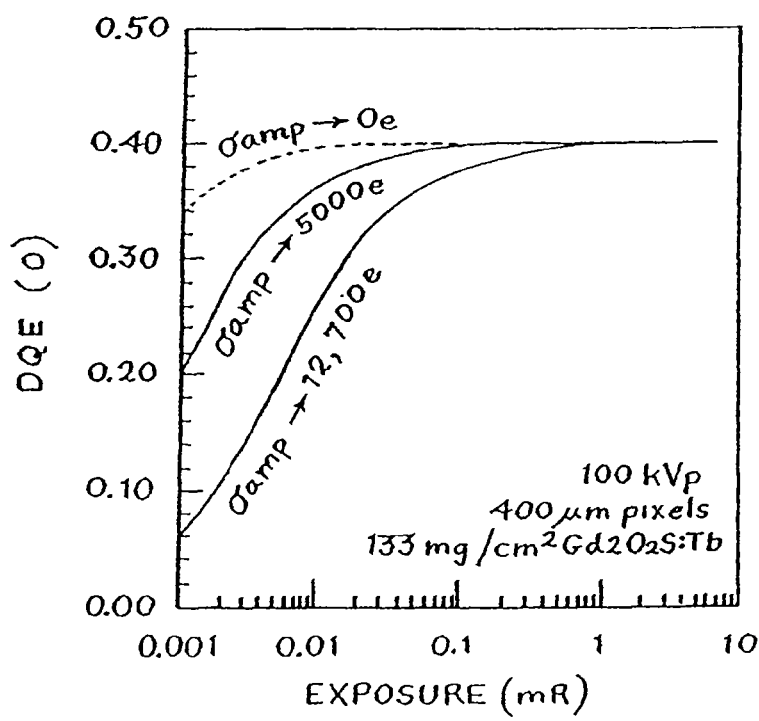

FIG. 5(b) shows the dependence of detective quantum efficiency on exposure for the RID 512-400AO, as well as for two hypothetical imagers with reduced amplifier noise. The primary quantum efficiency for the detector is approximately 0.57; losses due to energy absorption noise and additive sources reduce the detective quantum efficiency to .about.0:41 for exposures above 1 mR. For exposures below 0.1 mR, the detective quantum efficiency falls rapidly for amplifier noise values comparable to that found in the EG&G detector. Thus for thicker/denser objects [e.g., a pelvis (.about.30 cm water)] resulting in significantly reduced dose to the detector (e.g., .about.0.001 mR) improvements in amplifier noise (and/or x-ray converter, e.g. CsI;TI) will significantly improve detective quantum efficiency.

Figure 5C:
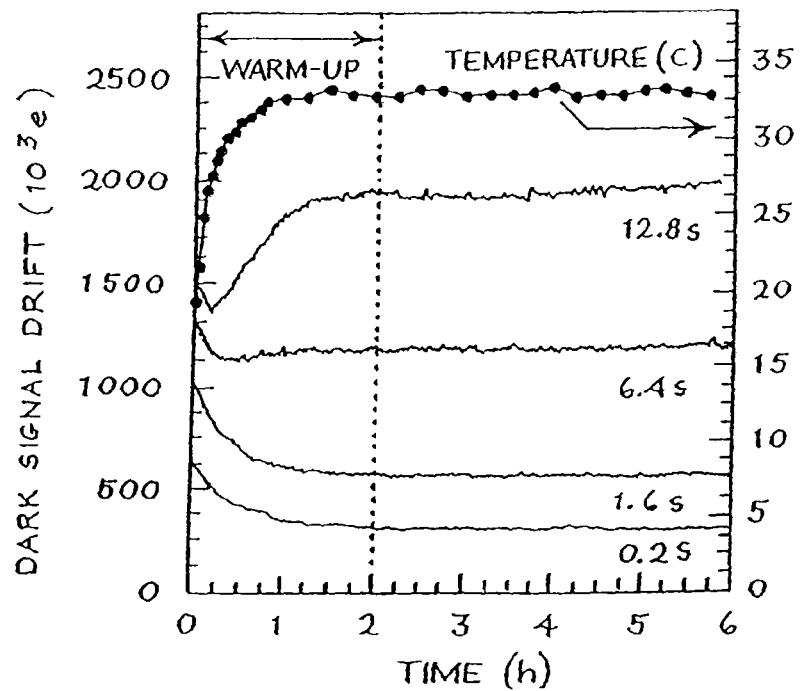

The temporal stability of the detector dark signal is presented in FIG. 5(c). This plot corresponds to a selected group of 'typical' pixels. The dark signal drifts significantly during the first 2 h of operation, which correlates with the change in temperature within the flat panel imager enclosure. After the temperature has stabilized, the dark signal also stabilizes. Based on these results, all cone beam computerized tomography scans were performed after the array had been powered-on for at least 2 hours. In some regions of the array, the dark signal does not stabilize, even after thermal equilibrium. It is assumed that these regions are the result of variations in the array manufacturing process.

Figure 5D:
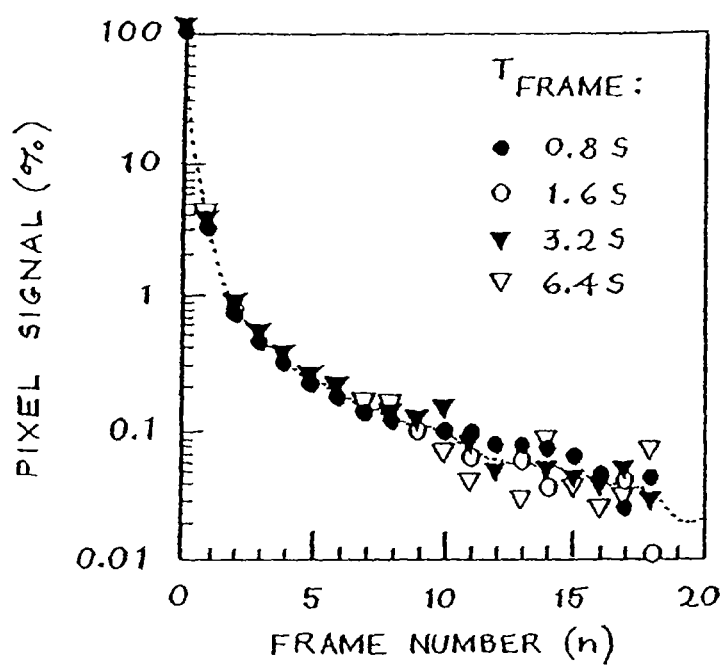

The continuously changing scene in computerized tomography necessitates a detector with rapid read out and minimal temporal blurring, or 'lag.' Such characteristics have been measured using a short, intra-frame, x-ray exposure. FIG. 5(d) shows the pixel signal following a single radiographic exposure applied within the acquisition period of frame number 0. Subsequent frames exhibit lag signal ranging from .about.4% to .about.0.04% for frame members 1 through 9. It is interesting and important to note that the lag demonstrates a dependence not upon frame time, but also exclusively upon the number of frames.

Prior to reconstruction, the projections are corrected for stationary pixel-to-pixel variations in offset and gain. Defective pixels with significant variations in dark field signal or with aberrant signal response are median filtered. The resulting projections are padded by an additional 128 columns prior to reconstruction. The value of the padded pixels is set row-by-row to the average of the 7 pixels at the periphery of the array. Finally, to account for small variations in x-ray tube output, the signal in each projection is normalized using signal measured from the bare-beam monitors pixels mentioned above (nine pixels). The pre-construction processing can be performed on a 250 MHz UltraSparc processor, such as the Enterprise 450, Sun Microsystems, Sunnyvale, Calif.

Feldkamp's filtered back-projection algorithm can be used to reconstruct the data set. Images are reconstructed on a Cartesian matrix of voxels 561.times.561.times.N, where the number of slices, N, depends on the object of interest. The voxel size used in these reconstructions was typically 0.25.times.0.25.times.0.25 mm. The filtering used in the reconstruction follows the formalism of Webb. Table 1 contains the three parameters that specify the filter used in these investigations. Upon completion of the reconstruction, an offset and scale parameters are constant for a 9 mm set of reconstruction and acquisition parameters. The reconstruction of the volumetric cone beam computerized tomography data sets is also performed on the UltraSparc system.

The uniformity of response of the imaging system 300 over the three-dimensional (3-D) field-of-view (FOV) was studied by imaging a cylindrical water bath [110 mm diameter]. Scans of the same phantom were also acquired on the conventional scanner. The response was examined along both radial and vertical profiles through the reconstructed volume.

The noise in reconstructed images of the water bath was studied as a function of x-ray exposure. Images were acquired at exposures of 131, 261, 653, 1310, 3260, and 6530 mR. The images were reconstructed on a 561.times.561.times.11 matrix with voxel dimensions of 0.25 mm on a side. For all reconstructions, the reconstruction filter was fixed at the parameters specified in Table 1. Varying these parameters can have a significant effect on the noise characteristics of the reconstructed images. The noise characteristics of these image sets were analyzed by analysis of the standard deviation in CT number in 5.times.5.times.1 regions throughout the data set, and by calculation of the noise power spectrum (NPS) from the 3D data sets. Both methods of analysis were performed as a function of exposure. The relative stability of the noise was assessed by examining the uniformity of the noise over the entire 3-D data set. These results indicated that the noise characteristics of the data set vary only slightly with location. These initial results lend support to the application of noise power analysis, since stability is a necessary condition for proper interpretation of noise power results.

The noise-power spectrum (NPS) was analyzed from the volumetric data by extension of methods employed for analysis of known 2-D projection images. The volume data was normalized such that the mean CT number within the water cylinder was 1000. A tetragonal region (256.times.256.times.20 voxels) within the water cylinder was cropped from the volume, and a small number of voxel defects (always<1%) were 3.times.3 median filtered. In order to obtain a convergent 2-D central slice of the 3-D Fourier transform, the twenty slices were averaged along the z-direction, and it was found that averaging more slices did not affect the noise-power spectrum, i.e., the data was convergent. A background slice formed from the average of 81 slices in a separate scan was subtracted in order to reduce background trends. Low-frequency trends were further reduced by subtraction of a planar fit to the data, yielding a 2-D zero-mean realization. The two-dimensional Fast Fourier Transform (FFT) was computed from ensembles of sixteen 64.times.64 non-overlapping regions within the realization, and the results were averaged. The results were normalized to account for voxel size and for average in z, and the volume under the noise-power spectrum was compared to the square of the standard deviation. The resulting noise-power spectrum represents a central slice in the (u.sub.x u.sub.y) domain, i.e., the Fourier counterpart to the (x, y) domain. Strips along the u, axis were extracted in order to show 1-D power spectra, NPS(u.sub.x), e.g., are various exposure levels.

Figure 6A:
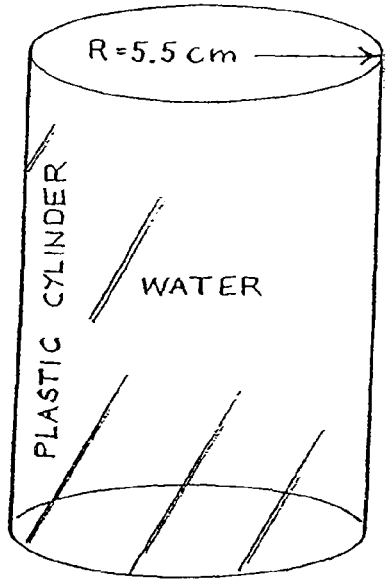
FIGS. 6(a)-6(d) show various objects used in tests to investigate the performance of the cone beam computerized tomography system of the present invention, including a uniform water cylinder, six low-contrast inserts in a water bath, a steel wire under tension with a water bath, and an euthanized rat, respectively.
Figure 6B:
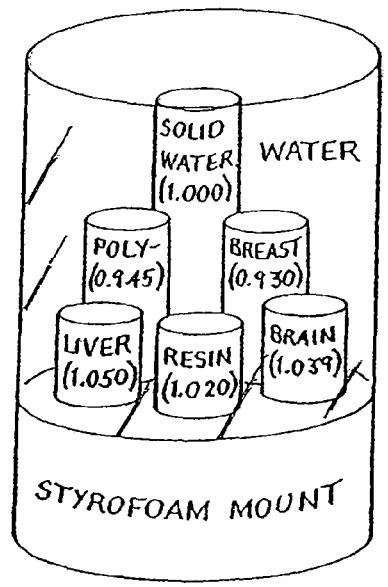

The noise characteristics of the cone beam computerized tomography system 300 were compared to those of the conventional computerized tomography scanner. To allow meaningful comparison, the two systems must demonstrate identical response over the range of signal variation. The response was tested by scanning an electron density phantom (shown in FIG. 6(b)) with the two systems. Seven inserts with coefficients near that of water were inserted into a 110 mm diameter water bath. The inserts are taken from the RMI electron density phantom having nominal CT numbers. In FIG. 6(b), clockwise from the top: CT Solid Water (CT#1001), BR-SRI Breast (CT#945), BRN-SR2 Brain (CT#1005), C133 Resin Mix (CT#1002), LV1 Liver (CT#1082), and, Polyethylene (CT#897). This phantom was imaged at equivalent exposure and kVp with both the cone beam computerized tomography system 300 and the conventional scanner.

The attenuation coefficients (relative to water) reported by the cone beam computerized tomography system 300 were compared to those reported by the conventional scanner. A first-order fit to the measured data was calculated to determine the relative linearity of the two systems. The noise characteristics of the conventional scanner were also measured using the water cylinder test phantom described above images were acquired at 100 kVp with a slice thickness of 1 mm at four different exposure levels (743, 1490, 2970, and 5940 mR). Three images were acquired at each exposure level. Reconstructions were performed on the conventional scanner using the 'High Res Head (#1 H)', 'Standard Head (#2)', and 'Smooth Abdomen (#3)' filters. The noise analysis was identical to that applied to the cone beam computerized tomography data sets. In order to compare noise results measured on each system, analysis of the cone beam computerized tomography data sets was repeated wherein the cone beam computerized tomography data was first average over 2.times.2.times.4 voxels to yield an equivalent (0.5.times.0.5.times.1 mm) voxel size to that given by the conventional scanner.

Figure 6C:
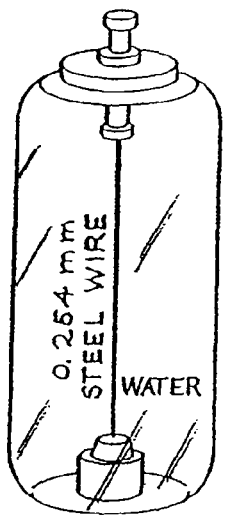

The spatial frequency transfer characteristics of the cone beam computerized tomography system 300 were measured using a wire test object, shown in FIG. 6(c). The test object consists of a 0.254 mm diameter steel wire suspended in a 50 mm diameter water bath. The phantom was imaged on the cone beam computerized tomography system 300 (at 100 kVp) with the wire centered on the axis of rotation 320 and with the wire located −30 mm off-axis. The resulting images were reconstructed on a high resolution reconstruction grid of 0.1.times.0.1.times.0.25 mm.sup.3 using the filter described in Table 1. Six adjacent slices (each 0.25 mm thick) were averaged to generate a low noise point spread function (PSF). Orthogonal slices through the 2-D modulation transfer function (MTF) were calculated by first computing the Radon transform of the point spread function (i.e., integrating along either the x or y axis), and then calculating the 1-D Fourier transform. Each 1-D profile was normalized to unity area. A correction was applied to compensate for the finite diameter of the steel wire. For purposes of comparison, the same tests were performed on the conventional scanner at 100 kVp for a slice thickness of 1.5 mm. Images were reconstructed using three different reconstruction filters ["High Res Head (#1 H)," "Standard Head (#2)," and "Smooth Abdomen (#3)"].

The relative imaging performance of the cone beam computerized tomography system 300 and the conventional scanner were compared using phantoms and small animals. A simple comparison in soft-tissue detectability was performed with the phantom shown in FIG. 6(b). The proximity in CT number between each of the six cylinders makes this phantom a useful test object for examining contrast sensitivity and soft-tissue detectability, images were acquired of the phantom with both the cone beam computerized tomography system 300 and conventional scanners. Multiple high-resolution cone beam computerized tomography slices were averaged to produce an equivalent slice thickness to that used on the conventional scanner (1.5 mm). Equivalent exposure (2980 mR) and kVp were used in the two different scans.

Figure 6D:
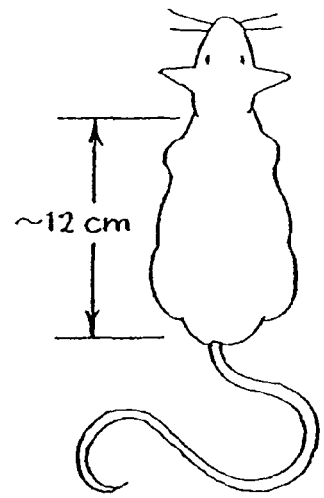

A second test of soft-tissue sensitivity was performed by imaging a laboratory rat that had been euthanized for other purposes, FIG. 6(d). A scanning procedure identical to that described above was used, delivering an in-air, on-axis exposure of 2980 mR at 100 kVp for both systems. The resulting 3-D data was reconstructed at voxel sizes of $0.25 \times 0.25 \times 0.25$ mm$^3$. The subject was also scanned on the conventional computerized tomography scanner at a slice thickness of 1.5 mm. This scan delivered the same imaging dose as was delivered by the cone beam computerized tomography system 300. For purposes of intercomparison, six slices from the cone beam computerized tomography data set were averaged to produce a slice thickness equivalent to that of the conventional scan. The imagers were displayed at comparable window and level to allow comparison.

The uniformity of response of the cone beam computerized tomography scanner shown in shown in FIGS. 7(a)-7(d). Axial and sagittal slices through the cone beam computerized tomography 3-D data set are shown. The images demonstrate a relatively uniform response over the entire field of view of the system. A slight non-uniformity of approximately 20 CT numbers (2%) is visible in the histogram equalized regions of the images. This non-uniformity appears as a combined cupping and capping artifact. The radial profile (FIG. 7(c)) illustrates this point further by comparing to the results obtained from the conventional scanner (dotted line). An internal check of the reconstruction process using simulated projection data demonstrates that the non-uniformity is an artifact of the reconstruction process and is dependent upon the choice of filtering parameters. Apart from the non-uniformity inherent to the reconstruction, the response of the cone beam computerized tomography system 300 is highly uniform, particularly along the z-dimension.

Figure 8C:
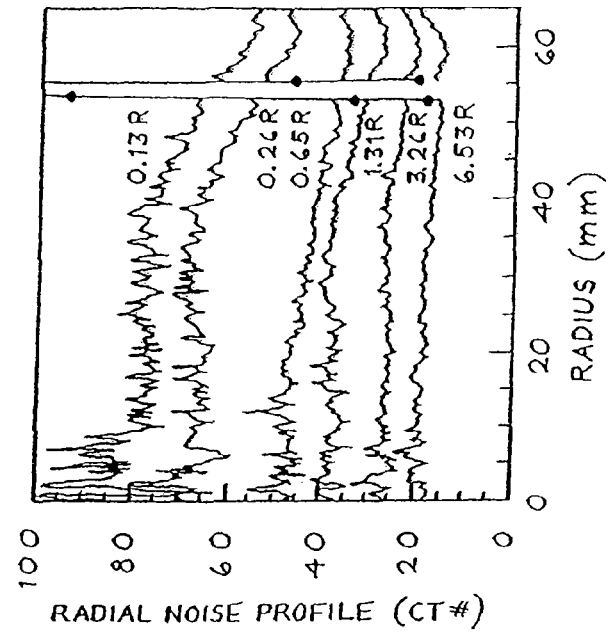
FIGS. 8(a)-8(d) illustrate the noise characteristics of the cone beam computerized tomography system of the present invention, including axial and sagittal noise images from volume reconstructions of a uniform water bath, radial noise profiles, and vertical nose profiles, respectively.
Figure 8D:
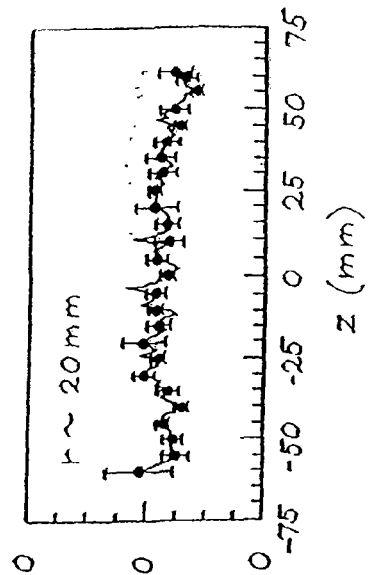
Figure 8A:
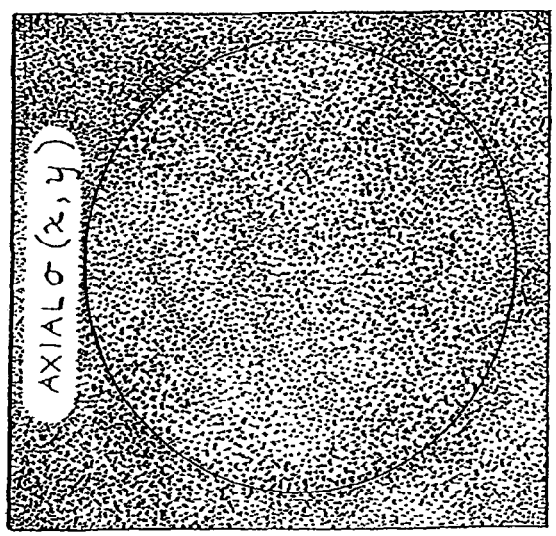
Figure 8B:
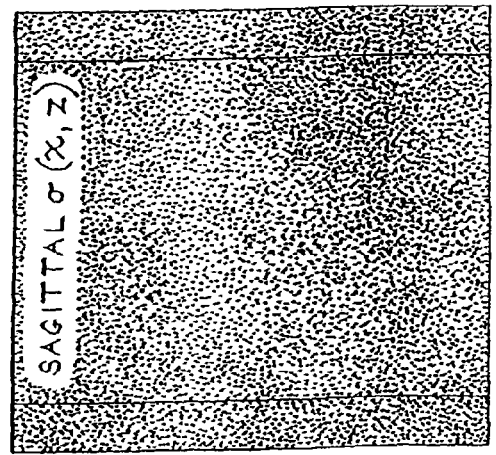

In addition to demonstrating uniformity of system response, the images in FIG. 7 also demonstrate uniform noise characteristics with few artifacts. This is the case for the full range of exposures studied. The magnitude and uniformity of the noise is demonstrated in FIGS. 8(a)-8(d). The noise varies to a slight degree along the radial axis and to a negligible degree along the vertical axis. A slight dependence on radial position is expected due to the differences in transmission across the cylindrical water bath. FIG. 8(c) also presents the measured dependence of noise on exposure [also shown below, in relation to FIG. 9(b)]. Overall, the cone beam computerized tomography system 300 is capable of achieving a noise level of approximately 20 CT numbers for an in-air exposure of 6560 mR at isocenter.

Figure 9A:
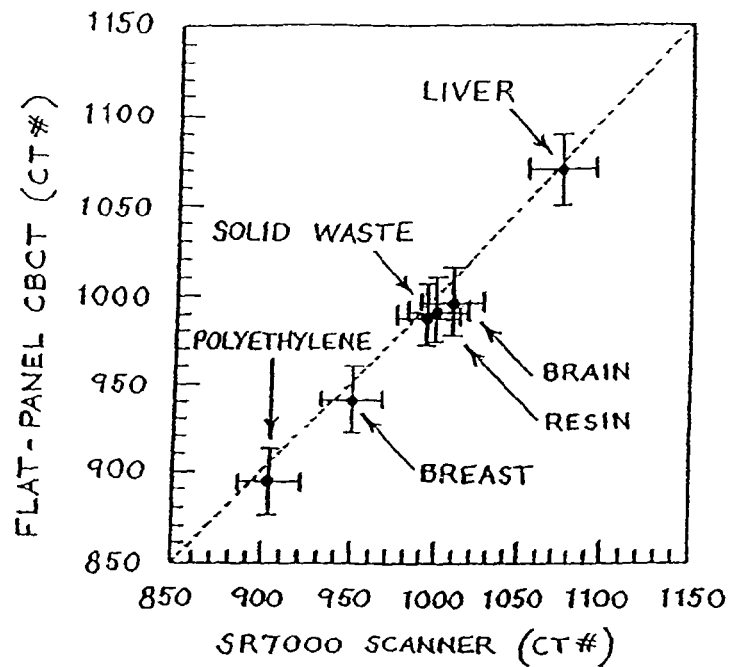
FIGS. 9(a)-9(b) depict response linearity and voxel noise, respectively, for the cone beam computerized tomography system of the present invention and a conventional computerized tomography scanner.
Figure 9B:
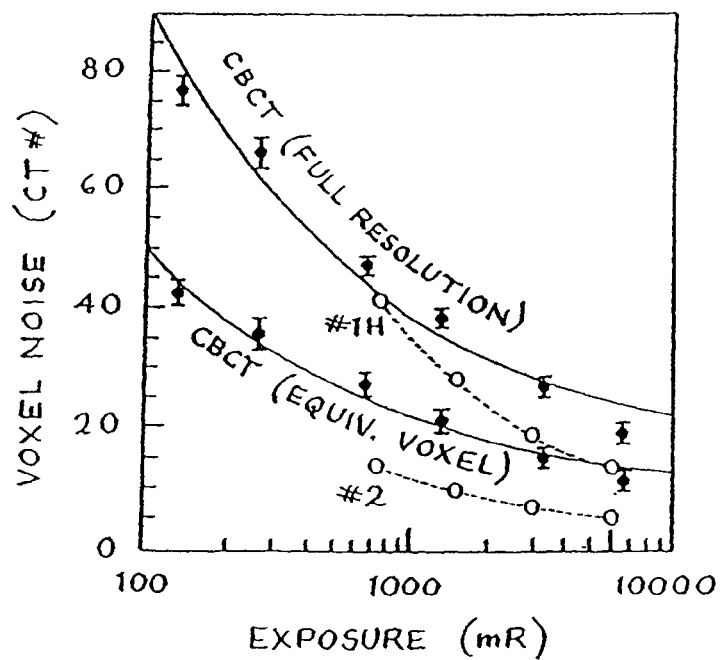

The noise measured for the cone beam computerized tomography system 300 as a function of exposure is shown in the top curve of FIG. 9(b). The noise is seen to decrease from −80 units at the lowest exposure examined down to −20 units at the highest. Superimposed is a least squares fit of the form $\sigma = \alpha + b/\sqrt{X}$, where $\sigma$ is the noise in voxel values, X is the exposure in air at the isocenter, and a and b are constants obtained from the numerical fit. This inverse-square root dependence upon exposure is consistent with basic noise transfer theory for x-ray tomographic reconstructions.

In order to examine the linearity and accuracy of system response, the CT numbers reported by the cone beam computerized tomography system 300 for a variety of materials (FIG. 6) were compared to those reported by the conventional scanner. As shown in FIG. 9(b), the CT numbers of the cone beam computerized tomography system 300 agree well with those of the conventional scanner. The largest discrepancy over the range of CT numbers was 8 units, with an average discrepancy of 5.7. The high coefficient of correlation indicates that, over the range examined, the values reported by the cone beam computerized tomography system 300 are proportional to attenuation coefficient.

The voxel noise of the cone beam computerized tomography system 300 and the conventional scanner was compared as a function of exposure, shown in FIG. 9(b). Shown by the open circles and dashed lines are the results for the conventional scanner using the "High-Res Head (#1 H)" and "Standard Head (#2)" reconstruction filters. In each case, the noise decreases with exposure. An exact comparison between the two systems requires that both data sets be reconstructed at equivalent voxel size and with the same reconstruction filter. The requirement for equivalent voxel size was achieved by repeating the noise analysis for the cone beam computerized tomography system 300, with the volume data averaged to give a voxel size equivalent to that of the scanner.

In order to illustrate the effect of the reconstruction filter upon the voxel noise, reconstructions were performed with both the "High-Res Head" and "Standard Head" reconstruction filters. The noise for the cone beam computerized tomography system 300 at equivalent voxel size is shown by the lower solid curve with a least-squares fit superimposed. At equivalent voxel size, it is clear that the cone beam computerized tomography system 300 has higher noise at lower exposures than the "Standard Head" computerized tomography scanner results. Compared to the "High-Res Head" results for the conventional scanner, however, the cone beam computerized tomography system 300 actually provides lower noise at all but the very highest exposures. Clearly, careful matching of reconstruction filters and reconstruction matrix is required to permit exact intercomparison of the two systems. Nonetheless, the results obtained using the cone beam computerized tomography system 300 are encouraging, since the early prototype flat-panel detector used in this system is known to exhibit a fairly high level of additive electronics noise, a factor of −5-10 higher than that achieved, by more recent electronics designs.

Figure 10A:
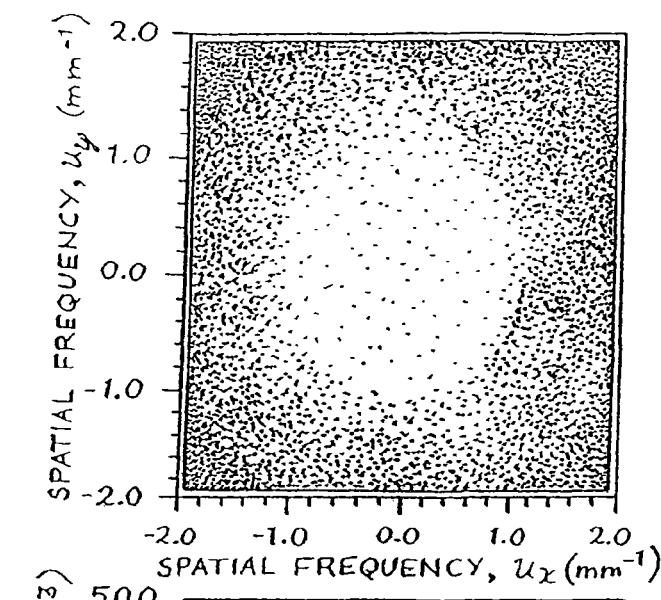
FIGS. 10(a)-10(c) depict the noise-power spectrum from the cone beam computerized tomography system of the present invention, including a gray scale plot of the axial noise-power spectrum, the noise-power spectrum measured at various exposures, and the noise-power spectrum for the cone beam computerized tomography system compared to a conventional computerized tomography scanner, respectively.
Figure 10B:
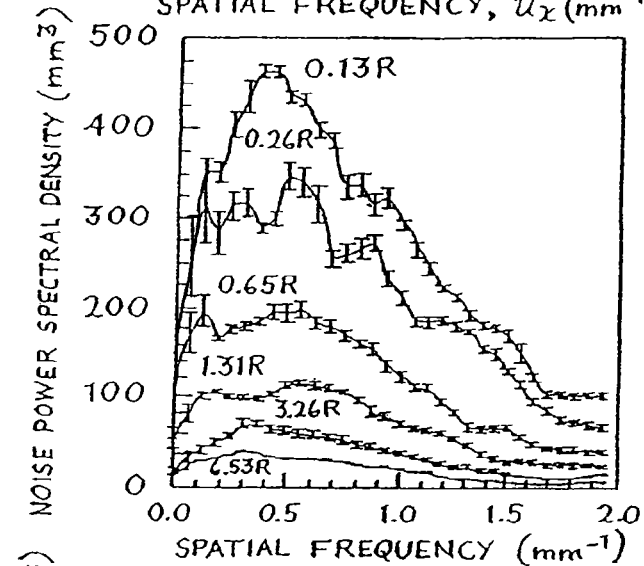
Figure 10C:
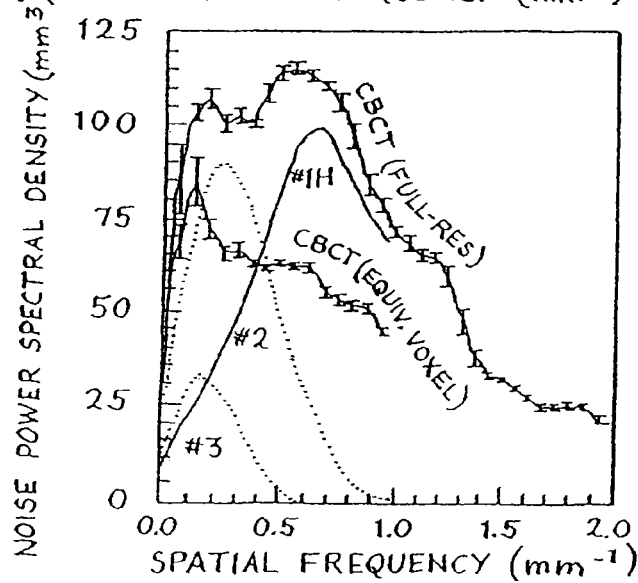

Results of the noise-power spectrum measurements are summarized in FIGS. 10(a)-10(c). The 2-D noise-power spectrum in the axial plane (FIG. 10(a)) exhibits a spectral shape typical of systems employing filtered back-projection reconstruction. The spectral density is reduced (but non-zero) near zero-frequency, increases at mid-frequencies due to the ramp filter (e.g., peaking around −0.5 mm$^{-1}$), and declines at higher frequencies by virtue of the low-pass noise characteristics of the system (e.g., 2-D image blur and choice of apodisation window). Slices of the noise-power spectrum along the $u_x$ dimension are shown in FIG. 10(b) for various exposure levels. Since the mean signal level is fixed for each case (i.e., CT#=1000 within the water phantom), the noise-power spectrum decreases with increasing exposure.

Specifically, the noise-power spectrum appears inversely proportional to exposure in a fashion consistent with the form of the numerical fits in FIG. 9(b). As shown in FIG. 10(c), the noise-power spectrum measured at −1.3 R (in air at isocenter) is ~30 mm.sup.3 near zero-frequency, increases by a factor of ~4 at mid-frequencies, and then descends to about the initial level of spectral density at the Nyquist frequency.

Superimposed in FIG. 10(c) are the results measured for the conventional scanner using three reconstruction filters, and to facilitate intercomparison, noise-power spectrum results for the cone beam computerized tomography system 300 are shown for an equivalent voxel size. For the #2 and #3 filters, the conventional scanner exhibits a noise-power spectrum with the characteristic shape described above; however, the high-resolution #1 H filter is seen to significantly amplify high-frequency noise. The cone beam computerized tomography system 300 appears to exhibit low-frequency noise-power spectrum comparable to the conventional scanner using the #2 and #1 H filters. Given that the choice of reconstruction filter can significantly affect noise and spatial resolution, and considering the two cases that seem most closely matched the cone beam computerized tomography system 300—even in its initial, un-optimized configuration—appears to provide noise performance comparable to the conventional scanner. As evident in FIG. 9(b), the cone beam computerized tomography system 300 exhibits lower voxel noise than the conventional scanner (#1 H) at low exposures. Similarly, the cone beam computerized tomography system 300 exhibits reduced high-frequency noise-power spectrum. These initial results are especially promising considering the on-going improvements in FPI design and readout electronics.

Figure 11A:
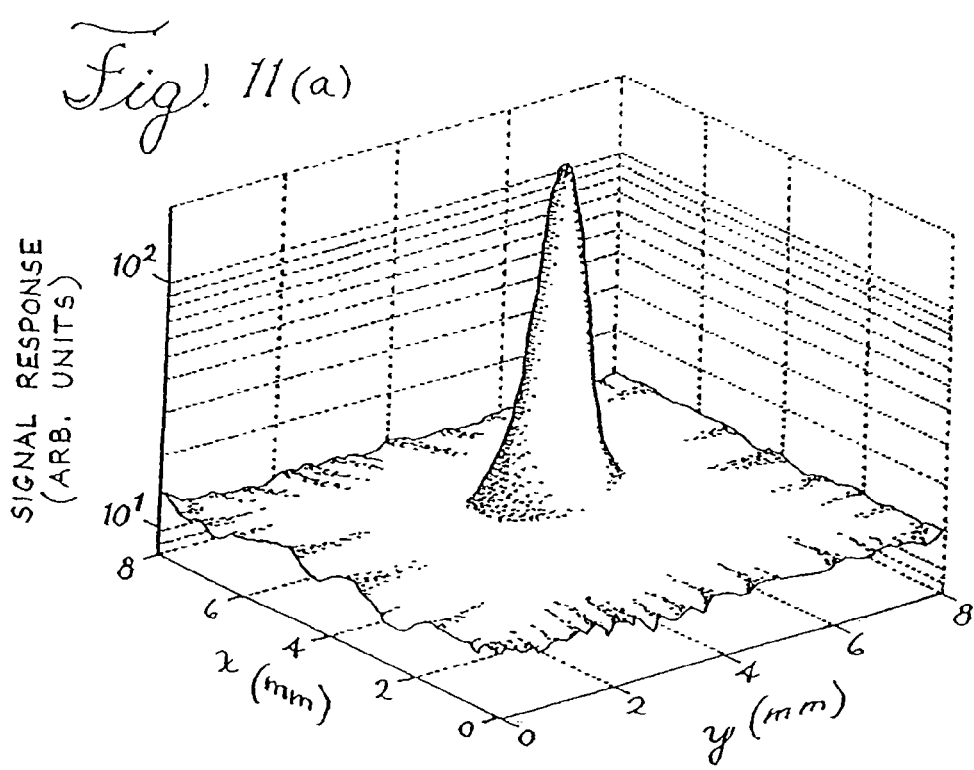
FIGS. 11(a)-11(b) depict the spatial resolution of the cone beam computerized tomography system of the present invention, including the surface plot of an axial slice image of the thin steel wire shown in FIG. 6(c) and the modulation transfer function measured for the cone beam computerized tomography system and for a conventional computerized tomography scanner, respectively.
Figure 11B:
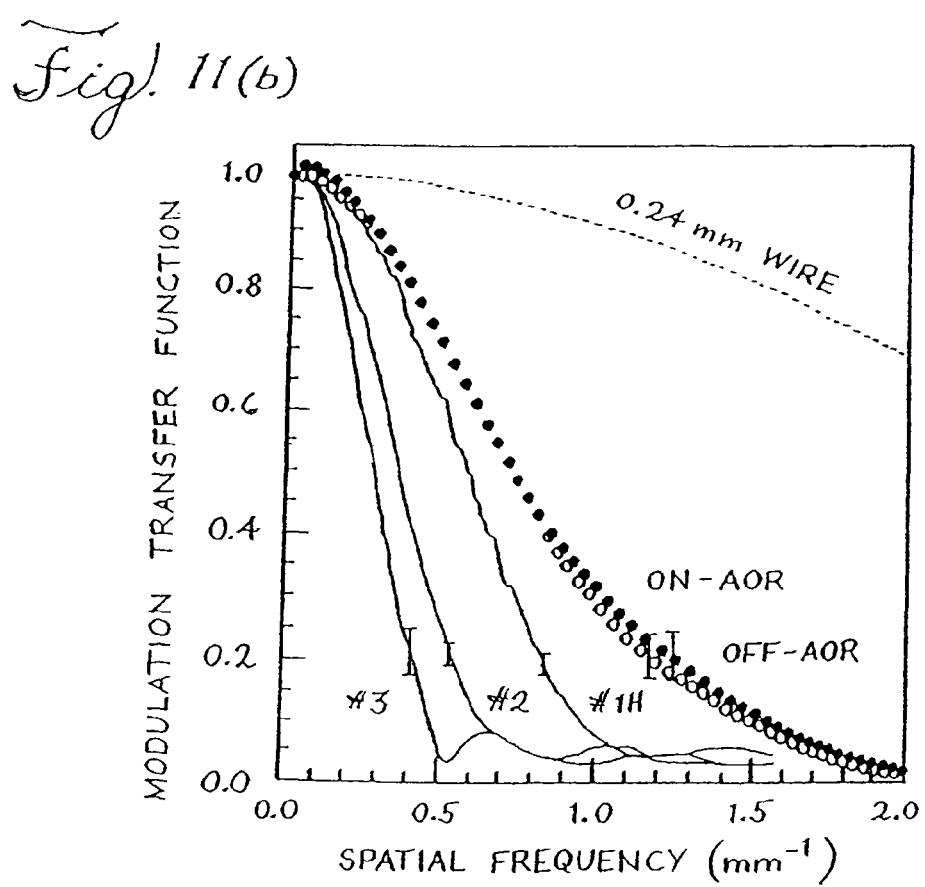

The response of the cone beam computerized tomography system 300 to the wire test object is presented in FIG. 11(a). Overall, the PSF is symmetric (aside from a small streak artifact believed associated with the image lag characteristics of the system) and has a full-width at half-maximum (FWHM) of 0.6 mm. The system MTF is shown in FIG. 11(b) for both the on- and off-axis wire results. These results suggest that the frequency pass of the system in the z=0 plane does not change significantly over the relatively small (~30 mm) range examined. The strong influence of the reconstruction filter is demonstrated in the MTF results for the conventional scanner, also shown in FIG. 11(b).

The "Standard Head (#2)" filter significantly reduces the signal pass of the system compared to the High-Res Head (#1 H)" filter. The results demonstrate that the MTF of the conventional scanner is comparable to that of the cone beam computerized tomography system 300 when the "High-Res Head (#1 H)" filter is used. This observation is consistent with the noise results presented in FIG. 9(b). The resolution of the cone beam computerized tomography system 300 and conventional scanner have not been compared in the z-dimension. It is expected, however, that the spatial resolution of the cone beam computerized tomography system 300 in the z-dimension will be comparable to that measured in the axial plane. Of course, the spatial resolution of the conventional scanner will be limited by the selected slice thickness, which is typically 1 mm or greater. The nearly isotropic resolution of the cone beam computerized tomography system 300 is expected to be a significant advantage for detection and localization.

Figures 12A, 12B:
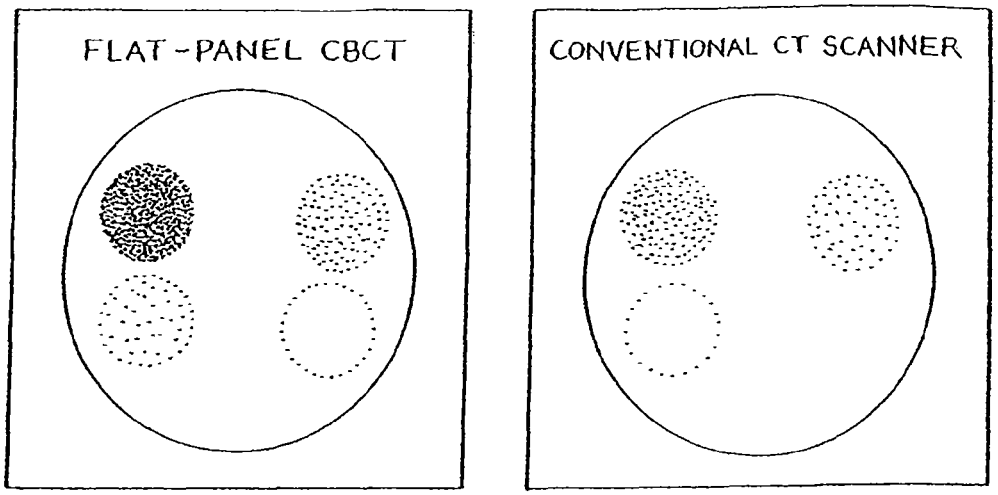
FIGS. 12(a)-12(b) show images of a low-contrast phantom obtained from the cone beam computerized tomography system of the present invention and a conventional computerized tomography scanner, respectively.

FIGS. 12(a) and 12(b) show axial image slices of the low-contrast phantom obtained on the cone beam computerized tomography system 300 and the conventional computerized scanner at equivalent kVp and exposure. The grayscale window in each case is quite narrow in order to maximize the displayed contrast, and despite the slight signal non-uniformity evident for the cone beam computerized tomography image (cupping/capping artifact discussed above) the visibility of each insert is comparable to the conventional scanner. The mean signal values for each material are as shown in FIG. 9(a). Slight differences in system response (e.g., due to detector response, x-ray spectrum, etc.) can result in contract reversal for materials with CT# very close to that of water. For example in the case of the brain insert (lower right), even the slight (~5 CT#) difference between the mean value reported by the cone beam computerized tomography system 300 and the conventional scanner is sufficient to give an apparent inversion in the density of the material relative to water. The minimum detectable contrast is arguably superior for the cone beam computerized tomography system 300 (e.g., visibility of the brain and CB-3 inserts), but this remains to be verified by a more controlled, quantitative observer study.

The overall performance of the cone beam computerized tomography system 300 is demonstrated in the images of the volumetric data set illustrated in FIGS. 13(a)-13(i). These images of an euthanized rat demonstrate the soft tissue sensitivity and high spatial resolution of the system. Example images are shown from various regions throughout the volumetric set [e.g., in regions of the lungs (a, b, c), the kidney (d, e, f), and lower spine (g, h, i)] to illustrate the quantity and uniform quality of the data produced with the cone beam computerized tomography system 300. The clear visualization of soft-tissue structures demonstrates the soft-tissue contrast sensitivity of the scanner.

Figure 13A:
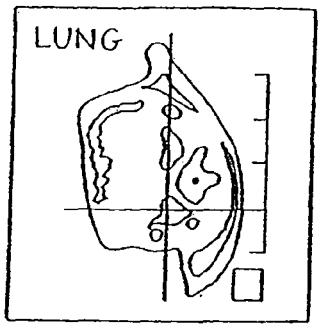
FIGS. 13(a)-13(i) show cone beam computerized tomography images of the euthanized rat shown in FIG. 6(d), including regions of the lungs (FIGS. 13(a)-13(c)), the kidneys (FIGS. 13(d)-13(f)), and the lower spine (FIGS. 13(g)-13(i))
Figure 13B:
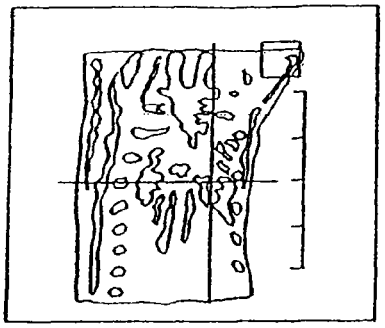
Figure 13C:
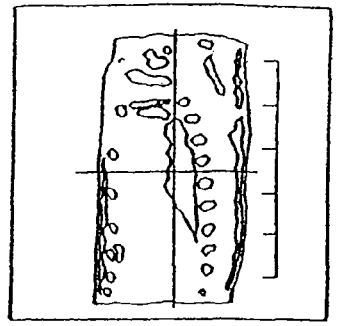

In FIGS. 13(a)-13(c), the window and level have been set to emphasize features in the lung of the rat. In addition to the lung detail, there are some streak artifacts evident, the origin of which is unknown, but is believed to be associated with detector lag effects or beam hardening.

Figure 13D:
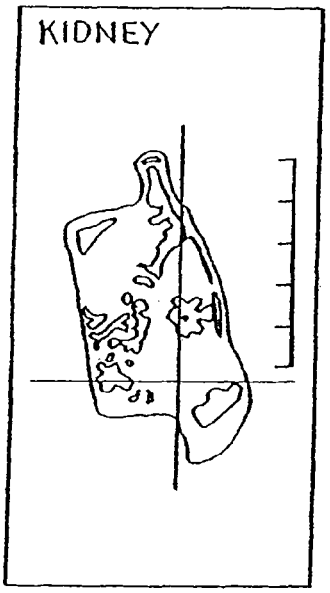
Figure 13E:
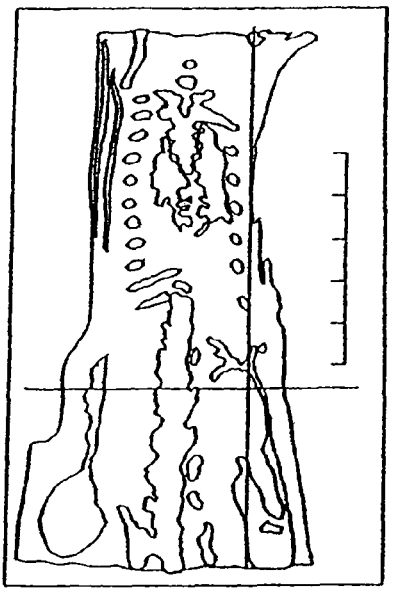
Figure 13F:
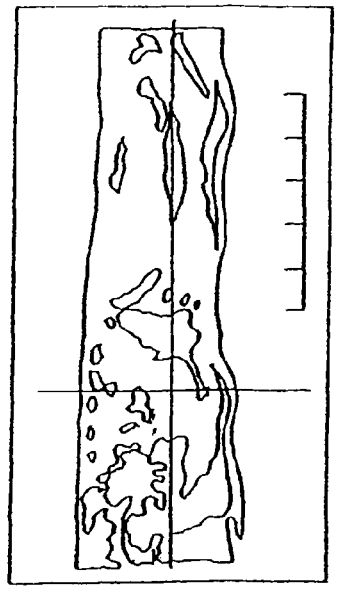
Figure 13G:
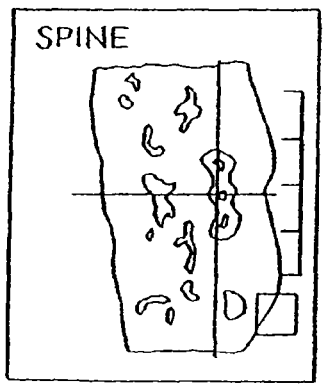
Figure 13H:
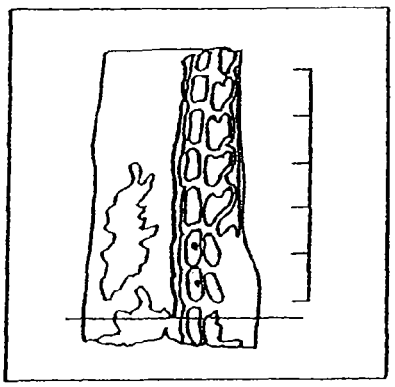
Figure 13I:
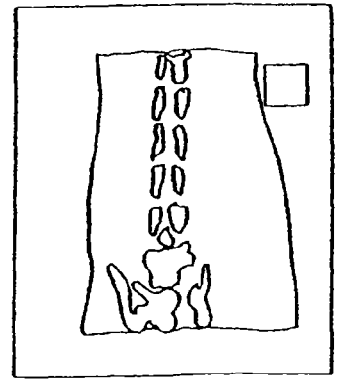

The soft tissue contrast sensitivity of the cone beam computerized tomography system 300 is illustrated in FIGS. 13(d)-13(f), in which the window and level have been set to delineate fat and muscle. The cross-hair in each image indicates the location of the rat's left kidney. These images illustrate the advantage of a nearly isotropic spatial resolution for delineation of a 3-D structure such as the kidney. Other structures, such as the stomach, bowel and liver are also clearly visible.

The spatial resolution performance of the system 300 is demonstrated in FIGS. 13(g-i), in which the same rat data set is displayed with window and level selected to display bony features. The clear visibility of the intervertebral spaces and the non-cortical bone in the pelvis is stunning It should be kept in mind that this level of detail was produced on a cone beam computerized tomography system 300 that operates on a scale that mimics the geometry of the linear accelerator. Therefore, this level of detail would be expected in the clinical implementation of the device, given accurate correction of mechanical flex. The volumetric data set is illustrated further in FIG. 14, in which volume renderings demonstrate the fully 3-D nature of the data set and show the level of detail contained within the cone beam computerized tomography data. It is interesting to note that all the data presented in FIGS. 13 and 14 were obtained from a single acquisition performed in a single rotation.

Finally, the quality of images produced by the cone beam computerized tomography system 300 was assessed by comparison to images produced by the conventional scanner. FIGS. 15(a)-15(b) show an axial slice of the rat acquired on the two systems. At equivalent exposure, the images produced by the two systems are of comparable quality both in terms of spatial resolution and contrast sensitivity. The flat panel imager-based cone beam computerized tomography image exhibits exquisite spatial resolution and provides clear delineation of soft-tissue boundaries and detail in the gut. The spatial resolution of the cone beam computerized tomography system 300 appears to exceed that of the conventional scanner; however, it must be noted that restrictions in available reconstruction matrices for the conventional computerized tomography scanner limited the voxel size to twice that of the cone beam computerized tomography image. Lack of obvious pixelation in the flat panel imager-based cone beam computerized tomography image indicates that this level of detail represents the physical limits in spatial resolution of the current system.

The objective of these investigations is to evaluate the applicability of flat-panel technology as a detector in a cone beam computerized tomography system, specifically, a tomographic imaging system for use in the guidance of radiation therapy on a medical linear accelerator.

The quantitative and qualitative results of our studies suggest that a cone beam computerized tomography scanner based on flat panel detector technology is a viable means for high performance computed tomography. Initial studies of signal response uniformity demonstrated that the response of the system is uniform over the field of view to within .+−.2%, with the slight degree of non-uniformity apparent as a combined cupping and capping artifact in the x-y plane attributable to a reconstruction artifact. The linearity of response was demonstrated using a range of soft-tissue test materials and was found to be linear to within .+−.−0.6%. Measurements of image noise versus exposure demonstrate that the prototype cone beam computerized tomography system 300 performs comparably to the conventional scanner, demonstrating the inverse square root exposure dependence predicted by theory. Investigations of noise power spectrum and spatial frequency response for the two systems reinforce these conclusions and illustrate the advantages of developing more extensive (empirical and theoretical) frequency-dependent characterization methods for volumetric computed tomography systems.

In addition to the quantitative measures of performance, the images of low-contract phantoms and small animal anatomy confirm the conclusions drawn from these measures, showing excellent detail and soft-tissue contract, more than sufficient for tissue localization in radiation oncology.

The results presented here demonstrate the potential of this approach for volumetric imaging. However, this study has been performed under conditions of small object size and small cone angle. These conditions are imposed by the size of the detector used in this investigation. Imaging with larger detectors allows increased cone angle and, for computerized tomography, increased object thickness. The extrapolation of performance based on the results presented here to that for larger detectors must be done with some caution. Imaging larger objects with an increased field of view will result in increased scatter and reduced transmission. The increase in scatter can be expected to have a negative impact on computerized tomography imaging performance by introducing non-uniformities in the reconstructed image (e.g., cupping and/or streaks), and by adding additional x-ray quantum noise to the image signal. The magnitude of scatter reaching the detector will depend greatly on the cone-angle and air gap employed, and studies suggest that scatter at these distances may be reduced compared to conventional radiographic applications. Quantifying the magnitude of the x-ray scatter problem and developing methods to reduce it are areas of ongoing investigation.

Figure 16:
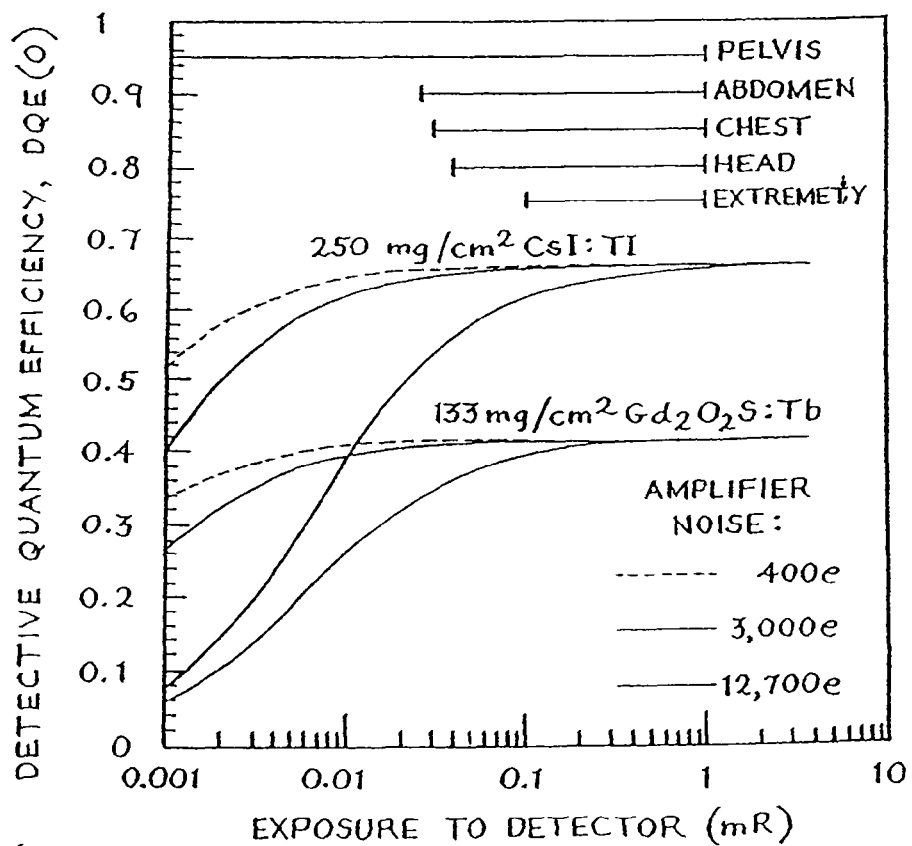
FIG. 16 is a graph showing detected quantum efficiency calculated as a function of exposure for an existing and hypothetical flat-panel imager configuration.

In addition to concerns of x-ray scatter at large cone-angles, the scanning of larger objects will significantly reduce the fluence arriving at the detector. This reduced transmission will negatively impact the performance of the flat-panel detector. Currently available flat panel imagers demonstrate performance inferior to conventional image intensifiers at fluoroscopic exposure rates, due to the presence of additive noise in the flat-panel readout electronics. Additive noise causes the detected quantum efficiency of the imager to depend on the number of x-rays forming an image. This dependence is illustrated in FIG. 16 for the flat-panel imager 306 used in these investigations and for hypothetical detectors that embody the most recent advances in imager 306 design, including higher x-ray quantum detection efficiency through the use of Csl:TI and a reduction in additive noise through improvements in readout electronics.

The zero-frequency detected quantum efficiency was computed using a model for signal and noise transfer that has demonstrated excellent agreement with measurements. It is clear from FIG. 16 that improvements in the x-ray converter and electronics noise significantly reduce the exposure dependency of the detected quantum efficiency over the broad range of exposures required for computerized tomography. The magnitude of the reduction depends greatly on the amplifier noise in the system. For the prototype imager used in these studies, the amplifier noise is very high at 12,700 e. For the low transmitted exposure levels in computerized tomography of pelvic anatomy, for example, this detector would achieve a zero-frequency detected quantum efficiency of less than 10%. In comparison, an imager than incorporates the recent advances in design listed above (e.g., a high-quality Csl:TI converter and amplifier noise of 3000 3 or better) would achieve a higher detected quantum efficiency (−65%) at full transmission and maintain a detected quantum efficiency of >40% even at the low exposure levels. Such enhancements in imager design are within the current capabilities of flat panel imager manufacturers and will greatly facilitate the application of flat panel imagers in cone-beam computerized tomography of human beings. Furthermore, these improvements are largely driven by other forces in digital imaging that anticipates use of flat panel imagers in place of conventional image-intensifier systems for interventional fluoroscopy. For this reason, it can be expected that imagers with such characteristics will be available within the next five years.

Overall, the operating characteristics of the flat-panel are highly compatible with acquisition in a cone beam computerized tomography scanning geometry. Unlike image-intensifier or lens based systems, flat panel detectors are geometrically robust under a rotating geometry, eliminating concerns of image distortion. The proximity of the analog-to-digital converter to the pixel element and the relatively large charge signals make the panels robust in high radio-frequency power environments; this is of particular interest for radiotherapy applications. The high readout rate of these detectors allows for imaging sequences of 300 projection images to be acquired within 10 seconds (operating at 30 fps). This is more than sufficient to satisfy the allowable rotation rates for the gantry of a medical linear accelerator. In fact, while the International Electromechanical Commission (IEC) recommends less than 1 revolution per minute for linear accelerators, it would be reasonable to reconsider such constraints in light of the advantages of cone beam computerized tomography guidance in the treatment room. Currently, the detector size and aspect ratio are driven by the needs of digital radiography, producing detectors comparable in size to radiographic film. These sizes limit the field-of-view of the reconstruction if sufficient clearance is to be maintained between ft detector and patient during gantry rotation. This problem can be addressed using offset detector schemes that use 360.degree.

of gantry rotation. Ultimately, a specialized detector could be designed with a size and aspect ratio that match the requirements for cone beam computerized tomography (e.g., a ~25.times.50 cm.sup.2 area panel).

Given the potential that this technology is demonstrating, the opportunities for new areas of application for computed tomography are significant. Imaging systems based on this technology can be constructed to address specific imaging problems, including non-destructive testing (at kilovoltage or megavoltage energies), early detection and monitoring of specific medical conditions, and, of course, navigational imaging for therapies. The compact nature of the panels allow flat panel imager-based cone beam computerized tomography imagers to be applied in situations that would never be considered feasible for a conventional computerized tomography scanner. The cone beam computerized tomography approach offers two important features that dramatically reduce its cost in comparison to a conventional scanner. First, the cone-beam nature of the acquisition does not require an additional mechanism to move the patient (or object) during image acquisition. Second, the use of a cone-beam, as opposed to a fan-beam, significantly increases the x-ray utilization, lowering the x-ray tube heat capacity required for volumetric scanning For the same source and detector geometry, the efficiency roughly scales with the slice thickness. For example, the x-ray utilization increased by a factor of 30 in going from a 3 mm slice in a conventional scanner to a cone-angle corresponding to a 100 mm slice with a cone-beam system, This would decrease heat-load capacities dramatically. From our experience, a 5200 kHU x-ray tube costs approximately $70,000, whereas a 600 kHU x-ray tube (a factor of ~10 lower in capacity) costs roughly $6,000.

Cone-beam computed tomography has been a topic of active research and development for over a decade in areas such as nuclear medicine and industrial testing; however, only recently has it begun to appear in the diagnostic computerized tomography arena. The developments in this area have been for the most part limited to multi-slice detectors. In this investigation, the use of an alternative detector for high-quality computerized tomography has been studied. The results of the investigation suggest that there is a significant potential for the use of these detectors in cone beam computerized tomography systems for radiotherapy and quite possibly for diagnostic and interventional computerized tomography imaging tasks that will take advantage of the fully 3-D nature of cone beam computerized tomography.

Based upon the positive results presented previously with respect to the cone beam computerized tomography system 300, several embodiments of a flat panel imager-based kilovoltage cone beam computerized tomography scanner for guiding radiation therapy on a medical linear accelerator are envisioned. For example, FIGS. 17(a)-(e) and 18 are diagrammatic and schematic views of an embodiment of a wall-mounted cone beam computerized tomography system 400. The cone beam computerized tomography system 400 includes an x-ray source, such as x-ray tube 402, and a flat-panel imager 404 mounted on a gantry 406. The x-ray tube 402 generates a beam of x-rays 407 in the form of a cone or pyramid that have an energy ranging from approximately 30 KeV to 150 KeV, preferably approximately 100 KeV. The flat-panel imager 404 employs amorphous silicon detectors.

The system 400 may be retrofitted onto an existing or new radiation therapy system 700 that includes a separate radiation therapy x-ray source, such as a linear source 409, that operates at a power level higher than that of x-ray tube 402 so as to allow for treatment of a target volume in a patient. The linear source 409 generates a beam of x-rays or particles 411, such as photons or electrons, that have an energy ranging from 4 MeV to 25 MeV. The system 400 may also include an imager (not shown) that is aligned with the linear source 409 with the patient interposed therebetween. The imager forms projection images of the patient based on the remnants of the beam 411 that passes through the patient. Note that the x-ray sources 402 and 409 may be separate and contained with the same structure or be combined into a single source that can generate x-rays of different energies.

Figure 17B:
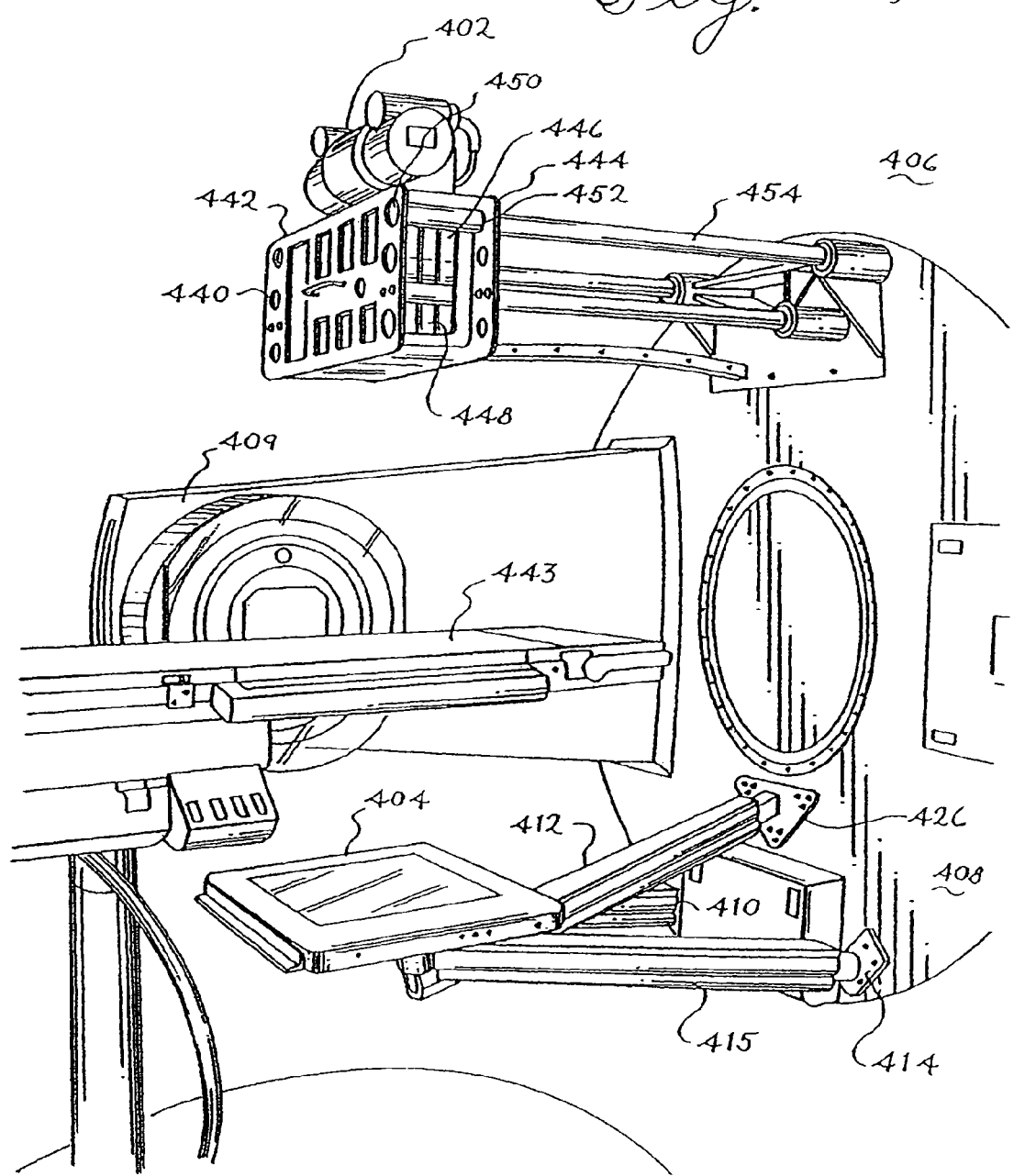
Figure 17A:
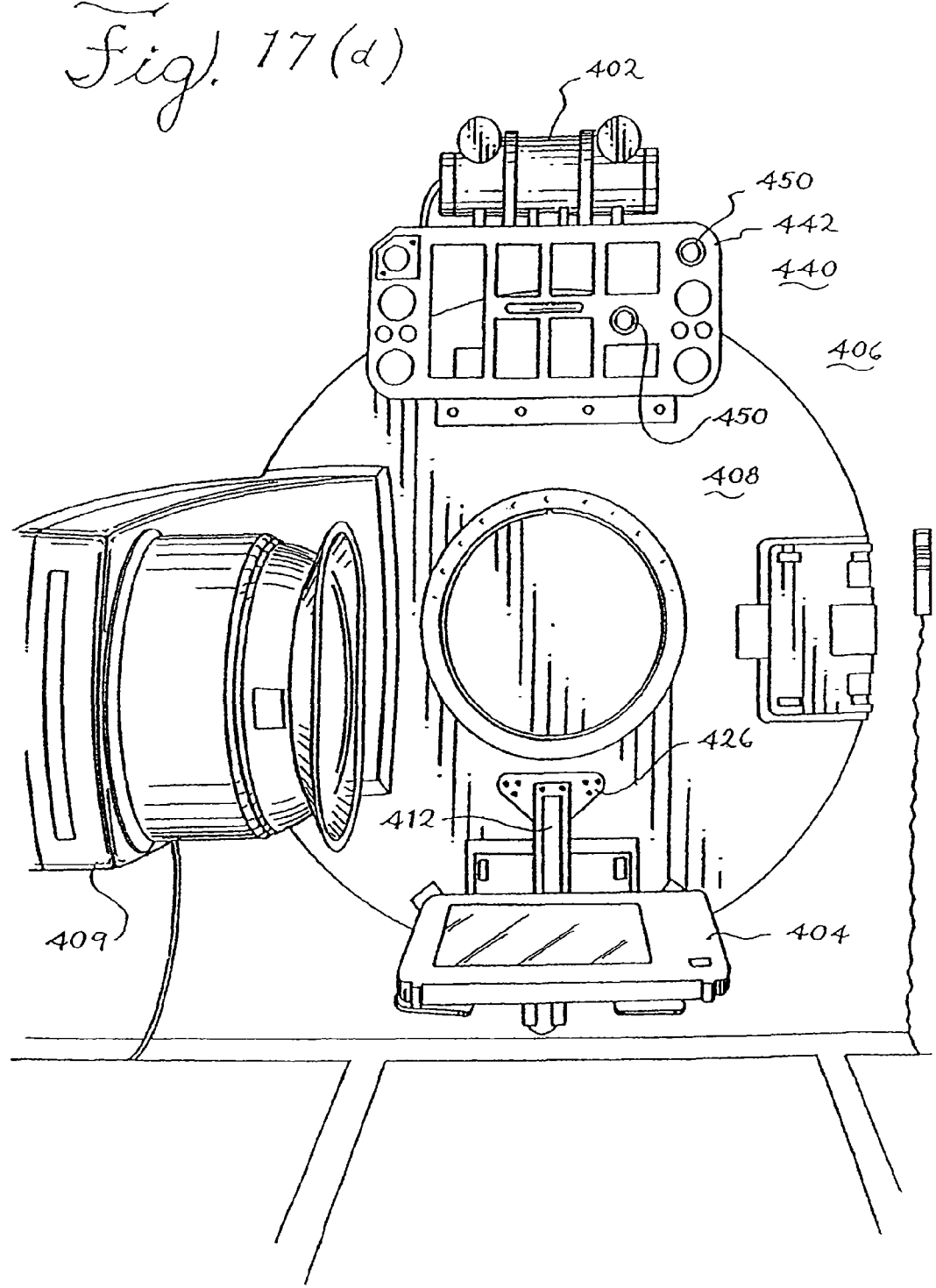

As shown in FIGS. 17(a)-(e) and 18-19, the flat-panel imager 404 can be mounted to the face of a flat, circular, rotatable drum 408 of the gantry 406 of a medical linear accelerator 409, where the x-ray beam 407 produced by the x-ray tube 402 is approximately orthogonal to the treatment beam 411 produced by the radiation therapy source 409. Attachment of the flat plane imager 404 is accomplished by an imager support system 413 that includes three 1 m long arms 410, 412 and 415 that form a tripod. Side arms 410 and 415 are identical to one another in shape and have ends attached to a Ax95 Guy pivot 417 which in turn is attached to a mounting 414 by screws that are threaded through aligned threaded holes of the pivot 417 and threaded holes 425 and 431 of plates 433 and 435, respectively, as shown in FIGS. 18 and 19(a)-(b). As shown in FIGS. 17(b) and 18, the mountings 414 for the arms 410 and 415 are aligned with one another along a line segment 419 that is contained within a plane 421 that is parallel to and offset by approximately 30 cm from the plane containing the flat-plane imager 404. The mountings 414 are separated from one another by approximately 70 cm and are symmetrically positioned with respect to a plane bisecting an imager mount 423 that is attached to the drum 408 270.degree. from the radiation therapy source 409.

Figure 19A:
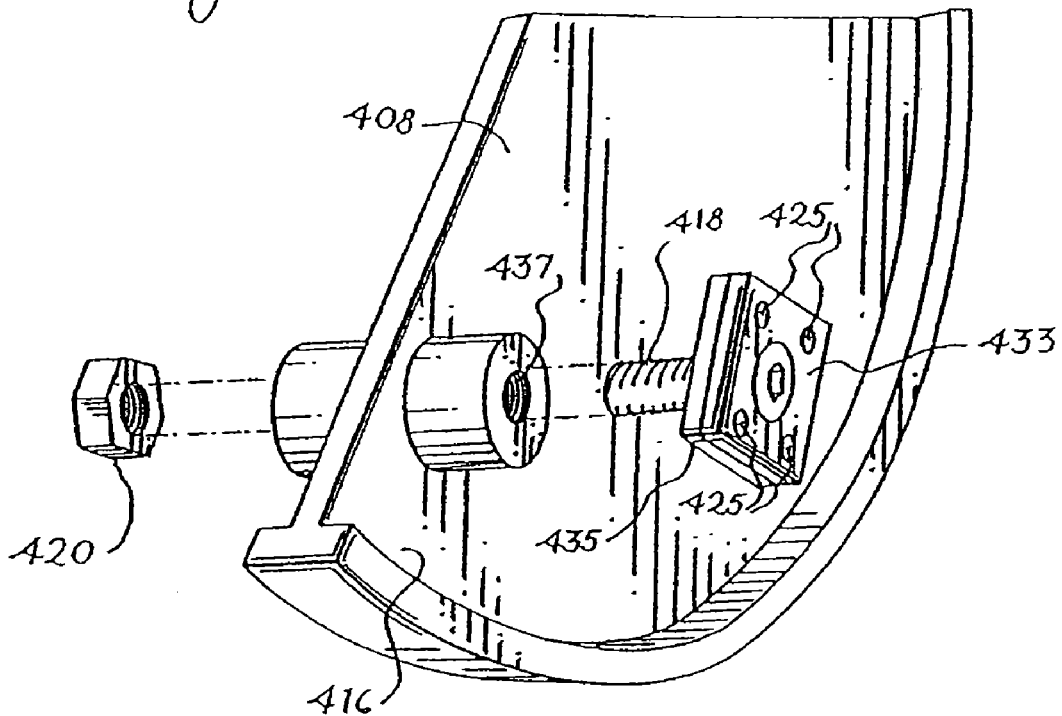
FIG. 19(a) shows a perspective exploded view of a mounting to be used with the support for a flat-panel imager of FIG. 18.
Figure 19B:
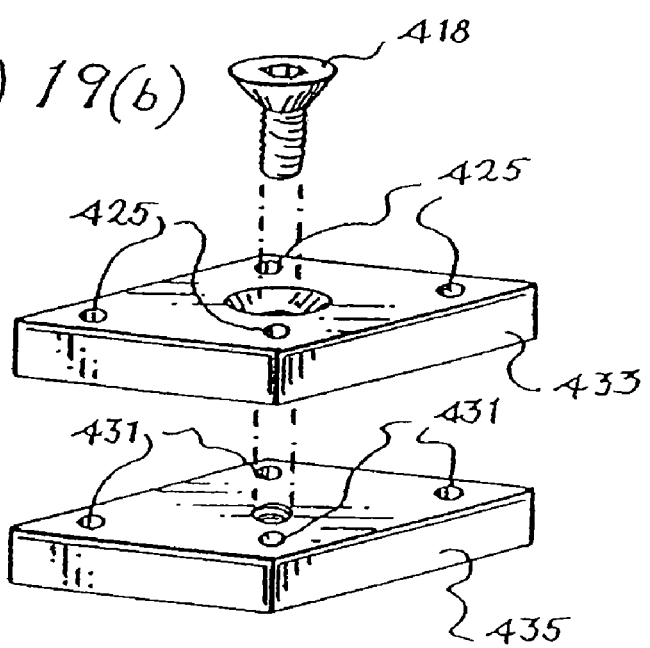
FIG. 19(b) shows a perspective exploded view of a rotational coupling to be used with the mounting of FIG. 19(a)

As shown in FIGS. 18 and 19(a)-(b), each mounting 414 is attached to an end portion 416 of the drum 408 by inserting a threaded male member 418 through an opening 437 formed through the drum 408. Once inserted, the male member 418 is attached to the drum 408 by tightening a nut 420 onto the threaded male member 418. The other ends of the arms 410 and 415 are attached to Ax95 Guy pivots 422 attached to the back of an ⅜ inch thick Aluminum square plate 424 is attached to the rear of the flat-panel imager 404 via bolts (not shown).

Figure 17E:
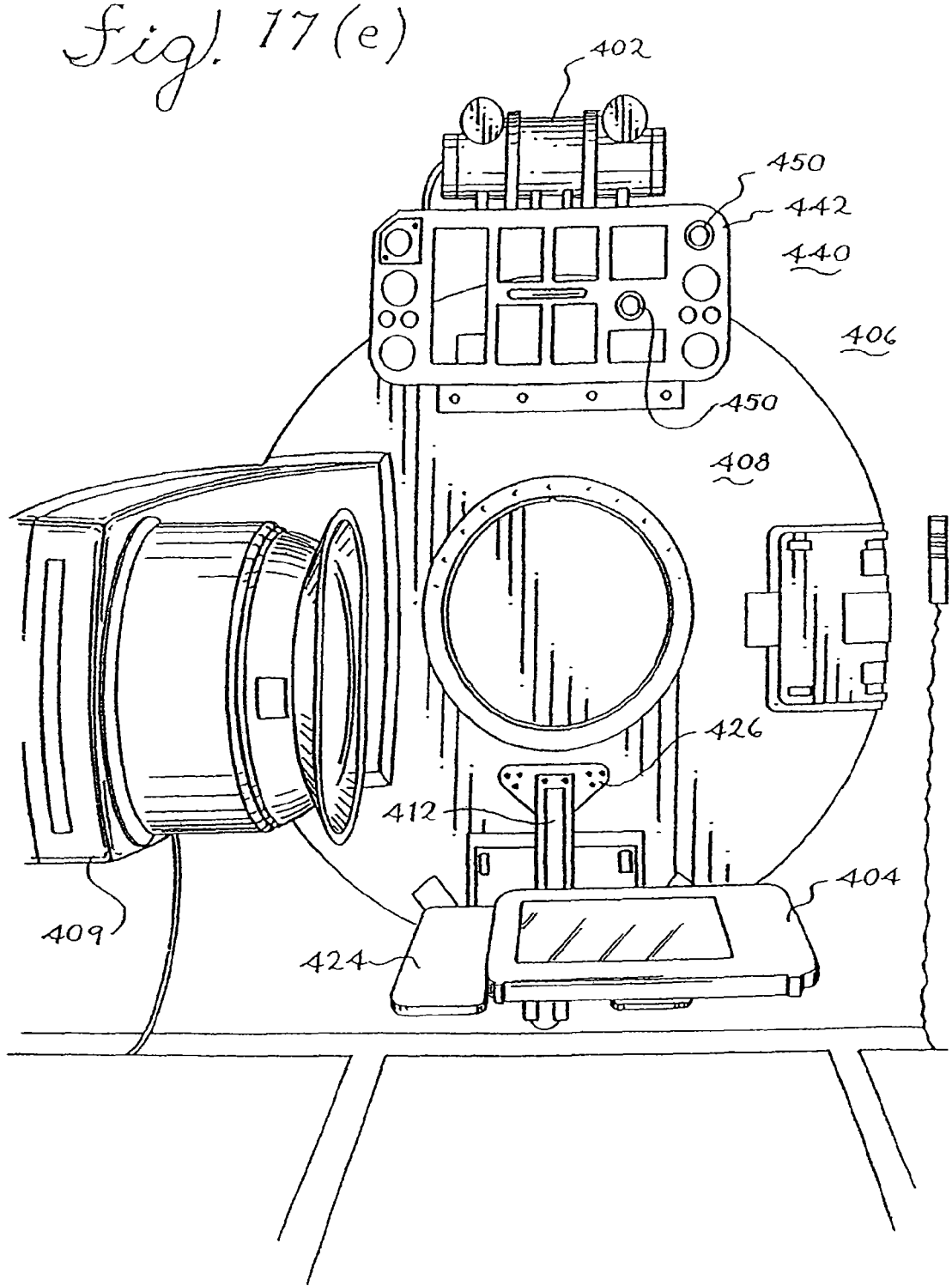

As shown in FIGS. 17(d)-(e), there are two preset positions of the flat panel imager 404 relative to the plate 424. As shown in FIG. 17(d), the flat panel imager 404 is centered about the ends of the arm 412. In order to provide a larger field of view, an offset flat panel imager 404 can be used as shown in FIG. 17(e) where the imager 404 is attached to a side of the plate 424 via bolts. Note that it is possible to use a motorized system to move the flat panel imager 404 relative to the plate 424 to provide an easy way to vary the field of view of a cone beam computerized tomography system.

A center arm 412 is also attached to the drum 408 and the flat-panel imager 404. The center arm 412 has one end attached to Ax95 Guy pivot 427 that is in turn attached to a tapped, triangular-shaped, reinforcing plate 426 formed on the drum 408 as shown in FIGS. 17(b) and 18. The plate 426 is approximately 433.8 mm from the rotational axis 428 that intersects the iso-center 430 of the imaging system 400. A second end of the center arm 412 is attached to the plate 424 via a Cx95A right angle joint 425.

As shown in FIGS. 17(b) and 18, the end of the arm 412 lies along a line that is the perpendicular bisector of the line segment 419 and is radially separated from the midpoint between mountings 414 as measured along line segment 419 by a distance D of approximately 30 cm.

As shown in FIGS. 17(*b*) and 18, the other ends of the arms 410, 412 and 415 are attached to the plate 424 so as to be positioned approximately 20 cm from the rear edge 429 of the plate 434 and approximately midway between the left and right edges of the plate 424.

Once the arms 410, 412 and 415 are attached to the drum 408 and the plate 424, the arms can be pivoted so that the flat panel imager 404 moves to a position where its rear side is separated from the iso-center 430 by a distance L of approximately 600 mm. One advantage of the imager support system 413 is that it can be used to retrofit existing stand-alone radiation treatment devices so they have the capability to have a flat panel imager attached thereto. The imager support system 413 is very rigid, i.e., constant tension and compression, which reduces movement of the imager 404 and so leads to cleaner imaging data.

Note that the x-ray tube 402 can also be retrofitted onto an existing stand-alone treatment device so as to be positioned opposite to the flat panel imager 404. As shown in FIGS. 17(*a*)-(*e*), the x-ray tube 402 is attached to tube support 440 that is composed of a pair of front and rear faces 442 and 444 and a pair of side faces 446. A multi-leaf collimator 448 is supported within the interior of the tube support 440. The front and rear faces 442 and 444 each include three openings 450, 452 that are aligned with one another and receive three cylindrical support arms 454 that are attached to a bearing housing 456 that is bolted to the drum 408. The tube support 440 and the x-ray tube 402 are able to slide along the support arms 454. Note that a cable support spans between the tube support 440 and the bearing housing 456 and contains the wiring necessary to operate the x-ray tube 402.

Figures 20A, 20B:
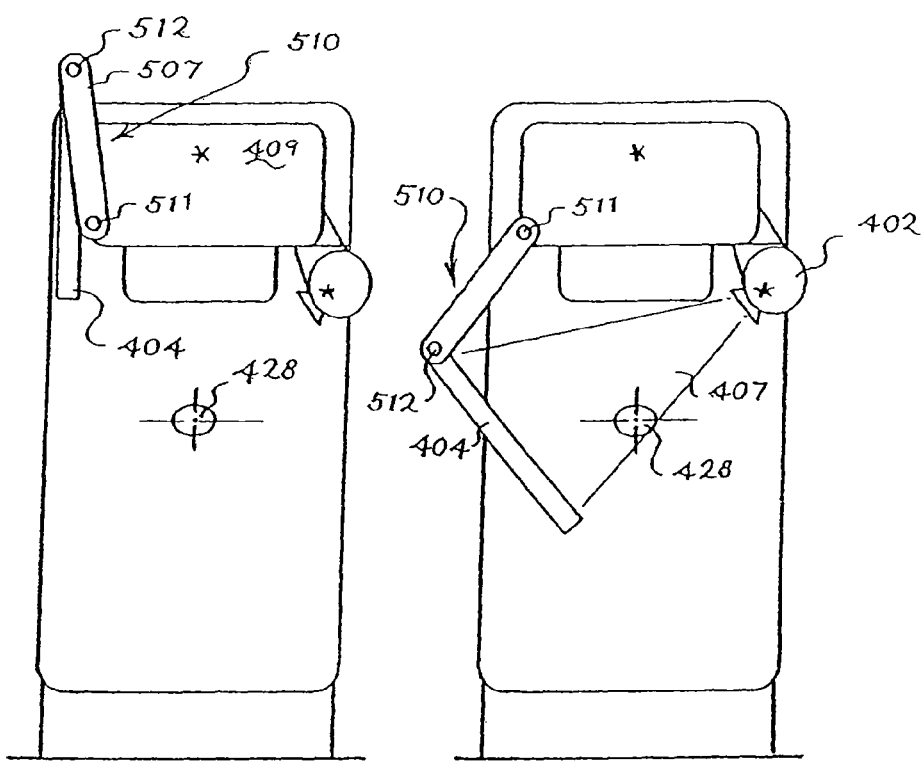
FIGS. 20(a)-(b) schematically shows a front view of the wall-mounted cone beam computerized tomography system of FIG. 17 when employing a second embodiment of a support for a flat-panel imager according to the present invention.

An alternative imager support system for the flat panel imager 404 of FIG. 17 is shown in FIGS. 20(*a*)-(*b*). In particular, the imager support system 507 shown in FIGS. 20(*a*)-(*b*) includes a single pivoting arm 510 that has one end 511 pivotably attached to a lower corner of the radiation therapy source 409. The other end 512 of the arm 510 is pivotably attached to an end of the flat-panel imager 404. The arm 510 and flat-panel imager 404 are movable from a retracted position of FIG. 20(*a*) to an extended position of FIG. 20(*b*) and vice versa. Movement of the arm 510 and the flat-panel imager 404 may be moved either manually or via a motor.

Note that when the imager support system 507 is used, the x-ray tube 402 is attached to a second lower corner of the radiation therapy source 409 in order to simplify the support structure and reduce the mechanical complexity of the overall system. The position of the x-ray tube 402 also reduces interference with staff access to the patient. Note that in this embodiment, the distance from the x-ray tube 402 to the axis of rotation 428 is not necessarily equal to the distance from the radiation therapy source 409 to the axis of rotation 428. Also, the amount of extension of the arm 510 shown in FIG. 20(*b*) will vary depending on the desired field of view for cone beam computerized tomography imaging. Note that if the mechanics are engineered to be sufficiently precise, the arm 510 can move in and out during image acquisition during gantry rotation so as to allow the imager 404 to dynamically avoid potential rotation-induced collisions with the patient or the table. The head of the radiation therapy source 409 can be altered to provide additional lead shielding on the imager side to limit radiation induced damage to the imager 404 while in the retracted position of FIG. 20(*a*). This will increase the life span of the imager 404.

Figures 21A, 21B:
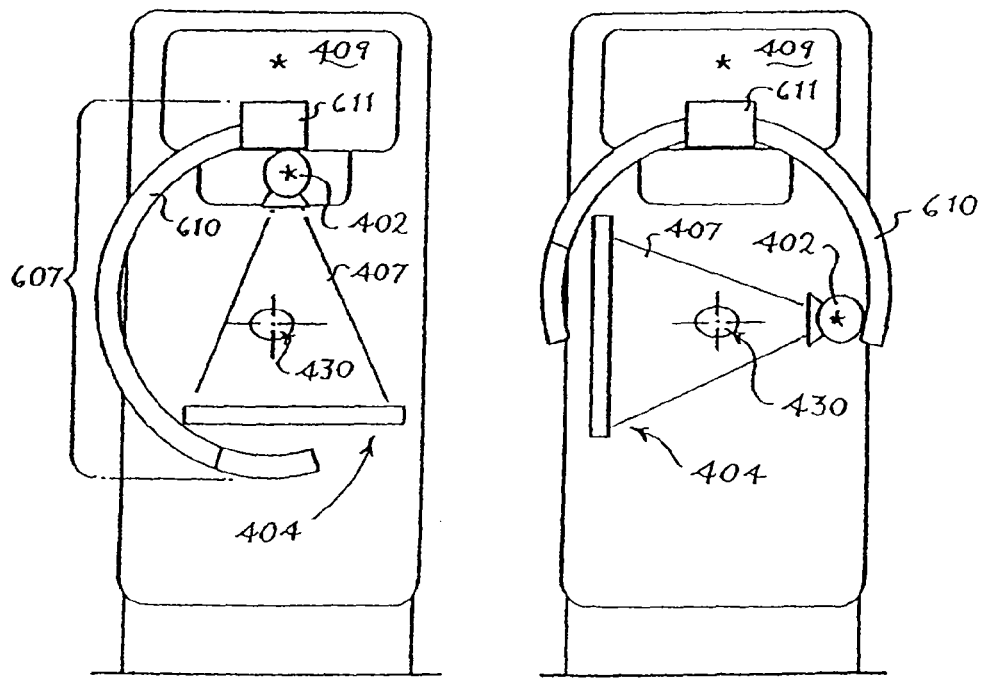
FIGS. 21(a)-(b) schematically shows a front view of the wall-mounted cone beam computerized tomography system of FIG. 17 when employing a third embodiment of a support for a flat-panel imager according to the present invention.

A second alternative imager support system for the flat panel imager 404 of FIG. 17 is shown in FIGS. 21 (*a*)-(*b*). In particular, the imager support system 607 shown in FIGS. 21 (*a*)-(*b*) includes a single C-arm 610 that is attached to an arm support 611 that is attached to the front or rear of the radiation therapy source 409. At one end of the C-arm 610 the x-ray tube 402 is attached and at the other end the flat-panel imager 404 is attached. The C-arm 610 is moved either manually or by a motor within the arm support 611, so that the x-ray tube 402 and the flat-panel imager 404 can move along an arc.

Note that in this embodiment, the distance from the x-ray tube 402 to the axis of rotation 428 is not necessarily equal to the distance from the radiation therapy source 409 to the axis of rotation 428. The arm 610 does not necessarily be in the shape of an arc of a circle. Also, the axis of rotation of the arm 610 is not necessarily coincident with the axis of rotation 428 of the radiation therapy source 409, which allows the same device to be fitted on machines with different face-to-iso-center distances without altering the radius of the C-arm 610.

Use of the C-arm 610 of FIGS. 21(*a*)-(*b*) allows for a great amount of flexibility in obtaining cone beam computerized tomography images. For instance, image data can be obtained by only having the drum 408 of the gantry 406 rotate. Image data can be obtained in a second manner by having the C-arm 610 move independently of the gantry 406 in a circular path. Image data can be obtained by having the C-arm 610 and the drum 408 work cooperatively to generate images along a circular path so that the angular range of acquisition is increased and so instabilities in the angular velocity of the gantry are addressed. A fourth manner of imaging involves rotating the drum 408 and pivoting the C-arm 610 about the mounting point on the gantry 406 with a sinusoidal pattern to effect non-circular orbits that involve a sinusoidal trajectory on a spherical surface. Such a non-circular orbit allows more complete image reconstructions by satisfying Tuy's condition.

FIG. 22 shows a portable cone beam computerized tomography system 700. In this embodiment, the system 700 is on a mobile platform 702 so that it can be moved relative to a patient 441 positioned on a table 443 relative to a rotating radiation therapy source 409 (not shown). The cone beam computerized tomography system 700 includes an x-ray source, such as x-ray tube 402 positioned on one side of a C-arm 704, and a flat-panel imager 404 positioned on an opposite side of the C-arm 704. The C-arm 704 can rotate about two axes of rotation when in operation. The system 700 can be moved to a radiation therapy system (not shown) and can be used to generate images that aid in the alignment of the radiation therapy system.

With the above descriptions of the cone beam computerized tomography system 400 and the various embodiments of the imager support systems shown in FIGS. 18-22 in mind, operation of the system 400 is described below. In the description to follow, the term "shape" of the radiation therapy beam 411 is understood to refer to the spatial distribution of the beam in a plane perpendicular to the direction of the beam or to the frequency modulation of the beam after being transmitted through some beam-limiting device. The term "planning image" refers to an image of the patient acquired by the cone beam computerized tomography system 400 prior to treatment delivery used for radiation therapy treatment planning The term "constrained plan set" refers to a plurality of radiation therapy treatment plans for a given patient, where each radiation therapy treatment plan is calculated assuming some perturbation of lesion location and/or orientation compared to that in the planning image. For example, a constrained plan set could be calculated where each plan corresponds to a different magnitude of lesion rotation about the y and/or z axes.

Figure 23A:
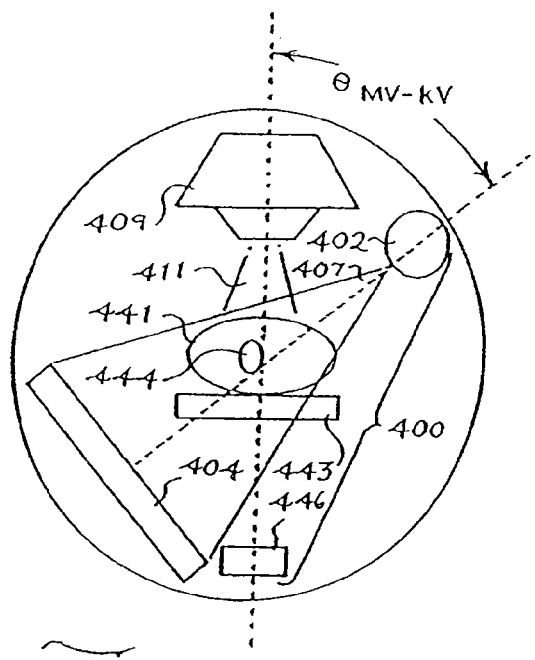
FIGS. 23(a)-(d) are diagrammatic sketches illustrating the geometry and operation of the cone beam computerized tomography imaging systems of FIGS. 17-22.
Figure 23B:
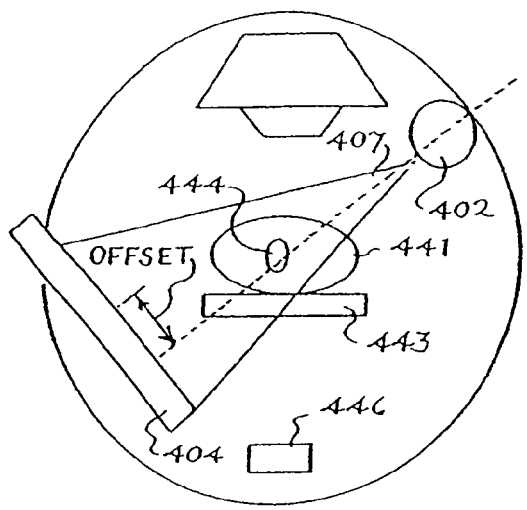
Figure 23C:
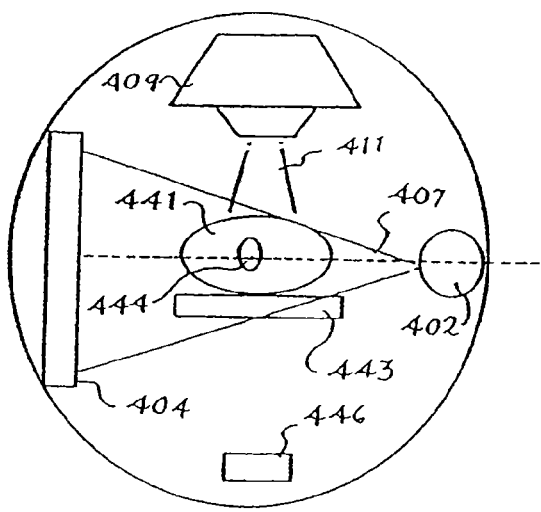

The cone beam computerized tomography imaging system 400 preferably includes an x-ray tube 402 and a flat panel imager 404 in any one of the geometries illustrated in FIGS. 23(a)-(d), capable of forming 3-D images of the patient on the treatment table in the treatment position. The x-ray tube 402 may be operated so as to produce a pulsed or continuous beam of x-rays 407. The flat panel imager 404 includes an active matrix of imaging pixels incorporating mechanisms for: 1.) converting incident x-rays to electronic charge (e.g., a scintillator in combination with optically sensitive elements at each pixel, or a photoconductor); 2.) integrating and storing the electronic charge at each pixel (e.g., the capacitance of photodiode(s), capacitors, etc. located at each pixel); and 3.) reading the electronic charge out of the device (e.g., a thin-film transistor switch or the like at each pixel, with associated switching control lines and readout lines). The x-ray tube 402 and the flat panel imager 404 preferably move in a circular orbit (or variation thereof) about the longitudinal axis of the patient. Depending on which ones of the imager support systems used in FIGS. 18-22, the imager support system should accommodate offsets in the x and/or z directions as illustrated in FIG. 23(b). Note that the combined motion of the x-ray tube 402 and/or the flat panel imager 404 in x, y, and/or z is termed the orbit, and may be circular about the patient, or non-circular, e.g., comprising of some combination of linear, sinusoidal, circular, and/or random paths. For example, in the case where the source 402 and imager 404 move independently with respect to one another, the source 402 can move on a sinusoidal or sawtooth path constrained to the surface of a cylinder while the imager 404 moves in a circular path on the surface of a cylinder. In this scenario, the collimator adjusts in real time the shape of the radiation field so it is confined to the imager 404 despite the allowed independent motion of the source 402 and imager 404.

Figure 23D:
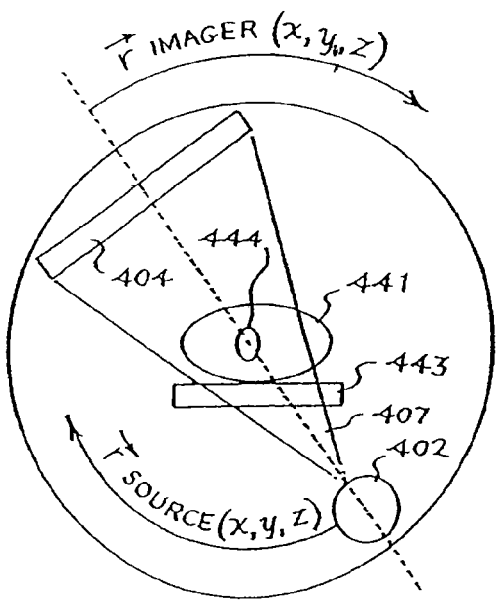

Cone beam computerized tomography image acquisition involves acquisition of a plurality of 2-D images, where each image preferably corresponds to a different orientation of the x-ray beam 407 and the flat panel imager 404 with respect to the patient 441, e.g., where the x-ray tube 402 and the flat panel imager 404 traverse a circular or non-circular path about the patient 441 as illustrated in FIG. 23(d). Note that the cone beam computerized tomography image is preferably acquired with the patient on the treatment table, in the treatment position, and immediately prior to treatment delivery. The processes involved in the preferred method for cone beam computerized tomography image acquisition are illustrated in FIG. 24, divided conceptually into a variety of off-line and on-line processes, and mechanisms for 2-D image acquisition and 3-D image reconstruction.

Figure 24:
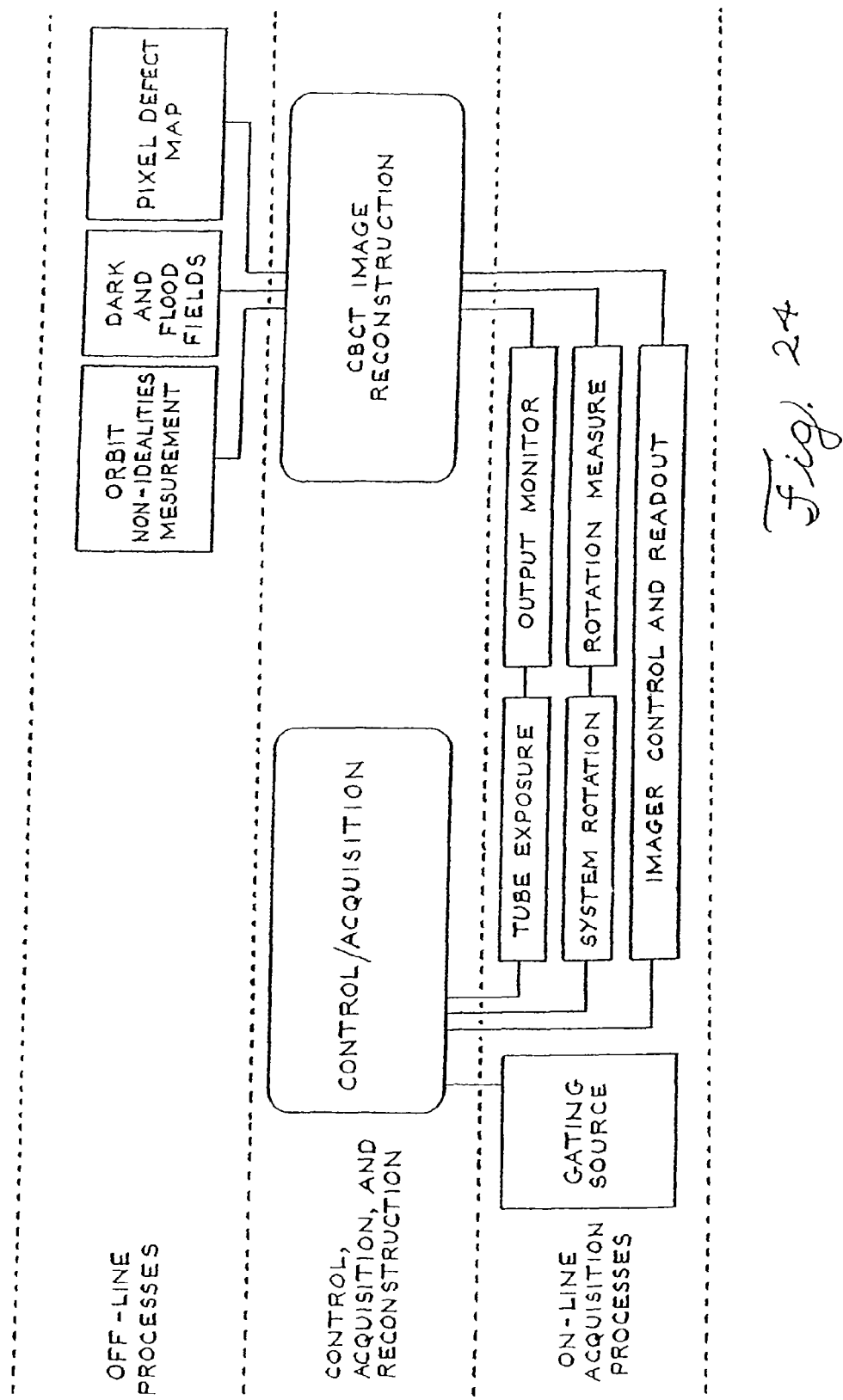
FIG. 24 is a flow-chart showing an embodiment of the processes involved in acquiring a cone beam computerized image for the cone beam computerized tomography imaging systems of FIGS. 17-22.

The off-line processes schematically shown in FIG. 24 include acquisition of a plurality of 2-D images acquired in the absence of x-ray irradiation (termed dark fields) and with uniform x-ray irradiation (termed flood fields). Such dark and flood fields are used to correct stationary nonuniformities in the imaging system arising from nonuniformity in pixel operational and response characteristics. Also included is a mechanism for identifying and correcting defective pixels in the 2-D images (e.g., a pixel defect map that identifies aberrant pixel coordinates, and application of a filter to the corresponding pixel values). Thirdly, a measure and process for correction of orbit non-idealities, described below, is preferably employed.

The on-line processes schematically shown in FIG. 24 include: 1.) control and monitoring of the x-ray tube; 2.) control and monitoring of the orbit traversed by the x-ray tube 402 and the flat panel imager 404 (e.g., by rotating the gantry 406); and 3.) control and readout of the flat panel imager 404. The x-ray source 402 produces x-rays in either a pulsed or continuous manner, and variations in the magnitude of x-ray tube output are monitored by an output monitor, which preferably includes a radiation sensitive electronic device such as a diode placed inside the x-ray tube collimator assembly. Alternatively, the output monitor could be placed outside the x-ray tube 402 in a position that allows it to measure variations in x-ray tube output, or the output could be measured using pixels on the flat panel imager 404, such that these pixels are not occluded by the patient in the plurality of 2-D projection images. The orbit of the x-ray tube 402 and the flat panel imager 404 about the patient is preferably controlled via computer-controlled rotation of the gantry 406, combined with a precise measurement of the gantry angle at which each 2-D image is acquired. For embodiments in which the x-ray source 402 and the flat panel imager 404 are not both mounted on the treatment gantry 406, such as the portable embodiment of FIG. 22, a similar mechanism for measuring and recording the location of these two components for each 2-D image is employed. Thirdly, a plurality of 2-D images are read from the flat panel imager 404 by a control/acquisition computer. The readout of the flat panel imager 404 is preferably synchronized with the operation of the x-ray tube 402 as well as with the rotation of the x-ray tube 402 and the flat panel imager 404 support structure(s), such as those described previously with respect to FIGS. 18-22. The timing of x-ray exposures, gantry rotation, and flat panel imager readout is preferably synchronized by: 1.) the control/acquisition computer; or 2.) an external trigger mechanism (gating source), such as a device for active breathing control, electrocardiac gating, etc. For the former case, the preferred embodiment includes computer-control of: 1.) x-ray pulses generated by the x-ray source 402; 2.) gantry rotation (e.g., in increments of .about.1.degree. through .about.360.degree.); and flat panel imager readout (e.g., at a readout rate consistent with the limitations in x-ray tube output and gantry rotation). For the latter case, the preferred embodiment is such that the gating source triggers x-ray production, gantry rotation, and flat panel imager readout in a manner synchronized with the motion of anatomical structures in the patient 441 in order to reduce the deleterious effects of organ motion in image reconstructions.

The preferred embodiment includes a mechanism (reconstruction engine) for high-speed cone beam computerized tomography image reconstruction. The plurality of 2-D projections is first processed by dark and flood field correction, and the measurements of orbit non-ideality (below), tube output variations, and gantry rotation are used together with the processed 2-D projections to form 3-D cone beam computerized tomography image reconstructions of the patient 441. A variety of cone-beam reconstruction techniques are known within the art, including cone-beam filtered back-projection. The cone beam computerized tomography image is then made available to a system for on-line treatment planning.

In the interim between the 2-D image acquisition and correction of lesion localization errors, the patient 441 is preferably monitored by periodic radiographs obtained with the flat panel imager at one or more gantry angles. In the preferred embodiment, these monitor radiographs are analyzed (e.g., by calculation of difference images) in order to provide a check against intrafraction motion of the patient 441.

The preferred embodiment includes a computer-controlled treatment table 443 for correction of lesion localization errors. The table 443 controlled by a computer, such as computer 900 schematically shown in FIG. 17(a), preferably allows translation of the patient 441 in the x, y, and z directions as well as rotation about the x axis. Rotation about the y axis (tilt) and z axis (roll) is possible for an embodiment in which lesion localization errors are corrected by such motions (as opposed to correction of such errors through selection of an appropriate RTTP from a constrained plan set), provided that such motions do not cause uncertainty in the location/orientation of the lesion 444 and/or surrounding structures, e.g., due to the effects of gravity. Furthermore, the treatment table 443 is preferably constructed of radio-translucent material so as not to interfere significantly with the acquisition of cone beam computerized tomography images.

As one of ordinary skill in the art would readily understand, from the frame of reference of an object, such as a patient, on the table 443, it will appear that the radiation therapy source moves during the correction of lesion localization errors.

Figure 25:
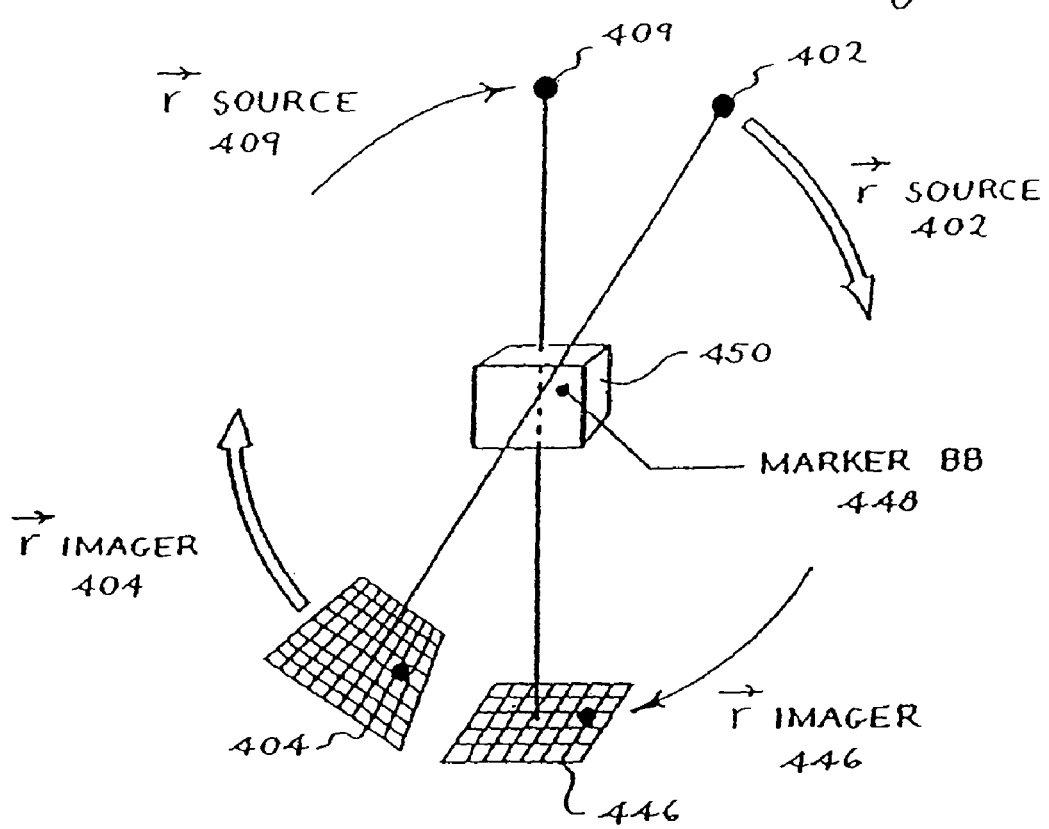
FIG. 25 is a perspective drawing illustrating an embodiment of a method for geometric calibration of the imaging and treatment delivery systems of FIGS. 17-22.

The preferred embodiment includes a method for calibration of the radiation therapy delivery system accomplished using a radiation therapy system including the radiation therapy source 409, a collimating structure such as a multi-leaf collimator, and an imager 446. The imager 446 is located opposite the radiation therapy source 409 on a support arm attached to the radiotherapy gantry 406 and in the preferred embodiment is a flat panel imager 404 designed for imaging of the high energy beam 411. The calibration method preferably employs a reference BB 448 embedded in a lucite cube 450 and located at a known location with respect to the isocenter 430 of gantry rotation, as illustrated in FIG. 25. The cube 450 is precisely leveled, and marks on the cube surface project the location of the isocenter within the cube. The reference BB 448 is imaged at angular increments using the radiation therapy source 409 and imager 446 as the gantry 406 rotates through 360.degree., preferably clockwise and counter-clockwise. In each image, the reference BB 448 is located preferably by an automated centroid calculation, and the edge of each leaf of the multi-leaf collimator and the edge of the collimators are localized by calculation of maximum signal gradient. After subtracting a sinusoid of specified amplitude from the measured deflections, the residuals represent imperfections in leaf placement. These residuals can then be incorporated into the controller of the multi-leaf collimator and calibrated out. An alternative approach is to modify the planning system to generate "corrected" leaf positions. After calibration, the patient positioning lasers in the treatment room are adjusted to the set of laser alignment marks located on the lucite cube.

The preferred embodiment furthermore includes a calibrator that calibrates the cone beam computerized tomography imaging geometry relative to that of the radiation therapy source 409. Calibration of the cone beam calibration tomography geometry is preferably performed immediately following multi-leaf collimator leaf calibration, without moving the reference BB 448. The same procedure is performed using the x-ray source 402 and the flat panel imager 404; however, in this case, the residuals are used to adjust the back-projection trajectories in the reconstruction process. The image of the localized BB 448 is preferably analyzed using a 3-D centroid algorithm, and the location of isocenter 430 is calculated as a simple offset from the centroid. The isocenter 430 can thus be explicitly identified within the 3-D matrix of cone beam computerized tomography images.

In the preferred embodiment, the cross-calibration of the cone beam computerized tomography imaging system 400 and the radiation therapy delivery system can be tested with a mechanism (phantom) for combined geometry and dosimetry measurement. The phantom preferably includes a water-filled or water-equivalent volume in which a dosimetry insert is rigidly placed at various locations. The dosimetry insert preferably contains either: 1.) a detector matrix of electronic dosimeters, or 2.) a volume of radiosensitive gel dosimeter. In the former case, the dosimeters are embedded in a water-equivalent insert and placed asymmetrically to allow unambiguous identification in a computerized tomography image; furthermore, each dosimeter is sufficiently small as to have legible influence on the dosimetry of other detectors. The electronic signals from the dosimeter matrix are preferably used in either of two ways: 1.) the dosimetry of a complete delivery can be tested by recording the signal from all detectors and comparing to calculations, thereby providing a point dose verification of the delivery as well as routine pretreatment quality assurance; and/or 2.) the precision and accuracy of the combined imaging and delivery system can be measured by recording the dose to the detectors as the geometric edge of a leaf can be inferred and compared to the planning system dose calculation. This test is preferably performed for all the leaves in the system by moving the location of the dosimetry insert within the volume. In the case of a radiosensitive gel dosimeter, measurement of 3-D dose distributions delivered by a given treatment scheme can be quantitatively evaluated.

The preferred embodiment furthermore includes delineating the target volume immediately following acquisition of the cone beam computerized tomography image of the patient 441 on the treatment table 443 in the treatment position. Localization of the target volume/lesion 444 and/or surrounding structures can be performed manually, e.g., by contouring of structures in some combination of transaxial, sagittal, coronal, and/or oblique slices. Alternatively, the target volume/lesion 444 and/or surrounding structures can be delineated by an automated localization algorithm, as recognized in the art. In this approach, the target volume/lesion 444 defined in the planning image is overlaid on a given on-line cone beam computerized tomography image, and the images are matched, e.g., by translating and rotating the reference target contour in such a way as to minimize the standard deviation of pixel values compared to the planning image. In the planning image, bony structures are defined, and matching of the planning image with the on-line cone beam computerized tomography image (both with calibrated isocenter positions) on bony structures determines the setup error (rotation and translation) of the bony anatomy. The motion of the soft-tissue target relative to the bony anatomy is quantified by translating and rotating the target volume contours until they cover a homogeneous area (i.e., standard deviation in pixel value differences is minimized).

The treatment plan for the current session can be modified based on the cone beam computerized tomography image data by a number of methods or combinations therein, including recalculation of the RTTP, selection of a modified RTTP from a previously calculated set of plans, and/or translation, rotation, and/or angulation of the patient. The method chosen should provide a modified plan for the current treatment session in a manner that does not cause uncertainty in the location/orientation of the lesion; therefore, the method should be completed within a short time frame in order to minimize intrafraction organ motion effects, and should not significantly distort patient anatomy. Recalculation of the RTTP based on the cone beam computerized tomography image data should be consistent with such time constraints. Similarly translation, rotation, and/or angulation of the patient should not perturb patient anatomy compared to that measured in the cone beam computerized tomography image, e.g., due to the effects of gravity.

As one of ordinary skill in the art would readily understand, from the frame of reference of the patient being translated, rotated and/or angulated as described above, it will appear that the radiation therapy source moves relative to the patient.

Figure 26:
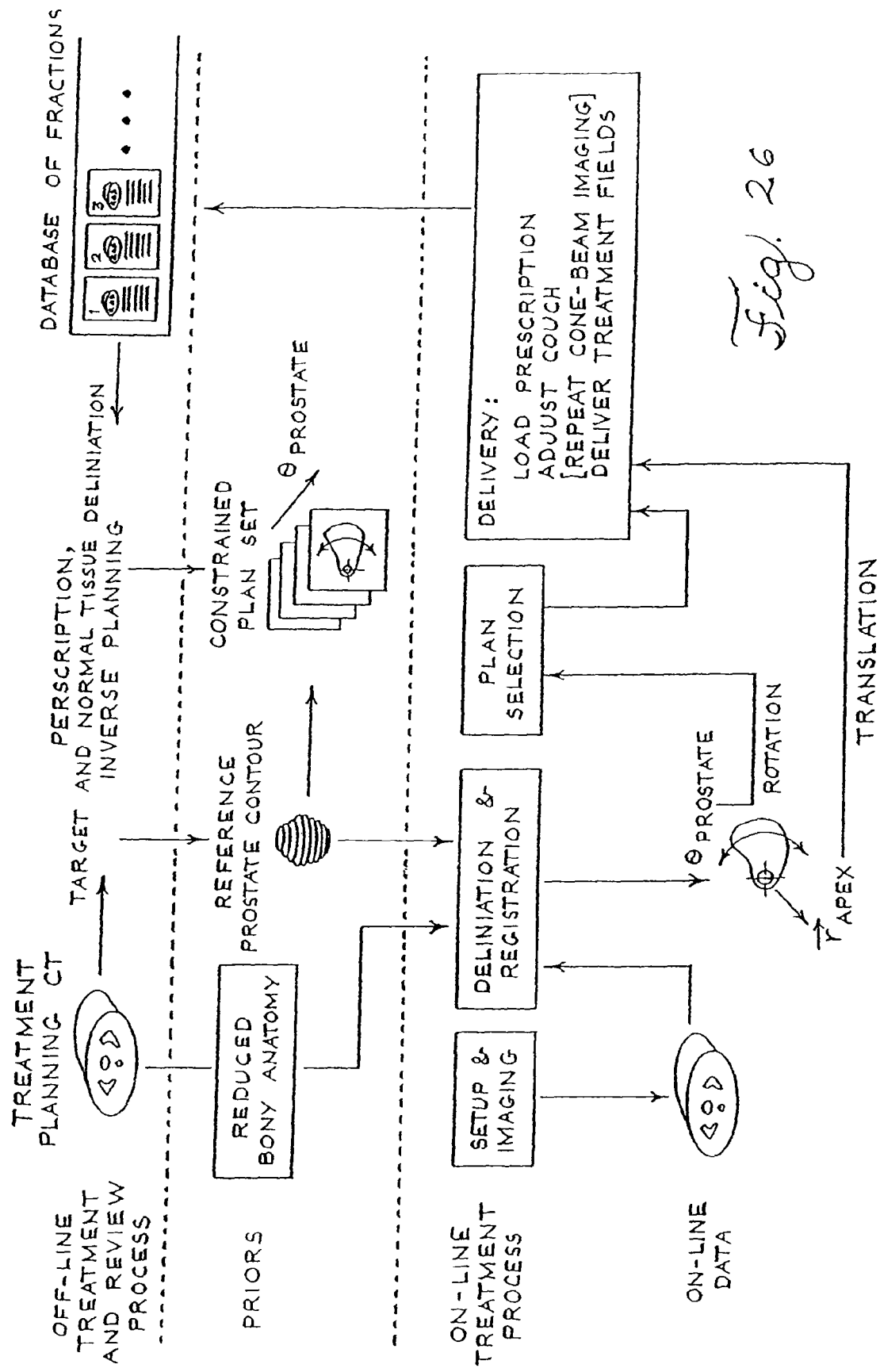
FIG. 26 is a flow-chart showing an embodiment of the processes involved in the image-guided radiation therapy systems of FIGS. 17-22, based on cone beam computerized tomography imaging of a patient, on-line correction of setup errors and organ motion, and off-line modification of subsequent treatment plans.

The preferred embodiment entails a streamlined process for rapid lesion localization, selection of an appropriate RTTP, dosimetry review, and transfer of the prescription to the radiation therapy delivery system. The process for on-line cone beam computerized tomography guidance of radiation therapy procedures is illustrated in FIG. 26, which conceptually separates the system into: 1.) the off-line treatment process; 2.) priors for on-line selection and correction; and 3.) the on-line imaging and treatment process.

The off-line treatment process in the preferred embodiment begins with a planning image on which contours of the target volume and surrounding structures are defined, and margins for target deformation, delivery precision, and delineation precision are applied. Inverse planning is performed according to a given protocol for radiation therapy of the given treatment site, e.g., a number of radiation therapy beams 411 directed at the patient 441 from various angles, with target dose uniformity and normal tissue volume constraints to match the prescription. In addition to this reference plan, a plurality of additional plans (the constrained plan set) are generated as a function of various translations and/or rotations of the target volume. Plans are preferably generated at small increments of each possible translation and/or rotation (e.g., rotation of the target volume about the y axis).

In the preferred embodiment for on-line plan selection and correction of lesion localization errors, the target volume/lesion 444 and its relationship to bony structure in the planning image are prepared for use as priors, and the constrained plan set is transferred to the radiation therapy system to verify deliverability prior to the on-line procedure. In the on-line treatment process, the patient 441 is set up on the treatment table 443 in the treatment position, and cone beam computerized tomography images are acquired as described above. The target volume/lesion 444 and surrounding structures are delineated in the cone beam computerized tomography data, thereby identifying the translations and/or rotations of the target volume/lesion 444 relative to the position and orientation in the planning image. As described above, translations may be corrected by translation of the computer-controlled treatment table 443, and rotations may be corrected by selection of an appropriate plan from the constrained plan set. The translation of the lesion 444 observed in the cone beam computerized tomography image relative to the planning image is corrected by translation of the patient 441 on the treatment table 443 in the y and/or z directions, and/or by rotation about the x axis. The orientation of the lesion 444 (i.e., rotations about the y and/or z axes) are corrected by selecting from the previously calculated constrained plan set a modified RTTP that most closely corresponds to the measured rotation of the lesion 444. Meanwhile, radiographic monitoring of the patient 441 can be used to check against intrafraction motion of the patient 441. Furthermore, a cone beam computerized tomography image acquired immediately prior to, during, or following the treatment procedure can be obtained in order to provide accurate representation of the location of patient anatomy during treatment delivery, which can be stored for off-line review, evaluation, and modification of subsequent treatment sessions. Following transferal of the prescription to the delivery system, the treatment plan is executed according to the patient setup and treatment plan determined from the cone beam computerized tomography image.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims. For example, the cone beam computerized tomography system can be adapted to perform animal testing identification, and non-invasive and non-destructive component structural testing.

We claim:

1. A method of calibrating a radiation therapy system that comprises:
   1) a cone beam computed tomography image system that includes a flat panel imager and a keV x-ray source that generates x-ray beams in a cone-beam form towards the flat panel imager and 2) a radiation therapy source system comprising: a radiation therapy source that generates radiation, a collimating structure and an imager that is located opposite said radiation therapy source that generates therapeutic radiation, the method comprising:
   calibrating said radiation therapy source system, said calibrating said radiation therapy source system comprising:
      providing a reference marker embedded in an object located at a known location with respect to an isocenter of rotation of said radiation therapy source and said imager;
      directing said therapeutic radiation towards said object and said imager;
      generating images of said reference marker by said therapeutic radiation at angular increments of positions of said radiation therapy source and said imager; and
      calibrating said collimating structure based on said generated images;
   calibrating said cone beam computed tomography image system, said calibrating of said cone beam computed tomography image system comprises:
      directing said x-ray beams towards said object and said flat panel imager;
      generating images of said reference marker by said x-ray beams at angular increments of positions of said keV x-ray source and said flat panel imager;
   determining residuals based on said generated images; and
      subsequently generating cone beam computed images of a second object, wherein said generated cone beam computed images are generated based on calibrating back-projection trajectories in a reconstruction process involving said generated cone beam computed images.

2. The method of claim 1, wherein said calibrating said cone beam computed tomography image system is performed immediately after said calibrating said radiation therapy source system is performed.

3. The method of claim 1, wherein said collimator comprises a multi-leaf collimator wherein edges of each leaf are localized by calculation of maximum signal gradient; said method further comprising:
   generating residuals by subtracting a sinusoid of specified amplitude from measured deflections of each leaf, wherein said residuals represent imperfections in leaf placement; and
   controlling each leaf by calibrating out said residuals.

4. The method of claim 1, wherein radiation therapy source is an MeV radiation therapy source.

5. A process for on-line cone beam computed tomography guidance of radiation therapy procedures that involves: 1) a cone beam computed tomography image system that includes a flat panel imager and a keV x-ray source that generates x-ray beams in a cone-beam form towards the flat panel imager and 2) a radiation therapy source system comprising: a radiation therapy source that generates therapeutic radiation, a collimating structure and an imager that is located opposite said radiation therapy source that generates therapeutic radiation, the process comprising:

performing an off-line treatment process comprising:
providing a planning image on which contours of a target volume of an object to be treated and surrounding structures are defined;
performing inverse planning according to a given protocol for radiation therapy of said object so as to generate a reference plan;
generating a plurality of additional plans as a function of various translations and/or rotations of said target volume;

performing an on-line treatment process comprising:
positioning said object on a treatment table;
acquiring cone beam computed tomography images of said object on said treatment table;
delineating said target volume and surrounding structures in said cone beam computed tomography images so as to identify translations and/or rotations of said target volume relative to a position and orientation in said planning image;
correcting translation of said object observed in said cone beam computed tomography images relative to said planning image by translation of said object on said treatment table in y and/or z directions, and/or by rotation about an x axis; and
correcting orientation of said target volume by selecting from said reference plan and said plurality of additional plans a modified radiation therapy treatment plan that most closely corresponds to a measured rotation of said target volume.

6. The method of claim 5, further comprising performing radiographic monitoring of said object to check against intrafraction motion of the object.

7. The method of claim 5, wherein said delineating said target volume is performed manually by contouring of structures in some combination of transaxial, sagittal, coronal, and/or oblique slices.

8. The method of claim 5, wherein said delineating said target volume is performed by an automated localization algorithm that results in overlaying said target volume defined in said planning image on a given cone beam computed tomography image, and matching said images by translating and rotating a contour of said target volume in said planning image in such a way as to minimize a standard deviation of pixel values compared to said planning image.

9. The method of claim 5, wherein said radiation therapy source is an MeV radiation therapy source.

10. The method of claim 5, wherein said on-line treatment process comprises controlling a path of a beam of said therapeutic radiation through said target volume in response to said modified radiation therapy treatment plan.

11. The method of claim 10, wherein said acquiring cone beam computed tomography images of said object on said treatment table; is performed substantially at a time of occurrence of said controlling said path of said beam of radiation through said target volume.

* * * * *